(12) United States Patent
Qian et al.

(10) Patent No.: US 11,661,420 B2
(45) Date of Patent: May 30, 2023

(54) COMPOUND CONTAINING FUSED RING, USE THEREOF AND PHARMACEUTICAL COMPOSITION CONTAINING SAME

(71) Applicant: NANJING HEPO PHARMACEUTICAL CO., LTD, Jiangsu (CN)

(72) Inventors: Pengfei Qian, Jiangsu (CN); Fengbo Li, Jiangsu (CN); Xuejun Liu, Jiangsu (CN); Xiaodong Chen, Jiangsu (CN); Lijun Guo, Jiangsu (CN); Kai Sun, Jiangsu (CN)

(73) Assignee: NANJING HEPO PHARMACEUTICAL CO., LTD, Jiangsu (CN)

( * ) Notice: Subject to any disclaimer, the term of this patent is extended or adjusted under 35 U.S.C. 154(b) by 0 days.

(21) Appl. No.: 17/594,524

(22) PCT Filed: Apr. 22, 2020

(86) PCT No.: PCT/CN2020/086026
§ 371 (c)(1),
(2) Date: Oct. 20, 2021

(87) PCT Pub. No.: WO2020/221074
PCT Pub. Date: Nov. 5, 2020

(65) Prior Publication Data
US 2022/0213085 A1   Jul. 7, 2022

(30) Foreign Application Priority Data

Apr. 30, 2019 (CN) .......................... 201910361418.8

(51) Int. Cl.
| | | |
|---|---|---|
| *C07D 417/04* | (2006.01) | |
| *C07D 403/04* | (2006.01) | |
| *C07D 405/04* | (2006.01) | |
| *C07D 413/04* | (2006.01) | |
| *C07D 417/14* | (2006.01) | |
| *C07D 491/107* | (2006.01) | |

(52) U.S. Cl.
CPC ......... *C07D 417/04* (2013.01); *C07D 403/04* (2013.01); *C07D 405/04* (2013.01); *C07D 413/04* (2013.01); *C07D 417/14* (2013.01); *C07D 491/107* (2013.01); *C07B 2200/13* (2013.01)

(58) Field of Classification Search
CPC .. C07D 403/04; C07D 413/04; C07D 417/04; C07D 405/04; C07D 417/14; C07D 491/107
USPC ...................................... 514/230.5
See application file for complete search history.

(56) References Cited

U.S. PATENT DOCUMENTS

| | | |
|---|---|---|
| 4,229,343 A | 10/1980 | Junge et al. |
| 7,354,945 B2 | 4/2008 | Mujica-Fernaud et al. |
| 2011/0263620 A1 | 10/2011 | Hsieh et al. |

FOREIGN PATENT DOCUMENTS

| | | |
|---|---|---|
| WO | 2010069147 A1 | 6/2010 |
| WO | 2014080291 A2 | 5/2014 |
| WO | 2015113990 A1 | 8/2015 |
| WO | 2016128335 A1 | 8/2016 |

OTHER PUBLICATIONS

Mar. 21, 2022 First Office Action issued in Chinese Patent Application No. 202010321654X.
May 10, 2022 Japanese First Office Action issued in Japanese Patent Application No. 2021-565132.
Aug. 11, 2020 International Search Report issued in international application No. PCT/CN2020/086026.
Aug. 11, 2020 Written Opinion of the International Searching Authority issued in international application No. PCT/CN2020/086026.
Fabien Zoulim and David Durantel, Antiviral Therapies and Prospects for a Cure of Chronic Hepatitis B, Cold Spring Harb Perspect Med. 2015;5:a021501.
Erik H. C. J. Buster et al., Peginterferon Alpha-2b Is Safe and Effective in HBeAg-Positive Chronic Hepatitis B Patients with Advanced Fibrosis, Hepatology, (2007), 46, 388-94.
Chih-Lin Lin et al., New perspectives of biomarkers for the management of chronic hepatitis B, Clin Mol Hepatol. Dec. 2016; 22(4): 423-431.
Anne Marie Dougherty et al., A Substituted Tetrahydro-Tetrazolo-Pyrimidine Is a Specific and Novel Inhibitor of Hepatitis B Virus Surface Antigen Secretion, Antimicrob Agents Chemother 2007, 51 (12), 4427-4437.
Wenquan Yu et al., Design, Synthesis, and Biological Evaluation of Triazolo-pyrimidine Derivatives as Novel Inhibitors of Hepatitis B Virus Surface Antigen (HBsAg) Secretion, J. Med. Chem. 2011, 54 (16), 5660-5670.
Yi-Bin Xu et al., Benzimidazole derivative, BM601, a novel inhibitor of hepatitis B virus and HBsAg secretion. Antiviral Res 2014, 107, 6-15.
Jul. 21, 2022 the First Office Action issued in European application No. 20799482.3.

*Primary Examiner* — Kahsay Habte
(74) *Attorney, Agent, or Firm* — Houston Beshining Law Office PLLC; Liangang Ye

(57) ABSTRACT

Disclosed are a compound containing a fused ring, a use thereof and a pharmaceutical composition containing same. Provided are a compound as shown in formula I-A, a pharmaceutically acceptable salt thereof, a solvate thereof, a solvate of the pharmaceutically acceptable salt thereof or a crystal form thereof. The compound can significantly reduce the levels of HBsAg, HBeAg and HBV DNA, and can be used for preparing a drug for treating hepatitis B, and has good market prospects. (I-A)

12 Claims, No Drawings

COMPOUND CONTAINING FUSED RING, USE THEREOF AND PHARMACEUTICAL COMPOSITION CONTAINING SAME

The present disclosure is a National Stage of International Application No. PCT/CN2020/086026 with the tiling date of Apr. 22, 2020, which claims the priority of the Chinese patent application 2019103614188 with the tiling date of Apr. 30, 2019. The present disclosure refers to the full text of the above Chinese patent disclosure.

TECHNICAL FIELD

The present disclosure relates to a compound containing a fused ring, a use thereof and a pharmaceutical composition containing same.

PRIOR ART

Hepatitis B is a viral disease caused by hepatitis B virus (HBV) infection, which can cause liver damage. As a global epidemic that seriously threatens human health, according to WHO statistics, by 2015, there were approximately 257 million people with chronic hepatitis B virus infection in the world (global hepatitis report, 2017). Among them, in 2015 alone, hepatitis B and its complications (including liver cirrhosis and hepatocellular carcinoma) led to 887,000 deaths (WHO Hepatitis B Fact Sheet; World Health Organization: Geneva, Jul. 18, 2018). Therefore, hepatitis B has become a serious global public health problem.

HBV is a partially double-stranded relaxed circular DNA (rcDNA) consisting of a complete negative strand and an incomplete positive strand. HBV is a hepadnavirus, after entering the human body, the virus is distributed to the whole body through blood circulation and finally enriched in the liver. HBV mainly damages hepatocytes and causes hepatocyte inflammation, without intervention treatment, it will develop into hepatocyte necrosis, liver fibrosis or more serious hepatocellular carcinoma.

Currently, the FDA-approved drugs for hepatitis B treatment include two main classes of interferon (INF) and nucleoside (acid) analogs (NAs). Among them, interferon includes INF α-2b and pegylated interferon α-2a (pegylated INF α-2a); nucleoside (acid) analogues mainly include nucleoside analogues: lamivudine (LAM), telbivudine (LDT), entecavir (ETV) and nucleotide analogues: adefovir dipivoxil (ADV), tenofovir dipivoxil (TDF), tenofovir alafenamide (TAF). Although the treatment course of interferon therapy is relatively short and it is not easy to produce drug resistance, it is inconvenient to administer, requires subcutaneous and intramuscular injections, and has flu-like side effects. Moreover, the response rate of interferon therapy is not high. Nucleoside (acid) analogs mainly achieve the antiviral effect by inhibiting the replication of HBV DNA. Although it can reduce HBV DNA to a low level in a short period of time, it cannot completely eliminate HBV infection and is prone to relapse and rebound after stopping the drug, so patients often need long-term medication.

Currently, the key to a functional cure of hepatitis B is the complete clearance of HBV DNA and the disappearance of hepatitis B surface antigen (HBsAg), and the production of hepatitis B surface antibodies (HBsAb) (Cold Spring Harb Perspect Med. 2015; 5: a021501). The above treatments, especially nucleoside (acid) drugs, do not reduce HBsAg levels, although they can rapidly reduce the virus level and permanently inhibit viral replication with long-term medication. Clinical observations have shown that long-term use of nucleoside (acid) drugs cannot improve the HBsAg clearance rate, which is remained similar to the natural clearance rate (Hepatology, (2007), 46, 388-94). In addition, serum HBsAg concentration is closely related to the risk of liver cancer and virus clearance, the lower the HBsAg concentration, the higher the probability of being cleared in the future. In patients with low HBV DNA content, the higher the HBsAg concentration, the greater the risk of liver cirrhosis and liver cancer (lower than patients with high HBV DNA content) (Clin Mol Hepatol. 2016 December; 22(4): 423-431).

However, for the production and release of HBsAg, no drugs have been marketed so far. Among the small molecule HBsAg inhibitors in preclinical or clinical studies, HBF-0259 showed good activity in inhibiting HBsAg secretion with $EC_{50}$ values of 1.5 μM (HepDE19 cells) and 11.3 μM (HepG 2.2.15 cells) (Antimicrob Agents Chemother 2007, 51 (12), 4427-4437). After further optimization, the compound PBHBV-2-15 was obtained with an $EC_{50}$ value of 1.4 μM (HepG2.2.15 cells) (J. Med. Chem. 2011, 54 (16), 5660-5670). BM601 can inhibit HBV DNA and HBsAg at the same time, its $EC_{50}$ value is 0.6 μM and 1.5 μM, but has certain cytotoxicity with a $CC_{50}$ value of 24.5 μM (Antiviral Res 2014, 107, 6-15). In addition, Roche also reported in WO2015113990 and WO2016128335 a class of dihydroquinazinone compounds, which have the effect of reducing HBsAg levels, but there has been no clinical progress in this class of compounds so far.

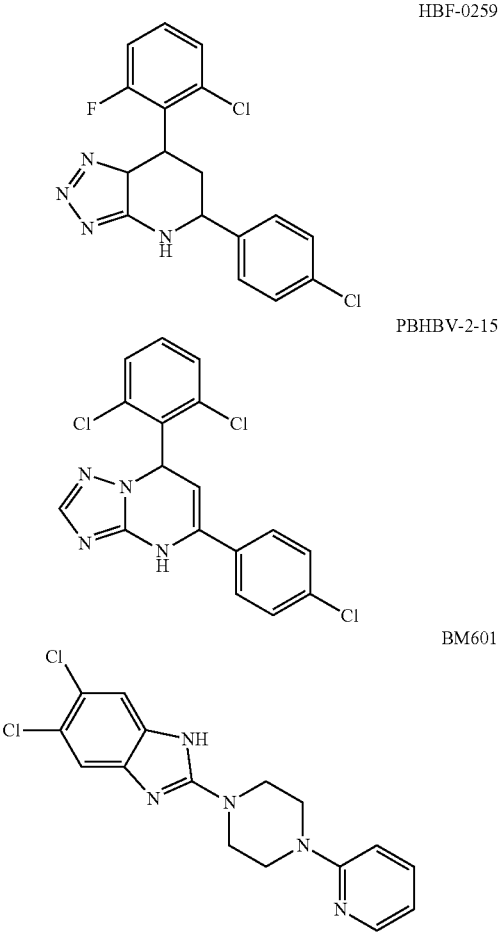

-continued

RG7834

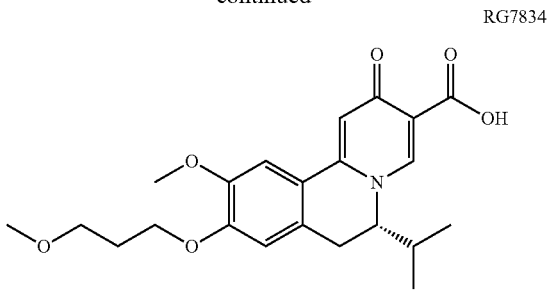

CONTENT OF THE PRESENT INVENTION

The technical problem to be solved by the present disclosure is the defect of single structure of the existing compound capable of significantly reducing the levels of HBsAg, HBeAg and HBV DNA, and to this end, the present disclosure provides a compound containing a fused ring, a use thereof and a pharmaceutical composition containing same. The compound can significantly reduce the levels of HBsAg, HBeAg and HBV DNA, and can be used for preparing a drug for treating hepatitis B, and has good market prospects.

The present disclosure provides a compound as shown in formula I-A, a pharmaceutically acceptable salt thereof, a solvate thereof, a solvate of the pharmaceutically acceptable salt thereof or a crystal form thereof,

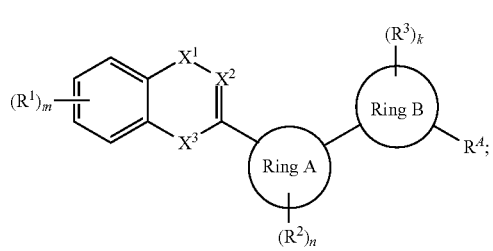

I-A wherein, m is 0, 1 or 2;

$R^1$ is halogen, $C_1$-$C_3$ alkyl, $C_1$-$C_3$ alkyl substituted by one or more halogens, $C_1$-$C_3$ alkoxy, or $C_1$-$C_3$ alkoxy substituted by one or more halogens;

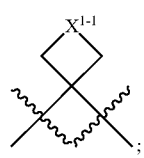

$X^1$ is —C($R^4R^5$)—, or;

$R^4$ is $C_1$-$C_3$ alkyl, $C_1$-$C_3$ alkyl substituted by one or more halogens, or, $C_3$-$C_5$ cycloalkyl; $R^5$ is hydrogen, $C_1$-$C_3$ alkyl, $C_1$-$C_3$ alkyl substituted by one or more halogens, or, $C_3$-$C_5$ cycloalkyl; $X^{1-1}$ is a single bond, O, $CH_2$ or $CH_2CH_2$;

$X^2$ is O, N or CH;

$X^3$ is O, S, NH or $CH_2$;

ring A is a "5-membered heteroaromatic ring containing 1, 2 or 3 heteroatoms independently selected from N, O and S";

n is 0 or 1;

$R^2$ is halogen, $C_1$-$C_3$ alkyl, $C_1$-$C_3$ alkyl substituted by one or more halogens, $C_1$-$C_3$ alkoxy, or $C_1$-$C_3$ alkoxy substituted by one or more halogens;

ring B is benzene ring or "5- to 6-membered heteroaromatic ring containing 1 or 2 heteroatoms independently selected from N, O and S";

k is 0 or 1;

$R^3$ is halogen, $C_1$-$C_3$ alkyl, $C_1$-$C_3$ alkyl substituted by one or more halogens, $C_1$-$C_3$ alkoxy, or $C_1$-$C_3$ alkoxy substituted by one or more halogens;

$R^A$ is

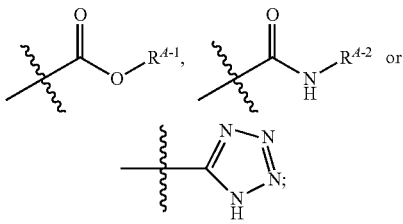

$R^A$-1 is hydrogen, or $C_1$-$C_3$ alkyl; $R^{A-2}$ is hydrogen or

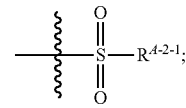

$R^{A-2-1}$ is $C_1$-$C_3$ alkyl.

In the present disclosure, the compound as shown in Formula I-A includes a tautomer form thereof, for example, the tautomer of

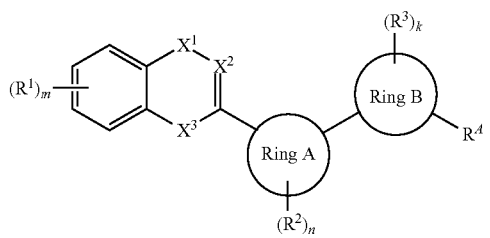

I-A is

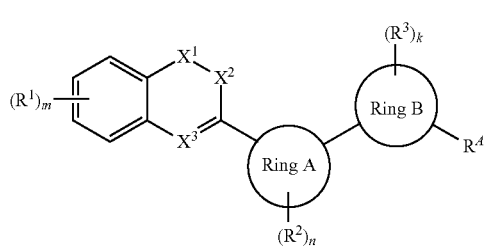

I-B for example, the tautomer of

[Structure: benzene ring fused with X¹=N, NH, with (R¹)ₘ substituent, connected to Ring A with (R²)ₙ, connected to Ring B with (R³)ₖ and R^A]

is

[Structure: tautomer with X¹-NH, N=, (R¹)ₘ, Ring A with (R²)ₙ, Ring B with (R³)ₖ and R^A].

In the present disclosure, the atoms in the compound as shown in formula I-A, the pharmaceutically acceptable salt thereof, the solvate thereof, the solvate of the pharmaceutically acceptable salt thereof can be present in their natural or unnatural abundance.

In an embodiment, in the compound as shown in formula I-A, the pharmaceutically acceptable salt thereof, the solvate thereof, the solvate of the pharmaceutically acceptable salt thereof or the crystal form thereof, some groups can be defined as follows, the other groups can be defined in any one of embodiments above:
when $R^1$ is halogen, then the halogen is fluorine, chlorine, bromine or iodine.

In an embodiment, in the compound as shown in formula I-A, the pharmaceutically acceptable salt thereof, the solvate thereof, the solvate of the pharmaceutically acceptable salt thereof or the crystal form thereof, some groups can be defined as follows, the other groups can be defined in any one of embodiments above:
when $R^1$ is halogen, then the halogen is fluorine, chlorine or bromine.

In an embodiment, in the compound as shown in formula I-A, the pharmaceutically acceptable salt thereof, the solvate thereof, the solvate of the pharmaceutically acceptable salt thereof or the crystal form thereof, some groups can be defined as follows, the other groups can be defined in any one of embodiments above:
when $R^1$ is halogen, then the halogen is fluorine or chlorine.

In an embodiment, in the compound as shown in formula I-A, the pharmaceutically acceptable salt thereof, the solvate thereof, the solvate of the pharmaceutically acceptable salt thereof or the crystal form thereof, some groups can be defined as follows, the other groups can be defined in any one of embodiments above:
when $R^1$ is halogen, then the halogen is chlorine.

In an embodiment, in the compound as shown in formula I-A, the pharmaceutically acceptable salt thereof, the solvate thereof, the solvate of the pharmaceutically acceptable salt thereof or the crystal form thereof, some groups can be defined as follows, the other groups can be defined in any one of embodiments above:
when $R^1$ is $C_1$-$C_3$ alkyl, then the $C_1$-$C_3$ alkyl is methyl.

In an embodiment, in the compound as shown in formula I-A, the pharmaceutically acceptable salt thereof, the solvate thereof, the solvate of the pharmaceutically acceptable salt thereof or the crystal form thereof, some groups can be defined as follows, the other groups can be defined in any one of embodiments above:
when $R^1$ is $C_1$-$C_3$ alkyl substituted by one or more halogens, then the halogen is fluorine, chlorine, bromine or iodine.

In an embodiment, in the compound as shown in formula I-A, the pharmaceutically acceptable salt thereof, the solvate thereof, the solvate of the pharmaceutically acceptable salt thereof or the crystal form thereof, some groups can be defined as follows, the other groups can be defined in any one of embodiments above:
when $R^1$ is $C_1$-$C_3$ alkyl substituted by one or more halogens, then the $C_1$-$C_3$ alkyl is methyl.

In an embodiment, in the compound as shown in formula I-A, the pharmaceutically acceptable salt thereof, the solvate thereof, the solvate of the pharmaceutically acceptable salt thereof or the crystal form thereof, some groups can be defined as follows, the other groups can be defined in any one of embodiments above:
when $R^1$ is $C_1$-$C_3$ alkyl substituted by one or more halogens, then the $C_1$-$C_3$ alkyl substituted by one or more halogens is trifluoromethyl.

In an embodiment, in the compound as shown in formula I-A, the pharmaceutically acceptable salt thereof, the solvate thereof, the solvate of the pharmaceutically acceptable salt thereof or the crystal form thereof, some groups can be defined as follows, the other groups can be defined in any one of embodiments above:
when $R^1$ is $C_1$-$C_3$ alkoxyl, then the $C_1$-$C_3$ alkoxyl is methoxyl.

In an embodiment, in the compound as shown in formula I-A, the pharmaceutically acceptable salt thereof, the solvate of the be defined as follows, the other groups can be defined in any one of embodiments above:
when $R^1$ is $C_1$-$C_3$ alkoxyl substituted by one or more halogens, then the halogen is fluorine, chlorine, bromine or iodine.

In an embodiment, in the compound as shown in formula I-A, the pharmaceutically acceptable salt thereof, the solvate thereof, the solvate of the pharmaceutically acceptable salt thereof or the crystal form thereof, some groups can be defined as follows, the other groups can be defined in any one of embodiments above:
when $R^1$ is $C_1$-$C_3$ alkoxyl substituted by one or more halogens, then the $C_1$-$C_3$ alkoxyl is methoxyl.

In an embodiment, in the compound as shown in formula I-A, the pharmaceutically acceptable salt thereof, the solvate thereof, the solvate of the pharmaceutically acceptable salt thereof or the crystal form thereof, some groups can be defined as follows, the other groups can be defined in any one of embodiments above:
when $R^1$ is $C_1$-$C_3$ alkoxyl substituted by one or more halogens, then the $C_1$-$C_3$ alkoxyl substituted by one or more halogens is trifluoromethoxyl.

In an embodiment, in the compound as shown in formula I-A, the pharmaceutically acceptable salt thereof, the solvate thereof, the solvate of the pharmaceutically acceptable salt thereof or the crystal form thereof, some groups can be defined as follows, the other groups can be defined in any one of embodiments above:
when m is 1 or 2, then $R^1$ is independently located in the ortho, meta or para position of $X^3$.

In an embodiment, in the compound as shown in formula I-A, the pharmaceutically acceptable salt thereof, the solvate thereof, the solvate of the pharmaceutically acceptable salt thereof or the crystal form thereof, some groups can be defined as follows, the other groups can be defined in any one of embodiments above:

when m is 1, then $R^1$ locates in the ortho or meta position of $X^3$.

In an embodiment, in the compound as shown in formula I-A, the pharmaceutically acceptable salt thereof, the solvate thereof, the solvate of the pharmaceutically acceptable salt thereof or the crystal form thereof, some groups can be defined as follows, the other groups can be defined in any one of embodiments above:

when m is 1, then $R^1$ locates in the ortho position of $X^3$.

In an embodiment, in the compound as shown in formula I-A, the pharmaceutically acceptable salt thereof, the solvate thereof, the solvate of the pharmaceutically acceptable salt thereof or the crystal form thereof, some groups can be defined as follows, the other groups can be defined in any one of embodiments above:

when $R^4$ is $C_1$-$C_3$ alkyl, then the $C_1$-$C_3$ alkyl is methyl or ethyl.

In an embodiment, in the compound as shown in formula I-A, the pharmaceutically acceptable salt thereof, the solvate thereof, the solvate of the pharmaceutically acceptable salt thereof or the crystal form thereof, some groups can be defined as follows, the other groups can be defined in any one of embodiments above:

when $R^4$ is $C_1$-$C_3$ alkyl, then the $C_1$-$C_3$ alkyl is methyl.

In an embodiment, in the compound as shown in formula I-A, the pharmaceutically acceptable salt thereof, the solvate thereof, the solvate of the pharmaceutically acceptable salt thereof or the crystal form thereof, some groups can be defined as follows, the other groups can be defined in any one of embodiments above:

when $R^4$ is $C_1$-$C_3$ alkyl substituted by one or more halogens, then the halogen is fluorine, chlorine, bromine or iodine.

In an embodiment, in the compound as shown in formula I-A, the pharmaceutically acceptable salt thereof, the solvate thereof, the solvate of the pharmaceutically acceptable salt thereof or the crystal form thereof, some groups can be defined as follows, the other groups can be defined in any one of embodiments above:

when $R^4$ is $C_1$-$C_3$ alkyl substituted by one or more halogens, then the $C_1$-$C_3$ alkyl is methyl.

In an embodiment, in the compound as shown in formula I-A, the pharmaceutically acceptable salt thereof, the solvate thereof, the solvate of the pharmaceutically acceptable salt thereof or the crystal form thereof, some groups can be defined as follows, the other groups can be defined in any one of embodiments above:

when $R^4$ is $C_1$-$C_3$ alkyl substituted by one or more halogens, then the $C_1$-$C_3$ alkyl substituted by one or more halogens is trifluoromethyl.

In an embodiment, in the compound as shown in formula I-A, the pharmaceutically acceptable salt thereof, the solvate thereof, the solvate of the be defined as follows, the other groups can be defined in any one of embodiments above:

when $R^4$ is $C_3$-$C_5$ cycloalkyl, then the $C_3$-$C_5$ cycloalkyl is cyclopropyl.

In an embodiment, in the compound as shown in formula I-A, the pharmaceutically acceptable salt thereof, the solvate thereof, the solvate of the pharmaceutically acceptable salt thereof or the crystal form thereof, some groups can be defined as follows, the other groups can be defined in any one of embodiments above:

when $R^5$ is $C_1$-$C_3$ alkyl, then the $C_1$-$C_3$ alkyl is methyl or ethyl.

In an embodiment, in the compound as shown in formula I-A, the pharmaceutically acceptable salt thereof, the solvate thereof, the solvate of the pharmaceutically acceptable salt thereof or the crystal form thereof, some groups can be defined as follows, the other groups can be defined in any one of embodiments above:

when $R^5$ is $C_1$-$C_3$ alkyl, then the $C_1$-$C_3$ alkyl is methyl.

In an embodiment, in the compound as shown in formula I-A, the pharmaceutically acceptable salt thereof, the solvate thereof, the solvate of the pharmaceutically acceptable salt thereof or the crystal form thereof, some groups can be defined as follows, the other groups can be defined in any one of embodiments above:

when $R^5$ is $C_1$-$C_3$ alkyl substituted by one or more halogens, then the halogen is fluorine, chlorine, bromine or iodine.

In an embodiment, in the compound as shown in formula I-A, the pharmaceutically acceptable salt thereof, the solvate thereof, the solvate of the pharmaceutically acceptable salt thereof or the crystal form thereof, some groups can be defined as follows, the other groups can be defined in any one of embodiments above:

when $R^5$ is $C_1$-$C_3$ alkyl substituted by one or more halogens, then the $C_1$-$C_3$ alkyl is methyl.

In an embodiment, in the compound as shown in formula I-A, the pharmaceutically acceptable salt thereof, the solvate thereof, the solvate of the pharmaceutically acceptable salt thereof or the crystal form thereof, some groups can be defined as follows, the other groups can be defined in any one of embodiments above:

when $R^5$ is $C_1$-$C_3$ alkyl substituted by one or more halogens, the $C_1$-$C_3$ alkyl substituted by one or more halogens is trifluoromethyl.

In an embodiment, in the compound as shown in formula I-A, the pharmaceutically acceptable salt thereof, the solvate thereof, the solvate of the pharmaceutically acceptable salt thereof or the crystal form thereof, some groups can be defined as follows, the other groups can be defined in any one of embodiments above:

when $R^5$ is $C_3$-$C_5$ cycloalkyl, then the $C_3$-$C_5$ cycloalkyl is cyclopropyl.

In an embodiment, in the compound as shown in formula I-A, the pharmaceutically acceptable salt thereof, the solvate thereof, the solvate of the pharmaceutically acceptable salt thereof or the crystal form thereof, some groups can be defined as follows, the other groups can be defined in any one of embodiments above:

when ring A is a "5-membered heteroaromatic ring containing 1, 2 or 3 heteroatoms independently selected from N, O and S", then the "5-membered heteroaromatic ring containing 1, 2 or 3 heteroatoms independently selected from N, O and S" is furan ring, pyrrole ring, oxazole ring, thiazole ring, imidazole ring or triazole ring.

In an embodiment, in the compound as shown in formula I-A, the pharmaceutically acceptable salt thereof, the solvate thereof, the solvate of the pharmaceutically acceptable salt thereof or the crystal form thereof, some groups can be defined as follows, the other groups can be defined in any one of embodiments above:

when ring A is a "5-membered heteroaromatic ring containing 1, 2 or 3 heteroatoms independently selected from N, O and S", then the "5-membered heteroaromatic ring containing 1, 2 or 3 heteroatoms independently selected from N O and S" is furan ring (for example

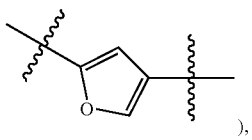 [SMILES: *c1coc(*)c1]

), pyrrole ring (for example

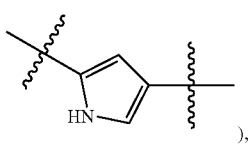

), or oxazole ring (for example

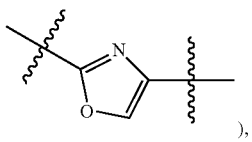 [SMILES: *c1coc(*)n1]

), thiazole ring (for example

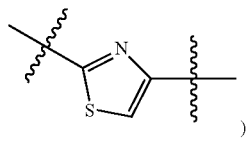 [SMILES: *c1csc(*)n1]

)

or imidazole ring (for example

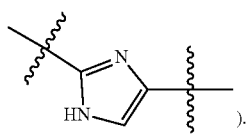 [SMILES: *c1c[nH]c(*)n1]

).

In an embodiment, in the compound as shown in formula I-A, the pharmaceutically acceptable salt thereof, the solvate thereof, the solvate of the pharmaceutically acceptable salt thereof or the crystal form thereof, some groups can be defined as follows, the other groups can be defined in any one of embodiments above:

when ring A is a "5-membered heteroaromatic ring containing 1, 2 or 3 heteroatoms independently selected from N, O and S", the "5-membered heteroaromatic ring containing 1, 2 or 3 heteroatoms independently selected from N O and S" is furan ring (for example

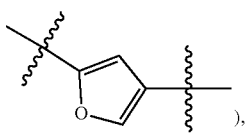 [SMILES: *c1coc(*)c1]

), oxazole ring (for example

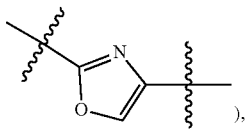 [SMILES: *c1coc(*)n1]

), thiazole ring (for example

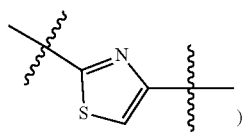 [SMILES: *c1csc(*)n1]

)

or imidazole ring (for example

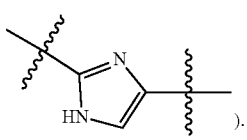 [SMILES: *c1c[nH]c(*)n1]

).

In an embodiment, in the compound as shown in formula I-A, the pharmaceutically acceptable salt thereof, the solvate thereof, the solvate of the pharmaceutically acceptable salt thereof or the crystal form thereof, some groups can be defined as follows, the other groups can be defined in any one of embodiments above:

when ring A is a "5-membered heteroaromatic ring containing 1, 2 or 3 heteroatoms independently selected from N, O and S", then the "5-membered heteroaromatic ring containing 1, 2 or 3 heteroatoms independently selected from N, O and S" is thiazole ring (for example

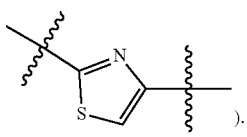 [SMILES: *c1csc(*)n1]

).

In an embodiment, in the compound as shown in formula I-A, the pharmaceutically acceptable salt thereof, the solvate thereof, the solvate of the pharmaceutically acceptable salt thereof or the crystal form thereof, some groups can be defined as follows, the other groups can be defined in any one of embodiments above:

[Structure diagram showing a bicyclic ring system with (R¹)ₘ substituent, X¹, X², X³ heteroatom positions]

locates in the meta position of ring B

In an embodiment, in the compound as shown in formula I-A, the pharmaceutically acceptable salt thereof, the solvate thereof, the solvate of the pharmaceutically acceptable salt thereof or the crystal form thereof, some groups can be defined as follows, the other groups can be defined in any one of embodiments above:

when $R^2$ is halogen, then the halogen is fluorine, chlorine, bromine or iodine.

In an embodiment, in the compound as shown in formula I-A, the pharmaceutically acceptable salt thereof, the solvate thereof, the solvate of the pharmaceutically acceptable salt thereof or the crystal form thereof, some groups can be defined as follows, the other groups can be defined in any one of embodiments above:

when $R^2$ is halogen, then the halogen is fluorine.

In an embodiment, in the compound as shown in formula I-A, the pharmaceutically acceptable salt thereof, the solvate thereof, the solvate of the pharmaceutically acceptable salt thereof or the crystal form thereof, some groups can be defined as follows, the other groups can be defined in any one of embodiments above:

when $R^2$ is $C_1$-$C_3$ alkyl, then the $C_1$-$C_3$ alkyl is methyl.

In an embodiment, in the compound as shown in formula I-A, the pharmaceutically acceptable salt thereof, the solvate thereof, the solvate of the pharmaceutically acceptable salt thereof or the crystal form thereof, some groups can be defined as follows, the other groups can be defined in any one of embodiments above:

when $R^2$ is $C_1$-$C_3$ alkyl substituted by one or more halogens, then the halogen is fluorine, chlorine, bromine or iodine.

In an embodiment, in the compound as shown in formula I-A, the pharmaceutically acceptable salt thereof, the solvate thereof, the solvate of the pharmaceutically acceptable salt thereof or the crystal form thereof, some groups can be defined as follows, the other groups can be defined in any one of embodiments above:

when $R^2$ is $C_1$-$C_3$ alkyl substituted by one or more halogens, then the $C_1$-$C_3$ alkyl is methyl.

In an embodiment, in the compound as shown in formula I-A, the pharmaceutically acceptable salt thereof, the solvate thereof, the solvate of the pharmaceutically acceptable salt thereof or the crystal form thereof, some groups can be defined as follows, the other groups can be defined in any one of embodiments above:

when $R^2$ is $C_1$-$C_3$ alkyl substituted by one or more halogens, then the $C_1$-$C_3$ alkyl substituted by one or more halogens is trifluoromethyl.

In an embodiment, in the compound as shown in formula I-A, the pharmaceutically acceptable salt thereof, the solvate thereof, the solvate of the pharmaceutically acceptable salt thereof or the crystal form thereof, some groups can be defined as follows, the other groups can be defined in any one of embodiments above:

when $R^2$ is $C_1$-$C_3$ alkoxyl, then the $C_1$-$C_3$ alkoxyl is methoxyl.

In an embodiment, in the compound as shown in formula I-A, the pharmaceutically acceptable salt thereof, the solvate thereof, the solvate of the pharmaceutically acceptable salt thereof or the crystal form thereof, some groups can be defined as follows, the other groups can be defined in any one of embodiments above:

when $R^2$ is $C_1$-$C_3$ alkoxyl substituted by one or more halogens, then the halogen is fluorine, chlorine, bromine or iodine.

In an embodiment, in the compound as shown in formula I-A, the pharmaceutically acceptable salt thereof, the solvate thereof, the solvate of the pharmaceutically acceptable salt thereof or the crystal form thereof, some groups can be defined as follows, the other groups can be defined in any one of embodiments above:

when $R^2$ is $C_1$-$C_3$ alkoxyl substituted by one or more halogens, then the $C_1$-$C_3$ alkoxyl is methoxyl.

In an embodiment, in the compound as shown in formula I-A, the pharmaceutically acceptable salt thereof, the solvate thereof, the solvate of the pharmaceutically acceptable salt thereof or the crystal form thereof, some groups can be defined as follows, the other groups can be defined in any one of embodiments above:

when $R^2$ is $C_1$-$C_3$ alkoxyl substituted by one or more halogens, then the $C_1$-$C_3$ alkoxyl substituted by one or more halogens is trifluoromethoxyl.

In an embodiment, in the compound as shown in formula I-A, the pharmaceutically acceptable salt thereof, the solvate thereof, the solvate of the pharmaceutically acceptable salt thereof or the crystal form thereof, some groups can be defined as follows, the other groups can be defined in any one of embodiments above:

when n is 1, then $R^2$ is independently located in the ortho, meta or para position of ring B.

In an embodiment, in the compound as shown in formula I-A, the pharmaceutically acceptable salt thereof, the solvate thereof, the solvate of the pharmaceutically acceptable salt thereof or the crystal form thereof, some groups can be defined as follows, the other groups can be defined in any one of embodiments above:

when n is 1, then $R^2$ is independently located in the meta position of ring B.

In an embodiment, in the compound as shown in formula I-A, the pharmaceutically acceptable salt thereof, the solvate thereof, the solvate of the pharmaceutically acceptable salt thereof or the crystal form thereof, some groups can be defined as follows, the other groups can be defined in any one of embodiments above:

when ring B is a "5- to 6-membered heteroaromatic ring containing 1 or 2 heteroatoms independently selected from N, O and S", then the "5- to 6-membered heteroaromatic ring containing 1 or 2 heteroatoms independently selected from N, O and S" is "5-membered heteroaromatic ring containing 1 or 2 heteroatoms independently selected from N, O and S".

In an embodiment, in the compound as shown in formula I-A, the pharmaceutically acceptable salt thereof, the solvate thereof, the solvate of the pharmaceutically acceptable salt thereof or the crystal form thereof, some groups can be defined as follows, the other groups can be defined in any one of embodiments above:

when ring B is a "5-membered heteroaromatic ring containing 1 or 2 heteroatoms independently selected from N, O and S", then the "5-membered heteroaromatic ring containing 1 or 2 heteroatoms independently selected from N, O and S" is furan ring, pyrrole ring, oxazole ring, thiazole ring or imidazole ring.

In an embodiment, in the compound as shown in formula I-A, the pharmaceutically acceptable salt thereof, the solvate thereof, the solvate of the pharmaceutically acceptable salt thereof or the crystal form thereof, some groups can be defined as follows, the other groups can be defined in any one of embodiments above:

when ring B is a "5- to 6-membered heteroaromatic ring containing 1 or 2 heteroatoms independently selected from N, O and S", then the "5- to 6-membered heteroaromatic ring containing 1 or 2 heteroatoms independently selected from N, O and S" is "6-membered heteroaromatic ring containing 1 or 2 heteroatoms independently selected from N, O and S".

In an embodiment, in the compound as shown in formula I-A, the pharmaceutically acceptable salt thereof, the solvate thereof, the solvate of the pharmaceutically acceptable salt thereof or the crystal form thereof, some groups can be defined as follows, the other groups can be defined in any one of embodiments above:

when ring B is a "6-membered heteroaromatic ring containing 1 or 2 heteroatoms independently selected from N, O and S", then the "6-membered heteroaromatic ring containing 1 or 2 heteroatoms independently selected from N, O and S" is pyridine ring or pyrimidine ring.

In an embodiment, in the compound as shown in formula I-A, the pharmaceutically acceptable salt thereof, the solvate thereof, the solvate of the be defined as follows, the other groups can be defined in any one of embodiments above:

when ring B is a "6-membered heteroaromatic ring containing 1 or 2 heteroatoms independently selected from N, O and S", then the "6-membered heteroaromatic ring containing 1 or 2 heteroatoms independently selected from N, O and S" is pyridine ring (for example

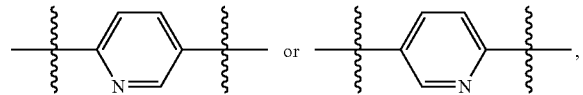

wherein, the left side is connected to ring A, and the right side is connected to $R^4$).

In an embodiment, in the compound as shown in formula I-A, the pharmaceutically acceptable salt thereof, the solvate thereof, the solvate of the pharmaceutically acceptable salt thereof or the crystal form thereof, some groups can be defined as follows, the other groups can be defined in any one of embodiments above:

when $R^3$ is halogen, then the halogen is fluorine, chlorine, bromine or iodine.

In an embodiment, in the compound as shown in formula I-A, the pharmaceutically acceptable salt thereof, the solvate thereof, the solvate of the pharmaceutically acceptable salt thereof or the crystal form thereof, some groups can be defined as follows, the other groups can be defined in any one of embodiments above:

when $R^3$ is halogen, then the halogen is fluorine.

In an embodiment, in the compound as shown in formula I-A, the pharmaceutically acceptable salt thereof, the solvate thereof, the solvate of the pharmaceutically acceptable salt thereof or the crystal form thereof, some groups can be defined as follows, the other groups can be defined in any one of embodiments above:

when $R^3$ is $C_1$-$C_3$ alkyl, then the $C_1$-$C_3$ alkyl is methyl.

In an embodiment, in the compound as shown in formula I-A, the pharmaceutically acceptable salt thereof, the solvate thereof, the solvate of the pharmaceutically acceptable salt thereof or the crystal form thereof, some groups can be defined as follows, the other groups can be defined in any one of embodiments above:

when $R^3$ is $C_1$-$C_3$ alkyl substituted by one or more halogens, then the halogen is fluorine, chlorine, bromine or iodine.

In an embodiment, in the compound as shown in formula I-A, the pharmaceutically acceptable salt thereof, the solvate thereof, the solvate of the be defined as follows, the other groups can be defined in any one of embodiments above:

when $R^3$ is $C_1$-$C_3$ alkyl substituted by one or more halogens, then the $C_1$-$C_3$ alkyl is methyl.

In an embodiment, in the compound as shown in formula I-A, the pharmaceutically acceptable salt thereof, the solvate thereof, the solvate of the pharmaceutically acceptable salt thereof or the crystal form thereof, some groups can be defined as follows, the other groups can be defined in any one of embodiments above:

when $R^3$ is $C_1$-$C_3$ alkyl substituted by one or more halogens, then the $C_1$-$C_3$ alkyl substituted by one or more halogens is trifluoromethyl.

In an embodiment, in the compound as shown in formula I-A, the pharmaceutically acceptable salt thereof, the solvate thereof, the solvate of the pharmaceutically acceptable salt thereof or the crystal form thereof, some groups can be defined as follows, the other groups can be defined in any one of embodiments above:

when $R^3$ is $C_1$-$C_3$ alkoxyl, then the $C_1$-$C_3$ alkoxyl is methoxyl.

In an embodiment, in the compound as shown in formula I-A, the pharmaceutically acceptable salt thereof, the solvate thereof, the solvate of the pharmaceutically acceptable salt thereof or the crystal form thereof, some groups can be defined as follows, the other groups can be defined in any one of embodiments above:

when $R^3$ is $C_1$-$C_3$ alkoxyl substituted by one or more halogens, then the halogen is fluorine, chlorine, bromine or iodine.

In an embodiment, in the compound as shown in formula I-A, the pharmaceutically acceptable salt thereof, the solvate thereof, the solvate of the pharmaceutically acceptable salt thereof or the crystal form thereof, some groups can be defined as follows, the other groups can be defined in any one of embodiments above:

when $R^3$ is $C_1$-$C_3$ alkoxyl substituted by one or more halogens, then the $C_1$-$C_3$ alkoxyl is methoxyl.

In an embodiment, in the compound as shown in formula I-A, the pharmaceutically acceptable salt thereof, the solvate thereof, the solvate of the pharmaceutically acceptable salt thereof or the crystal form thereof, some groups can be defined as follows, the other groups can be defined in any one of embodiments above:

when $R^3$ is $C_1$-$C_3$ alkoxyl substituted by one or more halogens, then the $C_1$-$C_3$ alkoxyl substituted by one or more halogens is trifluoromethoxyl.

In an embodiment, in the compound as shown in formula I-A, the pharmaceutically acceptable salt thereof, the solvate thereof, the solvate of the pharmaceutically acceptable salt thereof or the crystal form thereof, some groups can be defined as follows, the other groups can be defined in any one of embodiments above:

when k is 1, then $R^3$ is independently located in the ortho, meta or para position of ring A.

In an embodiment, in the compound as shown in formula I-A, the pharmaceutically acceptable salt thereof, the solvate thereof, the solvate of the pharmaceutically acceptable salt thereof or the crystal form thereof, some groups can be defined as follows, the other groups can be defined in any one of embodiments above:

when k is 1, then $R^3$ is independently located in the ortho or meta position of ring A.

In an embodiment, in the compound as shown in formula I-A, the pharmaceutically acceptable salt thereof, the solvate thereof, the solvate of the pharmaceutically acceptable salt thereof or the crystal form thereof, some groups can be defined as follows, the other groups can be defined in any one of embodiments above:

when $R^{4-1}$ is $C_1$-$C_3$ alkyl, then the $C_1$-$C_3$ alkyl is methyl or ethyl.

In an embodiment, in the compound as shown in formula I-A, the pharmaceutically acceptable salt thereof, the solvate thereof, the solvate of the pharmaceutically acceptable salt thereof or the crystal form thereof, some groups can be defined as follows, the other groups can be defined in any one of embodiments above:

when $R^{4-1}$ is $C_1$-$C_3$ alkyl, then the $C_1$-$C_3$ alkyl is ethyl.

In an embodiment, in the compound as shown in formula I-A, the pharmaceutically acceptable salt thereof, the solvate thereof, the solvate of the pharmaceutically acceptable salt thereof or the crystal form thereof, some groups can be defined as follows, the other groups can be defined in any one of embodiments above:

when $R^{4-2-1}$ is $C_1$-$C_3$ alkyl, then the $C_1$-$C_3$ alkyl is methyl.

In an embodiment, in the compound as shown in formula I-A, the pharmaceutically acceptable salt thereof, the solvate thereof, the solvate of the be defined as follows, the other groups can be defined in any one of embodiments above:

$R^4$ locates in the ortho, meta or para position of ring A.

In an embodiment, in the compound as shown in formula I-A, the pharmaceutically acceptable salt thereof, the solvate thereof, the solvate of the pharmaceutically acceptable salt thereof or the crystal form thereof, some groups can be defined as follows, the other groups can be defined in any one of embodiments above:

$R^4$ locates in the para position of ring A.

In an embodiment, in the compound as shown in formula I-A, the pharmaceutically acceptable salt thereof, the solvate thereof, the solvate of the pharmaceutically acceptable salt thereof or the crystal form thereof, some groups can be defined as follows, the other groups can be defined in any one of embodiments above:

m is 0 or 1.

In an embodiment, in the compound as shown in formula I-A, the pharmaceutically acceptable salt thereof, the solvate thereof, the solvate of the pharmaceutically acceptable salt thereof or the crystal form thereof, some groups can be defined as follows, the other groups can be defined in any one of embodiments above:

$R^1$ is halogen, $C_1$-$C_3$ alkyl substituted by one or more halogens, or $C_1$-$C_3$ alkoxy substituted by one or more halogens.

In an embodiment, in the compound as shown in formula I-A, the pharmaceutically acceptable salt thereof, the solvate thereof, the solvate of the pharmaceutically acceptable salt thereof or the crystal form thereof, some groups can be defined as follows, the other groups can be defined in any one of embodiments above:

$R^1$ is halogen or $C_1$-$C_3$ alkoxyl substituted by one or more halogens.

In an embodiment, in the compound as shown in formula I-A, the pharmaceutically acceptable salt thereof, the solvate thereof, the solvate of the pharmaceutically acceptable salt thereof or the crystal form thereof, some groups can be defined as follows, the other groups can be defined in any one of embodiments above:

$R^1$ is halogen, $C_1$-$C_3$ alkyl, or $C_1$-$C_3$ alkyl substituted by one or more halogens.

In an embodiment, in the compound as shown in formula I-A, the pharmaceutically acceptable salt thereof, the solvate thereof, the solvate of the be defined as follows, the other groups can be defined in any one of embodiments above:

$R^1$ is halogen or $C_1$-$C_3$ alkyl substituted by one or more halogens.

In an embodiment, in the compound as shown in formula I-A, the pharmaceutically acceptable salt thereof, the solvate thereof, the solvate of the pharmaceutically acceptable salt thereof or the crystal form thereof, some groups can be defined as follows, the other groups can be defined in any one of embodiments above:

$R^1$ is halogen.

In an embodiment, in the compound as shown in formula I-A, the pharmaceutically acceptable salt thereof, the solvate thereof, the solvate of the pharmaceutically acceptable salt thereof or the crystal form thereof, some groups can be defined as follows, the other groups can be defined in any one of embodiments above:

$X^1$ is —$C(R^4R^5)$—.

In an embodiment, in the compound as shown in formula I-A, the pharmaceutically acceptable salt thereof, the solvate thereof, the solvate of the pharmaceutically acceptable salt thereof or the crystal form thereof, some groups can be defined as follows, the other groups can be defined in any one of embodiments above:

when $X^1$ is —$C(R^4R^5)$—, then $R^4$ and $R^5$ are independently $C_1$-$C_3$ alkyl, $C_1$-$C_3$ alkyl substituted by one or more halogens, or $C_3$-$C_5$ cycloalkyl.

In an embodiment, in the compound as shown in formula I-A, the pharmaceutically acceptable salt thereof, the solvate thereof, the solvate of the pharmaceutically acceptable salt thereof or the crystal form thereof, some groups can be defined as follows, the other groups can be defined in any one of embodiments above:

when $X^1$ is —$C(R^4R^5)$—, then $R^4$ and $R^5$ are independently $C_1$-$C_3$ alkyl.

In an embodiment, in the compound as shown in formula I-A, the pharmaceutically acceptable salt thereof, the solvate thereof, the solvate of the pharmaceutically acceptable salt thereof or the crystal form thereof, some groups can be defined as follows, the other groups can be defined in any one of embodiments above:

when $X^1$ is —$C(R^4R^5)$—, then $R^4$ is $C_1$-$C_3$ alkyl; $R^5$ is hydrogen or $C_1$-$C_3$ alkyl.

In an embodiment, in the compound as shown in formula I-A, the pharmaceutically acceptable salt thereof, the solvate thereof, the solvate of the be defined as follows, the other groups can be defined in any one of embodiments above:

when $X^1$ is $$\begin{array}{c} X^{1-1} \\ \diagup\!\!\!\diagdown \end{array}$$

, then $X^{1-1}$ is single bond, O or $CH_2$.

In an embodiment, in the compound as shown in formula I-A, the pharmaceutically acceptable salt thereof, the solvate thereof, the solvate of the pharmaceutically acceptable salt thereof or the crystal form thereof, some groups can be defined as follows, the other groups can be defined in any one of embodiments above:

when $X^1$ is

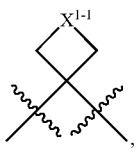

$X^{1-1}$ is single bond or O.

In an embodiment, in the compound as shown in formula I-A, the pharmaceutically acceptable salt thereof, the solvate thereof, the solvate of the pharmaceutically acceptable salt thereof or the crystal form thereof, some groups can be defined as follows, the other groups can be defined in any one of embodiments above:

$X^2$ is O or N.

In an embodiment, in the compound as shown in formula I-A, the pharmaceutically acceptable salt thereof, the solvate thereof, the solvate of the pharmaceutically acceptable salt thereof or the crystal form thereof, some groups can be defined as follows, the other groups can be defined in any one of embodiments above:

$X^2$ is O.

In an embodiment, in the compound as shown in formula I-A, the pharmaceutically acceptable salt thereof, the solvate thereof, the solvate of the pharmaceutically acceptable salt thereof or the crystal form thereof, some groups can be defined as follows, the other groups can be defined in any one of embodiments above:

$X^2$ is N.

In an embodiment, in the compound as shown in formula I-A, the pharmaceutically acceptable salt thereof, the solvate thereof, the solvate of the pharmaceutically acceptable salt thereof or the crystal form thereof, some groups can be defined as follows, the other groups can be defined in any one of embodiments above:

$X^3$ is O or NH.

In an embodiment, in the compound as shown in formula I-A, the pharmaceutically acceptable salt thereof, the solvate thereof, the solvate of the pharmaceutically acceptable salt thereof or the crystal form thereof, some groups can be defined as follows, the other groups can be defined in any one of embodiments above:

$X^3$ is NH.

In an embodiment, in the compound as shown in formula I-A, the pharmaceutically acceptable salt thereof, the solvate thereof, the solvate of the pharmaceutically acceptable salt thereof or the crystal form thereof, some groups can be defined as follows, the other groups can be defined in any one of embodiments above:

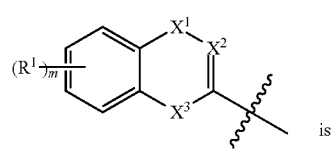 is

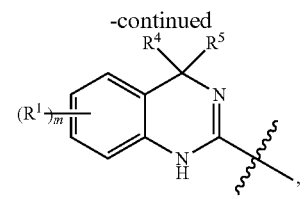

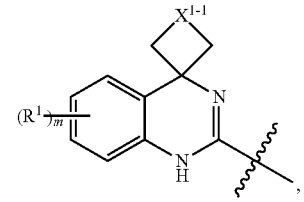

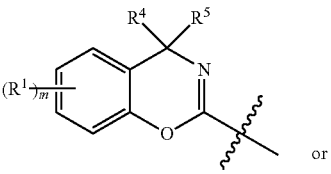

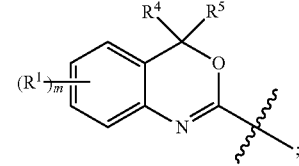

In an embodiment, in the compound as shown in formula I-A, the pharmaceutically acceptable salt thereof, the solvate thereof, the solvate of the pharmaceutically acceptable salt thereof or the crystal form thereof, some groups can be defined as follows, the other groups can be defined in any one of embodiments above:

n is 0.

In an embodiment, in the compound as shown in formula I-A, the pharmaceutically acceptable salt thereof, the solvate thereof, the solvate of the pharmaceutically acceptable salt thereof or the crystal form thereof, some groups can be defined as follows, the other groups can be defined in any one of embodiments above:

when n is 1, then $R^2$ is halogen, $C_1$-$C_3$ alkyl or $C_1$-$C_3$ alkoxyl.

In an embodiment, in the compound as shown in formula I-A, the pharmaceutically acceptable salt thereof, the solvate thereof, the solvate of the pharmaceutically acceptable salt thereof or the crystal form thereof, some groups can be defined as follows, the other groups can be defined in any one of embodiments above:

when n is 1, then $R^2$ is halogen.

In an embodiment, in the compound as shown in formula I-A, the pharmaceutically acceptable salt thereof, the solvate thereof, the solvate of the pharmaceutically acceptable salt thereof or the crystal form thereof, some groups can be defined as follows, the other groups can be defined in any one of embodiments above:

ring B is benzene ring or "6-membered heteroaromatic ring containing 1 or 2 heteroatoms independently selected from N, O and S";

In an embodiment, in the compound as shown in formula I-A, the pharmaceutically acceptable salt thereof, the solvate thereof, the solvate of the pharmaceutically acceptable salt thereof or the crystal form thereof, some groups can be defined as follows, the other groups can be defined in any one of embodiments above:

ring B is benzene ring.

In an embodiment, in the compound as shown in formula I-A, the pharmaceutically acceptable salt thereof, the solvate thereof, the solvate of the pharmaceutically acceptable salt thereof or the crystal form thereof, some groups can be defined as follows, the other groups can be defined in any one of embodiments above:

k is 0.

In an embodiment, in the compound as shown in formula I-A, the pharmaceutically acceptable salt thereof, the solvate thereof, the solvate of the pharmaceutically acceptable salt thereof or the crystal form thereof, some groups can be defined as follows, the other groups can be defined in any one of embodiments above:

when k is 1, then $R^3$ is halogen, $C_1$-$C_3$ alkyl or $C_1$-$C_3$ alkoxyl.

In an embodiment, in the compound as shown in formula I-A, the pharmaceutically acceptable salt thereof, the solvate thereof, the solvate of the pharmaceutically acceptable salt thereof or the crystal form thereof, some groups can be defined as follows, the other groups can be defined in any one of embodiments above:

when k is 1, then $R^3$ is halogen or $C_1$-$C_3$ alkoxyl.

In an embodiment, in the compound as shown in formula I-A, the pharmaceutically acceptable salt thereof, the solvate thereof, the solvate of the pharmaceutically acceptable salt thereof or the crystal form thereof, some groups can be defined as follows, the other groups can be defined in any one of embodiments above:

$R^A$ is

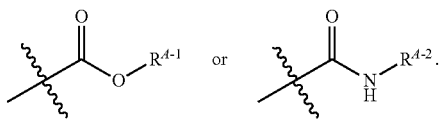

In an embodiment, in the compound as shown in formula I-A, the pharmaceutically acceptable salt thereof, the solvate thereof, the solvate of the pharmaceutically acceptable salt thereof or the crystal form thereof, some groups can be defined as follows, the other groups can be defined in any one of embodiments above:

$R^A$ is

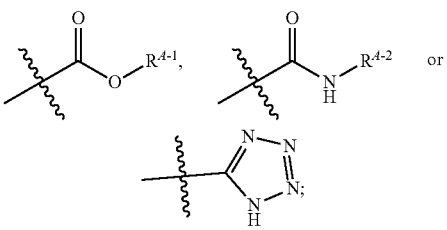

$R^{A-1}$ is $C_1$-$C_3$ alkyl; $R^{A-2}$ is hydrogen or

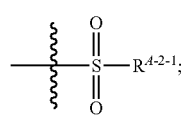

$R^{A-2-1}$ is $C_1$-$C_3$ alkyl.

In an embodiment, in the compound as shown in formula I-A, the pharmaceutically acceptable salt thereof, the solvate thereof, the solvate of the pharmaceutically acceptable salt thereof or the crystal form thereof, some groups can be defined as follows, the other groups can be defined in any one of embodiments above:

ring A is a "5-membered heteroaromatic ring containing 1, 2 or 3 heteroatoms independently selected from N, O and S";

ring B is benzene ring or "6-membered heteroaromatic ring containing 1 or 2 heteroatoms independently selected from N, O and S";

$R^A$ is

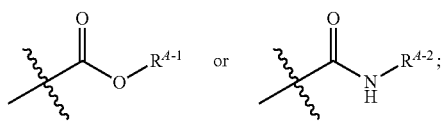

$R^A$ is located in the para position of ring A.

In an embodiment, in the compound as shown in formula I-A, the pharmaceutically acceptable salt thereof, the solvate thereof, the solvate of the pharmaceutically acceptable salt thereof or the crystal form thereof, some groups can be defined as follows, the other groups can be defined in any one of embodiments above:

ring A is furan ring, oxazole ring, thiazole ring or imidazole ring;

$R^1$ is fluorine, chlorine or trifluoromethoxyl;

m is 0, 1 or 2;

when m is 1, then $R^1$ is independently located in the ortho or para position of $X^3$.

when m is 2, then $R^1$ is independently located in the ortho or meta position of $X^3$.

ring B is benzene ring or "6-membered heteroaromatic ring containing 1 or 2 heteroatoms independently selected from N, O and S";

$R^A$ is

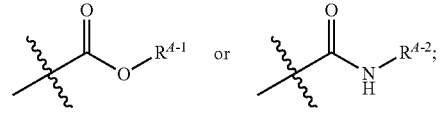

$R^A$ is located in the para position of ring A.

In an embodiment, in the compound as shown in formula I-A, the pharmaceutically acceptable salt thereof, the solvate thereof, the solvate of the pharmaceutically acceptable salt thereof or the crystal form thereof, some groups can be defined as follows, the other groups can be defined in any one of embodiments above:

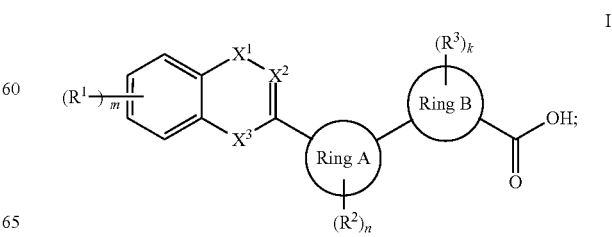

wherein, m is 0, 1 or 2;

$R^1$ is halogen, $C_1$-$C_3$ alkyl, $C_1$-$C_3$ alkyl substituted by one or more halogens, $C_1$-$C_3$ alkoxy, or $C_1$-$C_3$ alkoxy substituted by one or more halogens;

$X^1$ is —C($R^4R^5$)—, or

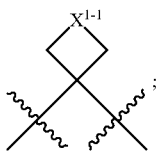

$R^4$ is $C_1$-$C_3$ alkyl, $C_1$-$C_3$ alkyl substituted by one or more halogens, or, $C_3$-$C_5$ cycloalkyl; $R^5$ is hydrogen, $C_1$-$C_3$ alkyl, $C_1$-$C_3$ alkyl substituted by one or more halogens, or, $C_3$-$C_5$ cycloalkyl; $X^{1-1}$ is a single bond, O, $CH_2$ or $CH_2CH_2$;

$X^2$ is N or CH;

$X^3$ is O, S, NH or $CH_2$;

ring A is a "5-membered heteroaromatic ring containing 1, 2 or 3 heteroatoms independently selected from N, O and S";

n is 0 or 1;

$R^2$ is halogen, $C_1$-$C_3$ alkyl, $C_1$-$C_3$ alkyl substituted by one or more halogens, $C_1$-$C_3$ alkoxy, or $C_1$-$C_3$ alkoxy substituted by one or more halogens;

ring B is benzene ring or "5- to 6-membered heteroaromatic ring containing 1 or 2 heteroatoms independently selected from N, O and S";

k is 0 or 1;

$R^3$ is halogen, $C_1$-$C_3$ alkyl, $C_1$-$C_3$ alkyl substituted by one or more halogens, $C_1$-$C_3$ alkoxy, or $C_1$-$C_3$ alkoxy substituted by one or more halogens.

In an embodiment, in the compound as shown in formula I, the pharmaceutically acceptable salt thereof, the solvate thereof, the solvate of the pharmaceutically acceptable salt thereof or the crystal form thereof, some groups can be defined as follows, the other groups can be defined in any one of embodiments above:

when $R^1$ is halogen, then the halogen is fluorine, chlorine, bromine or iodine.

In an embodiment, in the compound as shown in formula I, the pharmaceutically acceptable salt thereof, the solvate thereof, the solvate of the pharmaceutically acceptable salt thereof or the crystal form thereof, some groups can be defined as follows, the other groups can be defined in any one of embodiments above:

when $R^1$ is halogen, then the halogen is chlorine.

In an embodiment, in the compound as shown in formula I, the pharmaceutically acceptable salt thereof, the solvate thereof, the solvate of the pharmaceutically acceptable salt thereof or the crystal form thereof, some groups can be defined as follows, the other groups can be defined in any one of embodiments above:

when $R^1$ is $C_1$-$C_3$ alkyl, then the $C_1$-$C_3$ alkyl is methyl.

In an embodiment, in the compound as shown in formula I, the pharmaceutically acceptable salt thereof, the solvate thereof, the solvate of the pharmaceutically acceptable salt thereof or the crystal form thereof, some groups can be defined as follows, the other groups can be defined in any one of embodiments above:

when $R^1$ is $C_1$-$C_3$ alkyl substituted by one or more halogens, then the halogen is fluorine, chlorine, bromine or iodine.

In an embodiment, in the compound as shown in formula I, the pharmaceutically acceptable salt thereof, the solvate thereof, the solvate of the pharmaceutically acceptable salt thereof or the crystal form thereof, some groups can be defined as follows, the other groups can be defined in any one of embodiments above:

when $R^1$ is $C_1$-$C_3$ alkyl substituted by one or more halogens, then the $C_1$-$C_3$ alkyl is methyl.

In an embodiment, in the compound as shown in formula I, the pharmaceutically acceptable salt thereof, the solvate thereof, the solvate of the pharmaceutically acceptable salt thereof or the crystal form thereof, some groups can be defined as follows, the other groups can be defined in any one of embodiments above:

when $R^1$ is $C_1$-$C_3$ alkyl substituted by one or more halogens, then the $C_1$-$C_3$ alkyl substituted by one or more halogens is trifluoromethyl.

In an embodiment, in the compound as shown in formula I, the pharmaceutically acceptable salt thereof, the solvate thereof, the solvate of the pharmaceutically acceptable salt thereof or the crystal form thereof, some groups can be defined as follows, the other groups can be defined in any one of embodiments above:

when $R^1$ is $C_1$-$C_3$ alkoxyl, then the $C_1$-$C_3$ alkoxyl is methoxyl.

In an embodiment, in the compound as shown in formula I, the pharmaceutically acceptable salt thereof, the solvate thereof, the solvate of the pharmaceutically acceptable salt thereof or the crystal form thereof, some groups can be defined as follows, the other groups can be defined in any one of embodiments above:

when $R^1$ is $C_1$-$C_3$ alkoxyl substituted by one or more halogens, then the halogen is fluorine, chlorine, bromine or iodine.

In an embodiment, in the compound as shown in formula I, the pharmaceutically acceptable salt thereof, the solvate thereof, the solvate of the pharmaceutically acceptable salt thereof or the crystal form thereof, some groups can be defined as follows, the other groups can be defined in any one of embodiments above:

when $R^1$ is $C_1$-$C_3$ alkoxyl substituted by one or more halogens, then the $C_1$-$C_3$ alkoxyl is methoxyl.

In an embodiment, in the compound as shown in formula I, the pharmaceutically acceptable salt thereof, the solvate thereof, the solvate of the pharmaceutically acceptable salt thereof or the crystal form thereof, some groups can be defined as follows, the other groups can be defined in any one of embodiments above:

when $R^1$ is $C_1$-$C_3$ alkoxyl substituted by one or more halogens, then the $C_1$-$C_3$ alkoxyl substituted by one or more halogens is trifluoromethoxyl.

In an embodiment, in the compound as shown in formula I, the pharmaceutically acceptable salt thereof, the solvate thereof, the solvate of the be defined as follows, the other groups can be defined in any one of embodiments above:

when m is 1 or 2, then $R^1$ is independently located in the ortho, meta or para position of $X^3$.

In an embodiment, in the compound as shown in formula I, the pharmaceutically acceptable salt thereof, the solvate thereof, the solvate of the pharmaceutically acceptable salt thereof or the crystal form thereof, some groups can be defined as follows, the other groups can be defined in any one of embodiments above:

when m is 1, then $R^1$ locates in the ortho position of $X^3$.

In an embodiment, in the compound as shown in formula I, the pharmaceutically acceptable salt thereof, the solvate thereof, the solvate of the pharmaceutically acceptable salt thereof or the crystal form thereof, some groups can be defined as follows, the other groups can be defined in any one of embodiments above:

when $R^4$ is $C_1$-$C_3$ alkyl, then the $C_1$-$C_3$ alkyl is methyl.

In an embodiment, in the compound as shown in formula I, the pharmaceutically acceptable salt thereof, the solvate thereof, the solvate of the pharmaceutically acceptable salt thereof or the crystal form thereof, some groups can be defined as follows, the other groups can be defined in any one of embodiments above:

when $R^4$ is $C_1$-$C_3$ alkyl substituted by one or more halogens, then the halogen is fluorine, chlorine, bromine or iodine.

In an embodiment, in the compound as shown in formula I, the pharmaceutically acceptable salt thereof, the solvate thereof, the solvate of the pharmaceutically acceptable salt thereof or the crystal form thereof, some groups can be defined as follows, the other groups can be defined in any one of embodiments above:

when $R^4$ is $C_1$-$C_3$ alkyl substituted by one or more halogens, then the $C_1$-$C_3$ alkyl is methyl.

In an embodiment, in the compound as shown in formula I, the pharmaceutically acceptable salt thereof, the solvate thereof, the solvate of the pharmaceutically acceptable salt thereof or the crystal form thereof, some groups can be defined as follows, the other groups can be defined in any one of embodiments above:

When $R^4$ is $C_1$-$C_3$ alkyl substituted by one or more halogens, then the $C_1$-$C_3$ alkyl substituted by one or more halogens is trifluoromethyl.

In an embodiment, in the compound as shown in formula I, the pharmaceutically acceptable salt thereof, the solvate thereof, the solvate of the pharmaceutically acceptable salt thereof or the crystal form thereof, some groups can be defined as follows, the other groups can be defined in any one of embodiments above:

when $R^4$ is $C_3$-$C_5$ cycloalkyl, then the $C_3$-$C_5$ cycloalkyl is cyclopropyl.

In an embodiment, in the compound as shown in formula I, the pharmaceutically acceptable salt thereof, the solvate thereof, the solvate of the pharmaceutically acceptable salt thereof or the crystal form thereof, some groups can be defined as follows, the other groups can be defined in any one of embodiments above:

when $R^5$ is $C_1$-$C_3$ alkyl, then the $C_1$-$C_3$ alkyl is methyl.

In an embodiment, in the compound as shown in formula I, the pharmaceutically acceptable salt thereof, the solvate thereof, the solvate of the pharmaceutically acceptable salt thereof or the crystal form thereof, some groups can be defined as follows, the other groups can be defined in any one of embodiments above:

when $R^5$ is $C_1$-$C_3$ alkyl substituted by one or more halogens, then the halogen is fluorine, chlorine, bromine or iodine.

In an embodiment, in the compound as shown in formula I, the pharmaceutically acceptable salt thereof, the solvate thereof, the solvate of the pharmaceutically acceptable salt thereof or the crystal form thereof, some groups can be defined as follows, the other groups can be defined in any one of embodiments above:

when $R^5$ is $C_1$-$C_3$ alkyl substituted by one or more halogens, then the $C_1$-$C_3$ alkyl is methyl.

In an embodiment, in the compound as shown in formula I, the pharmaceutically acceptable salt thereof, the solvate thereof, the solvate of the pharmaceutically acceptable salt when $R^5$ is $C_1$-$C_3$ alkyl substituted by one or more halogens, then the $C_1$-$C_3$ alkyl substituted by one or more halogens is trifluoromethyl.

In an embodiment, in the compound as shown in formula I, the pharmaceutically acceptable salt thereof, the solvate thereof, the solvate of the be defined as follows, the other groups can be defined in any one of embodiments above:

when $R^5$ is $C_3$-$C_5$ cycloalkyl, then the $C_3$-$C_5$ cycloalkyl is cyclopropyl.

In an embodiment, in the compound as shown in formula I, the pharmaceutically acceptable salt thereof, the solvate thereof, the solvate of the pharmaceutically acceptable salt thereof or the crystal form thereof, some groups can be defined as follows, the other groups can be defined in any one of embodiments above:

when ring A is a "5-membered heteroaromatic ring containing 1, 2 or 3 heteroatoms independently selected from N, O and S", then the "5-membered heteroaromatic ring containing 1, 2 or 3 heteroatoms independently selected from N, O and S" is furan ring, pyrrole ring, oxazole ring, thiazole ring, imidazole ring or triazole ring.

In an embodiment, in the compound as shown in formula I, the pharmaceutically acceptable salt thereof, the solvate thereof, the solvate of the pharmaceutically acceptable salt thereof or the crystal form thereof, some groups can be defined as follows, the other groups can be defined in any one of embodiments above:

when ring A is a "5-membered heteroaromatic ring containing 1, 2 or 3 heteroatoms independently selected from N, O and S", then the "5-membered heteroaromatic ring containing 1, 2 or 3 heteroatoms independently selected from N, O and S" is thiazole ring.

In an embodiment, in the compound as shown in formula I, the pharmaceutically acceptable salt thereof, the solvate thereof, the solvate of the pharmaceutically acceptable salt thereof or the crystal form thereof, some groups can be defined as follows, the other groups can be defined in any one of embodiments above:

when $R^2$ is halogen, then the halogen is fluorine, chlorine, bromine or iodine.

In an embodiment, in the compound as shown in formula I, the pharmaceutically acceptable salt thereof, the solvate thereof, the solvate of the pharmaceutically acceptable salt thereof or the crystal form thereof, some groups can be defined as follows, the other groups can be defined in any one of embodiments above:

when $R^2$ is $C_1$-$C_3$ alkyl, then the $C_1$-$C_3$ alkyl is methyl.

In an embodiment, in the compound as shown in formula I, the pharmaceutically acceptable salt thereof, the solvate thereof, the solvate of the pharmaceutically acceptable salt thereof or the crystal form thereof, some groups can be defined as follows, the other groups can be defined in any one of embodiments above:

when $R^2$ is $C_1$-$C_3$ alkyl substituted by one or more halogens, then the halogen is fluorine, chlorine, bromine or iodine.

In an embodiment, in the compound as shown in formula I, the pharmaceutically acceptable salt thereof, the solvate thereof, the solvate of the pharmaceutically acceptable salt thereof or the crystal form thereof, some groups can be defined as follows, the other groups can be defined in any one of embodiments above:

when $R^2$ is $C_1$-$C_3$ alkyl substituted by one or more halogens, then the $C_1$-$C_3$ alkyl is methyl.

In an embodiment, in the compound as shown in formula I, the pharmaceutically acceptable salt thereof, the solvate thereof, the solvate of the pharmaceutically acceptable salt thereof or the crystal form thereof, some groups can be defined as follows, the other groups can be defined in any one of embodiments above:

when $R^2$ is $C_1$-$C_3$ alkyl substituted by one or more halogens, then the $C_1$-$C_3$ alkyl substituted by one or more halogens is trifluoromethyl.

In an embodiment, in the compound as shown in formula I, the pharmaceutically acceptable salt thereof, the solvate thereof, the solvate of the pharmaceutically acceptable salt thereof or the crystal form thereof, some groups can be defined as follows, the other groups can be defined in any one of embodiments above:

when $R^2$ is $C_1$-$C_3$ alkoxyl, then the $C_1$-$C_3$ alkoxyl is methoxyl.

In an embodiment, in the compound as shown in formula I, the pharmaceutically acceptable salt thereof, the solvate thereof, the solvate of the pharmaceutically acceptable salt thereof or the crystal form thereof, some groups can be defined as follows, the other groups can be defined in any one of embodiments above:

when $R^2$ is $C_1$-$C_3$ alkoxyl substituted by one or more halogens, then the halogen is fluorine, chlorine, bromine or iodine.

In an embodiment, in the compound as shown in formula I, the pharmaceutically acceptable salt thereof, the solvate thereof, the solvate of the pharmaceutically acceptable salt thereof or the crystal form thereof, some groups can be defined as follows, the other groups can be defined in any one of embodiments above:

when $R^2$ is $C_1$-$C_3$ alkoxyl substituted by one or more halogens, then the $C_1$-$C_3$ alkoxyl is methoxyl.

In an embodiment, in the compound as shown in formula I, the pharmaceutically acceptable salt thereof, the solvate thereof, the solvate of the pharmaceutically acceptable salt thereof or the crystal form thereof, some groups can be defined as follows, the other groups can be defined in any one of embodiments above:

when $R^2$ is $C_1$-$C_3$ alkoxyl substituted by one or more halogens, then the $C_1$-$C_3$ alkoxyl substituted by one or more halogens is trifluoromethoxyl.

In an embodiment, in the compound as shown in formula I, the pharmaceutically acceptable salt thereof, the solvate thereof, the solvate of the pharmaceutically acceptable salt thereof or the crystal form thereof, some groups can be defined as follows, the other groups can be defined in any one of embodiments above:

when n is 1, then $R^2$ is independently located in the ortho, meta or para position of ring B.

In an embodiment, in the compound as shown in formula I, the pharmaceutically acceptable salt thereof, the solvate thereof, the solvate of the pharmaceutically acceptable salt thereof or the crystal form thereof, some groups can be defined as follows, the other groups can be defined in any one of embodiments above:

when ring B is a "5- to 6-membered heteroaromatic ring containing 1 or 2 heteroatoms independently selected from N, O and S", then the "5- to 6-membered heteroaromatic ring containing 1 or 2 heteroatoms independently selected from N, O and S" is "5-membered heteroaromatic ring containing 1 or 2 heteroatoms independently selected from N, O and S".

In an embodiment, in the compound as shown in formula I, the pharmaceutically acceptable salt thereof, the solvate thereof, the solvate of the pharmaceutically acceptable salt thereof or the crystal form thereof, some groups can be defined as follows, the other groups can be defined in any one of embodiments above:

when ring B is a "5-membered heteroaromatic ring containing 1 or 2 heteroatoms independently selected from N, O and S", then the "5-membered heteroaromatic ring containing 1 or 2 heteroatoms independently selected from N, O and S" is furan ring, pyrrole ring, oxazole ring, thiazole ring or imidazole ring.

In an embodiment, in the compound as shown in formula I, the pharmaceutically acceptable salt thereof, the solvate thereof, the solvate of the pharmaceutically acceptable salt thereof or the crystal form thereof, some groups can be defined as follows, the other groups can be defined in any one of embodiments above:

when ring B is "5- to 6-membered heteroaromatic ring containing 1 or 2 heteroatoms independently selected from N, O and S", then the "5- to 6-membered heteroaromatic ring containing 1 or 2 heteroatoms independently selected from N, O and S" is "6-membered heteroaromatic ring containing 1 or 2 heteroatoms independently selected from N, O and S".

In an embodiment, in the compound as shown in formula I, the pharmaceutically acceptable salt thereof, the solvate thereof, the solvate of the pharmaceutically acceptable salt thereof or the crystal form thereof, some groups can be defined as follows, the other groups can be defined in any one of embodiments above:

when ring B is a "6-membered heteroaromatic ring containing 1 or 2 heteroatoms independently selected from N, O and S", then the "6-membered heteroaromatic ring containing 1 or 2 heteroatoms independently selected from N, O and S" is pyridine ring or pyrimidine ring.

In an embodiment, in the compound as shown in formula I, the pharmaceutically acceptable salt thereof, the solvate thereof, the solvate of the pharmaceutically acceptable salt thereof or the crystal form thereof, some groups can be defined as follows, the other groups can be defined in any one of embodiments above:

when $R^3$ is halogen, then the halogen is fluorine, chlorine, bromine or iodine.

In an embodiment, in the compound as shown in formula I, the pharmaceutically acceptable salt thereof, the solvate thereof, the solvate of the pharmaceutically acceptable salt thereof or the crystal form thereof, some groups can be defined as follows, the other groups can be defined in any one of embodiments above:

when $R^3$ is $C_1$-$C_3$ alkyl, then the $C_1$-$C_3$ alkyl is methyl.

In an embodiment, in the compound as shown in formula I, the pharmaceutically acceptable salt thereof, the solvate thereof, the solvate of the pharmaceutically acceptable salt thereof or the crystal form thereof, some groups can be defined as follows, the other groups can be defined in any one of embodiments above:

when $R^3$ is $C_1$-$C_3$ alkyl substituted by one or more halogens, then the halogen is fluorine, chlorine, bromine or iodine.

In an embodiment, in the compound as shown in formula I, the pharmaceutically acceptable salt thereof, the solvate thereof, the solvate of the pharmaceutically acceptable salt thereof or the crystal form thereof, some groups can be defined as follows, the other groups can be defined in any one of embodiments above:

when $R^3$ is $C_1$-$C_3$ alkyl substituted by one or more halogens, then the $C_1$-$C_3$ alkyl is methyl.

In an embodiment, in the compound as shown in formula I, the pharmaceutically acceptable salt thereof, the solvate thereof, the solvate of the pharmaceutically acceptable salt thereof or the crystal form thereof, some groups can be defined as follows, the other groups can be defined in any one of embodiments above:

when $R^3$ is $C_1$-$C_3$ alkyl substituted by one or more halogens, then the $C_1$-$C_3$ alkyl substituted by one or more halogens is trifluoromethyl.

In an embodiment, in the compound as shown in formula I, the pharmaceutically acceptable salt thereof, the solvate thereof, the solvate of the pharmaceutically acceptable salt thereof or the crystal form thereof, some groups can be defined as follows, the other groups can be defined in any one of embodiments above:

when $R^3$ is $C_1$-$C_3$ alkoxyl, then the $C_1$-$C_3$ alkoxyl is methoxyl.

In an embodiment, in the compound as shown in formula I, the pharmaceutically acceptable salt thereof, the solvate thereof, the solvate of the pharmaceutically acceptable salt thereof or the crystal form thereof, some groups can be defined as follows, the other groups can be defined in any one of embodiments above:

when $R^3$ is $C_1$-$C_3$ alkoxyl substituted by one or more halogens, then the halogen is fluorine, chlorine, bromine or iodine.

In an embodiment, in the compound as shown in formula I, the pharmaceutically acceptable salt thereof, the solvate thereof, the solvate of the pharmaceutically acceptable salt thereof or the crystal form thereof, some groups can be defined as follows, the other groups can be defined in any one of embodiments above:

when $R^3$ is $C_1$-$C_3$ alkoxyl substituted by one or more halogens, the $C_1$-$C_3$ alkoxyl is methoxyl.

In an embodiment, in the compound as shown in formula I, the pharmaceutically acceptable salt thereof, the solvate thereof, the solvate of the pharmaceutically acceptable salt thereof or the crystal form thereof, some groups can be defined as follows, the other groups can be defined in any one of embodiments above:

when $R^3$ is $C_1$-$C_3$ alkoxyl substituted by one or more halogens, the $C_1$-$C_3$ alkoxyl substituted by one or more halogens is trifluoromethoxyl.

In an embodiment, in the compound as shown in formula I, the pharmaceutically acceptable salt thereof, the solvate thereof, the solvate of the pharmaceutically acceptable salt thereof or the crystal form thereof, some groups can be defined as follows, the other groups can be defined in any one of embodiments above:

when k is 1, then $R^3$ is independently located in the ortho, meta or para position of ring A.

In an embodiment, in the compound as shown in formula I, the pharmaceutically acceptable salt thereof, the solvate thereof, the solvate of the pharmaceutically acceptable salt thereof or the crystal form thereof, some groups can be defined as follows, the other groups can be defined in any one of embodiments above:

the carboxyl at the right end of formula I locates in the ortho, meta or para position of ring A.

In an embodiment, in the compound as shown in formula I, the pharmaceutically acceptable salt thereof, the solvate thereof, the solvate of the pharmaceutically acceptable salt thereof or the crystal form thereof, some groups can be defined as follows, the other groups can be defined in any one of embodiments above:

the carboxyl at the right end of formula I locates in the para position of ring A.

In an embodiment, in the compound as shown in formula I, the pharmaceutically acceptable salt thereof, the solvate thereof, the solvate of the pharmaceutically acceptable salt thereof or the crystal form thereof, some groups can be defined as follows, the other groups can be defined in any one of embodiments above:

m is 0 or 1.

In an embodiment, in the compound as shown in formula I, the pharmaceutically acceptable salt thereof, the solvate thereof, the solvate of the be defined as follows, the other groups can be defined in any one of embodiments above:

$R^1$ is halogen, $C_1$-$C_3$ alkyl, or $C_1$-$C_3$ alkyl substituted by one or more halogens.

In an embodiment, in the compound as shown in formula I, the pharmaceutically acceptable salt thereof, the solvate thereof, the solvate of the pharmaceutically acceptable salt thereof or the crystal form thereof, some groups can be defined as follows, the other groups can be defined in any one of embodiments above:

$R^1$ is halogen or $C_1$-$C_3$ alkyl substituted by one or more halogens.

In an embodiment, in the compound as shown in formula I, the pharmaceutically acceptable salt thereof, the solvate thereof, the solvate of the pharmaceutically acceptable salt thereof or the crystal form thereof, some groups can be defined as follows, the other groups can be defined in any one of embodiments above:

$R^1$ is halogen.

In an embodiment, in the compound as shown in formula I, the pharmaceutically acceptable salt thereof, the solvate thereof, the solvate of the pharmaceutically acceptable salt thereof or the crystal form thereof, some groups can be defined as follows, the other groups can be defined in any one of embodiments above:

$X^1$ is —C($R^4R^5$)—.

In an embodiment, in the compound as shown in formula I, the pharmaceutically acceptable salt thereof, the solvate thereof, the solvate of the pharmaceutically acceptable salt thereof or the crystal form thereof, some groups can be defined as follows, the other groups can be defined in any one of embodiments above:

when $X^1$ is —C($R^4R^5$)—, then $R^4$ and $R^5$ are independently $C_1$-$C_3$ alkyl, $C_1$-$C_3$ alkyl substituted by one or more halogens, or $C_3$-$C_5$ cycloalkyl.

In an embodiment, in the compound as shown in formula I, the pharmaceutically acceptable salt thereof, the solvate thereof, the solvate of the pharmaceutically acceptable salt thereof or the crystal form thereof, some groups can be defined as follows, the other groups can be defined in any one of embodiments above:

when $X^1$ is —C($R^4R^5$)—, then $R^4$ and $R^5$ are independently $C_1$-$C_3$ alkyl.

In an embodiment, in the compound as shown in formula I, the pharmaceutically acceptable salt thereof, the solvate thereof, the solvate of the be defined as follows, the other groups can be defined in any one of embodiments above:

when $X^1$ is —C($R^4R^5$)—, then $R^4$ is $C_1$-$C_3$ alkyl; $R^5$ is hydrogen or $C_1$-$C_3$ alkyl.

In an embodiment, in the compound as shown in formula I, the pharmaceutically acceptable salt thereof, the solvate thereof, the solvate of the pharmaceutically acceptable salt thereof or the crystal form thereof, some groups can be defined as follows, the other groups can be defined in any one of embodiments above:

when $X^1$ is

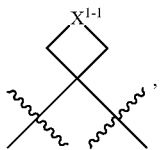

then $X^{1-1}$ is single bond, O or $CH_2$.

In an embodiment, in the compound as shown in formula I, the pharmaceutically acceptable salt thereof, the solvate thereof, the solvate of the pharmaceutically acceptable salt thereof or the crystal form thereof, some groups can be defined as follows, the other groups can be defined in any one of embodiments above:

$X^2$ is N.

In an embodiment, in the compound as shown in formula I, the pharmaceutically acceptable salt thereof, the solvate thereof, the solvate of the pharmaceutically acceptable salt thereof or the crystal form thereof, some groups can be defined as follows, the other groups can be defined in any one of embodiments above:

$X^3$ is NH.

In an embodiment, in the compound as shown in formula I, the pharmaceutically acceptable salt thereof, the solvate thereof, the solvate of the pharmaceutically acceptable salt thereof or the crystal form thereof, some groups can be defined as follows, the other groups can be defined in any one of embodiments above:

n is 0.

In an embodiment, in the compound as shown in formula I, the pharmaceutically acceptable salt thereof, the solvate thereof, the solvate of the pharmaceutically acceptable salt thereof or the crystal form thereof, some groups can be defined as follows, the other groups can be defined in any one of embodiments above:

when n is 1, then $R^2$ is halogen, $C_1$-$C_3$ alkyl or $C_1$-$C_3$ alkoxyl.

In an embodiment, in the compound as shown in formula I, the pharmaceutically acceptable salt thereof, the solvate thereof, the solvate of the be defined as follows, the other groups can be defined in any one of embodiments above:

ring B is benzene ring.

In an embodiment, in the compound as shown in formula I, the pharmaceutically acceptable salt thereof, the solvate thereof, the solvate of the pharmaceutically acceptable salt thereof or the crystal form thereof, some groups can be defined as follows, the other groups can be defined in any one of embodiments above:

k is 0.

In an embodiment, in the compound as shown in formula I, the pharmaceutically acceptable salt thereof, the solvate thereof, the solvate of the pharmaceutically acceptable salt thereof or the crystal form thereof, some groups can be defined as follows, the other groups can be defined in any one of embodiments above:

when k is 1, then $R^3$ is halogen, $C_1$-$C_3$ alkyl or $C_1$-$C_3$ alkoxyl.

In an embodiment, in the compound as shown in formula I, the pharmaceutically acceptable salt thereof, the solvate thereof, the solvate of the pharmaceutically acceptable salt thereof or the crystal form thereof, some groups can be defined as follows, the other groups can be defined in any one of embodiments above:

m is 0, 1 or 2;

$R^1$ is halogen, $C_1$-$C_3$ alkyl, $C_1$-$C_3$ alkyl substituted by one or more halogens, $C_1$-$C_3$ alkoxy, or $C_1$-$C_3$ alkoxy substituted by one or more halogens;

$X^1$ is —$C(R^4R^5)$—, or

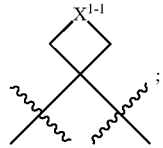

$R^4$ is $C_1$-$C_3$ alkyl, $C_1$-$C_3$ alkyl substituted by one or more halogens, or, $C_3$-$C_5$ cycloalkyl; $R^5$ is hydrogen, $C_1$-$C_3$ alkyl, $C_1$-$C_3$ alkyl substituted by one or more halogens, or, $C_3$-$C_5$ cycloalkyl; $X^{1-1}$ is a single bond, O, $CH_2$ or $CH_2CH_2$;

$X^2$ is N;

$X^3$ is NH;

ring A is a "5-membered heteroaromatic ring containing 1, 2 or 3 heteroatoms independently selected from N, O and S";

n is 0 or 1;

$R^2$ is halogen, $C_1$-$C_3$ alkyl, $C_1$-$C_3$ alkyl substituted by one or more halogens, $C_1$-$C_3$ alkoxy, or $C_1$-$C_3$ alkoxy substituted by one or more halogens;

ring B is benzene ring or "5- to 6-membered heteroaromatic ring containing 1 or 2 heteroatoms independently selected from N, O and S";

k is 0 or 1;

$R^3$ is halogen, $C_1$-$C_3$ alkyl, $C_1$-$C_3$ alkyl substituted by one or more halogens, $C_1$-$C_3$ alkoxy, or $C_1$-$C_3$ alkoxy substituted by one or more halogens.

In an embodiment, in the compound as shown in formula I, the pharmaceutically acceptable salt thereof, the solvate thereof, the solvate of the pharmaceutically acceptable salt thereof or the crystal form thereof, some groups can be defined as follows, the other groups can be defined in any one of embodiments above:

m is 0, 1 or 2;

$R^1$ is halogen, $C_1$-$C_3$ alkyl, or $C_1$-$C_3$ alkyl substituted by one or more halogens;

$X^1$ is —$C(R^4R^5)$—, or

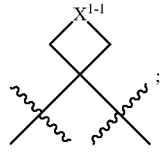

$R^4$ and $R^5$ are independently $C_1$-$C_3$ alkyl, $C_1$-$C_3$ alkyl substituted by one or more halogens, or $C_3$-$C_5$ cycloalkyl; $X^{1-1}$ is single bond, O or $CH_2$.

$X^2$ is N;

$X^3$ is NH;

ring A is a "5-membered heteroaromatic ring containing 1, 2 or 3 heteroatoms independently selected from N, O and S";

n is 0 or 1;

$R^2$ is halogen, $C_1$-$C_3$ alkyl or $C_1$-$C_3$ alkoxyl;

ring B is benzene ring or "5- to 6-membered heteroaromatic ring containing 1 or 2 heteroatoms independently selected from N, O and S";

k is 0 or 1;

$R^3$ is halogen, $C_1$-$C_3$ alkyl or $C_1$-$C_3$ alkoxyl.

In an embodiment, in the compound as shown in formula I, the pharmaceutically acceptable salt thereof, the solvate thereof, the solvate of the pharmaceutically acceptable salt thereof or the crystal form thereof, some groups can be defined as follows, the other groups can be defined in any one of embodiments above:

m is 0, 1 or 2;

$R^1$ is halogen or $C_1$-$C_3$ alkyl substituted by one or more halogens.

$X^1$ is —C($R^4R^5$)—;

$R^4$ and $R^5$ are independently $C_{1-3}$ alkyl;

$X^2$ is N;

$X^3$ is NH;

ring A is a "5-membered heteroaromatic ring containing 1, 2 or 3 heteroatoms independently selected from N, O and S";

n is 0 or 1;

$R^2$ is halogen, $C_1$-$C_3$ alkyl or $C_1$-$C_3$ alkoxyl;

ring B is benzene ring;

k is 0 or 1;

$R^3$ is halogen, $C_1$-$C_3$ alkyl or $C_1$-$C_3$ alkoxyl.

In an embodiment, in the compound as shown in formula I, the pharmaceutically acceptable salt thereof, the solvate thereof, the solvate of the pharmaceutically acceptable salt thereof or the crystal form thereof, some groups can be defined as follows, the other groups can be defined in any one of embodiments above:

m is 0 or 1;

$R^1$ is halogen;

$X^1$ is —C($R^4R^5$)—;

$R^4$ is $C_1$-$C_3$ alkyl; $R^5$ is hydrogen or $C_1$-$C_3$ alkyl;

$X^2$ is N;

$X^3$ is NH;

ring A is a "5-membered heteroaromatic ring containing 1, 2 or 3 heteroatoms independently selected from N, O and S";

n is 0;

ring B is benzene ring;

k is 0.

In an embodiment, in the compound as shown in formula I-A, the pharmaceutically acceptable salt thereof, the solvate thereof, the solvate of the pharmaceutically acceptable salt thereof or the crystal form thereof, some groups can be defined as follows, the other groups can be defined in any one of embodiments above:

I-1

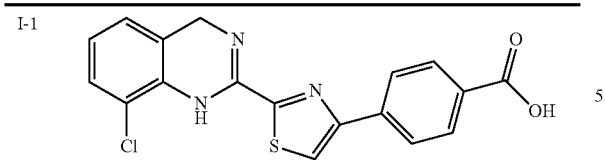

I-2

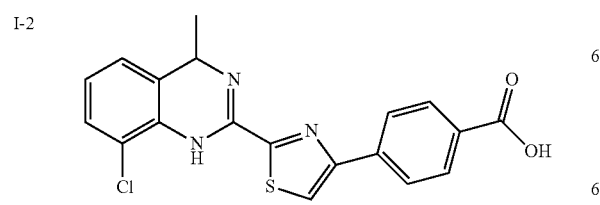

-continued

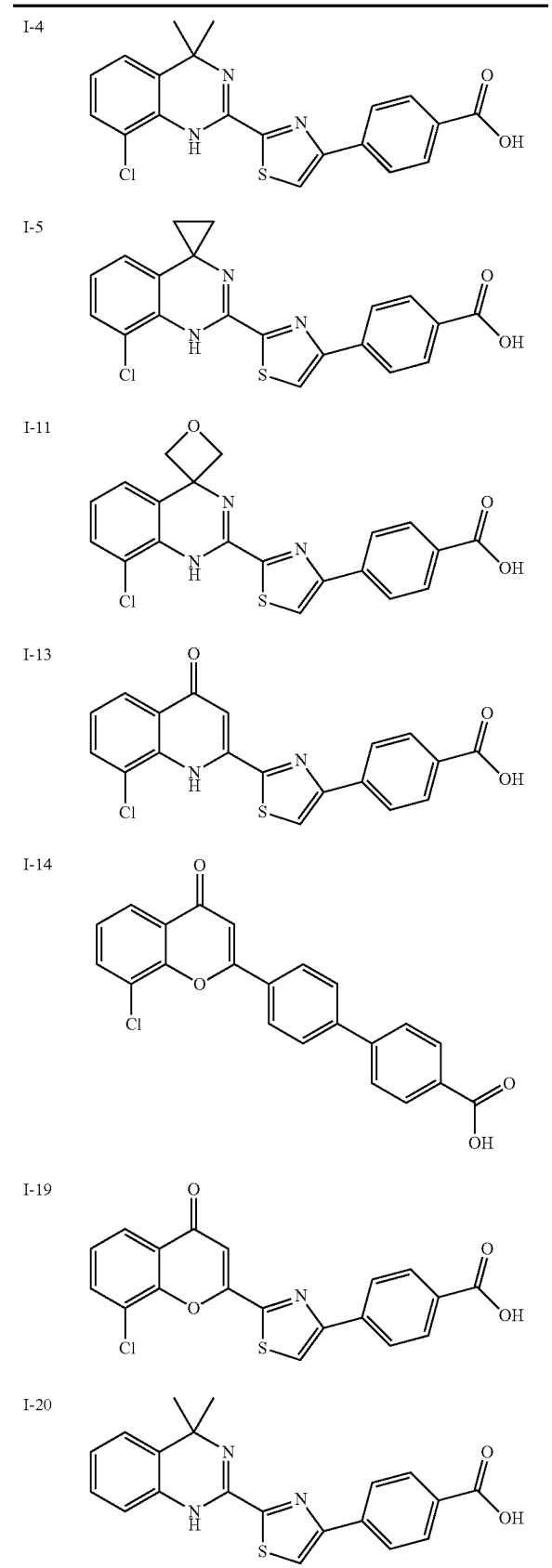

-continued
I-21
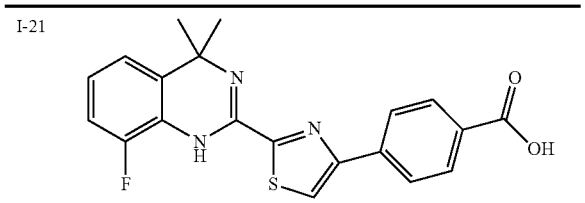
I-22
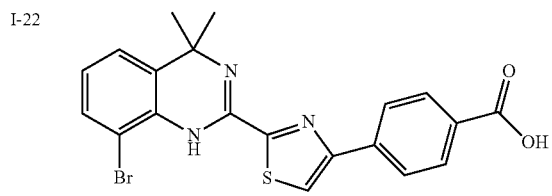
I-23
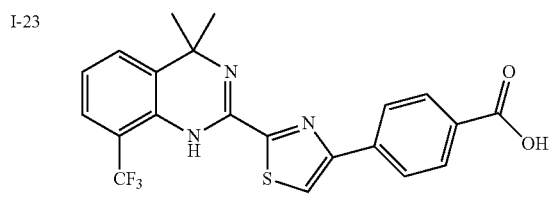
I-25
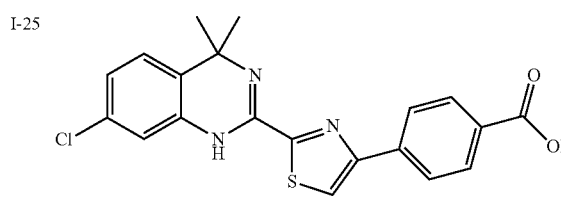
I-27
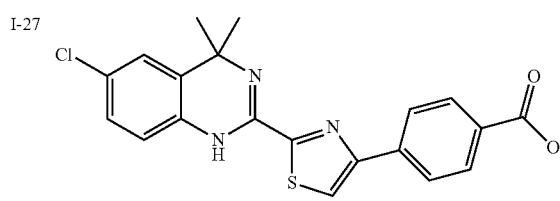
I-34
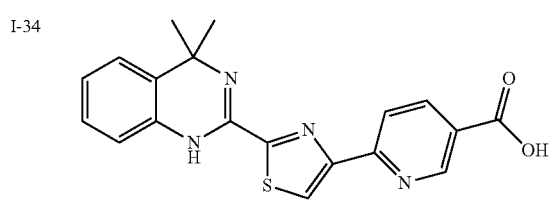
I-35
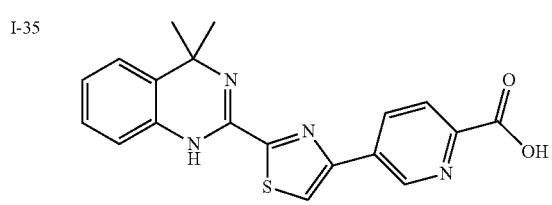
I-36
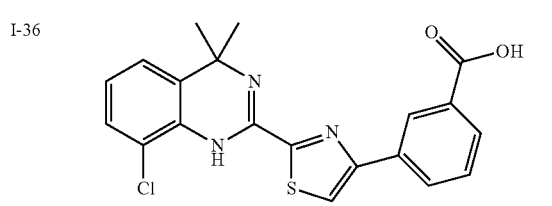
-continued
I-38
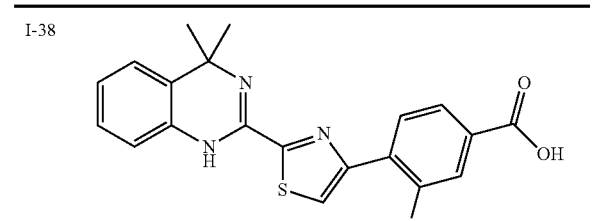
I-40
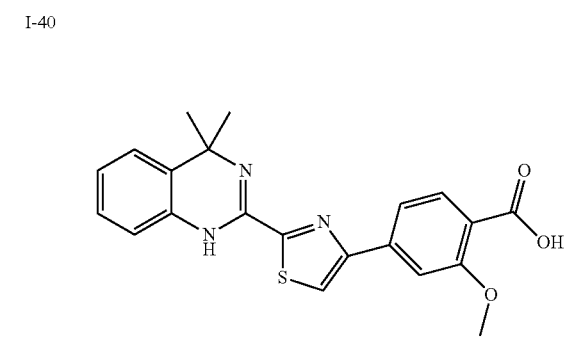
I-43
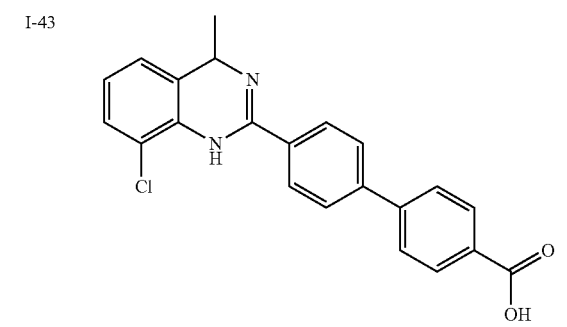
I-46
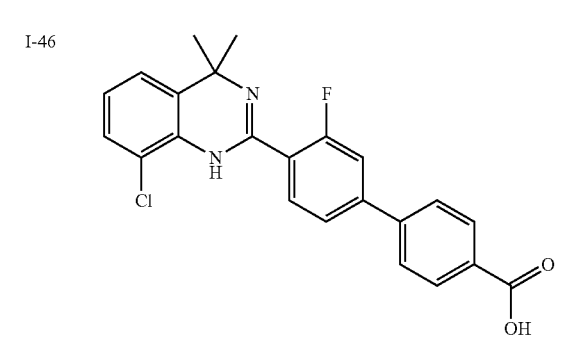
I-48
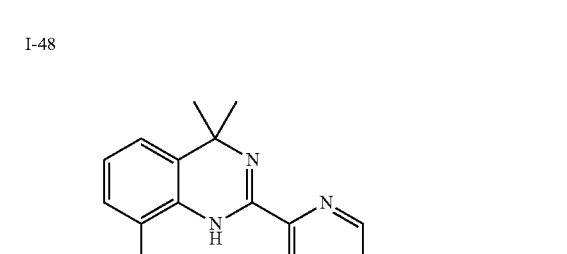
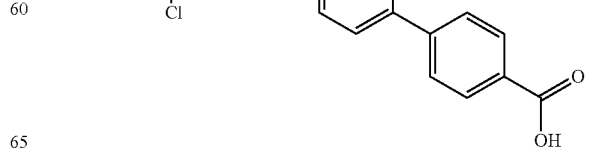

I-49 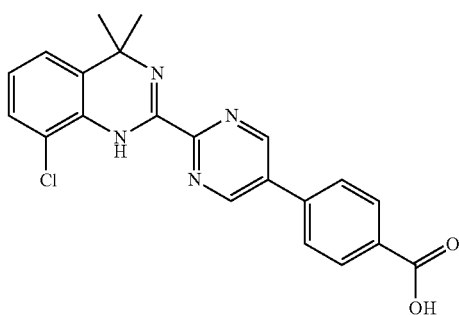 [SMILES: CC1(C)N=C(c2ncc(-c3ccc(C(=O)O)cc3)cn2)Nc2c(Cl)cccc21]

I-50 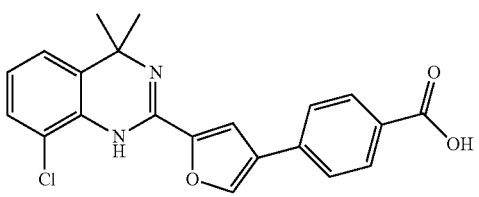 [SMILES: CC1(C)N=C(c2cc(-c3ccc(C(=O)O)cc3)co2)Nc2c(Cl)cccc21]

I-51 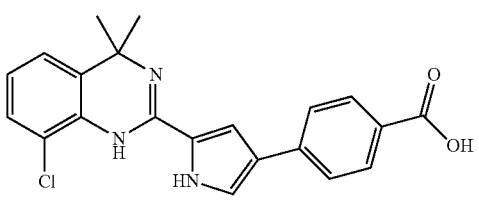 [SMILES: CC1(C)N=C(c2cc(-c3ccc(C(=O)O)cc3)c[nH]2)Nc2c(Cl)cccc21]

I-53 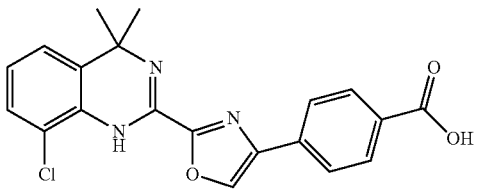

I-54 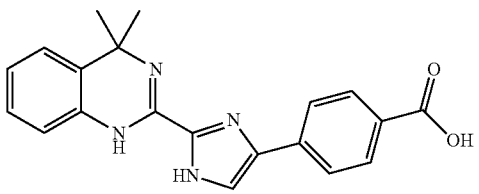

I-65 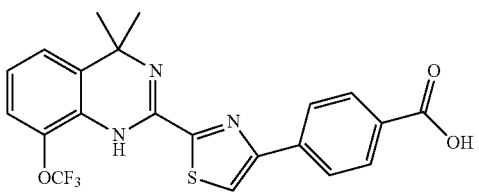 [SMILES: CC1(C)N=C(c2nc(-c3ccc(C(=O)O)cc3)co2)Nc2c(Cl)cccc21]

I-66 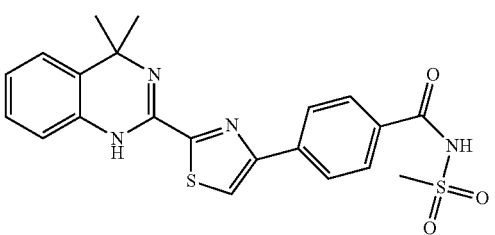 [SMILES: CC1(C)N=C(c2nc(-c3ccc(C(=O)NS(C)(=O)=O)cc3)cs2)Nc2ccccc21]

I-67 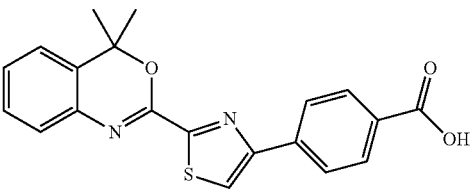 [SMILES: CC1(C)OC(c2nc(-c3ccc(C(=O)O)cc3)cs2)=Nc2ccccc21]

I-68 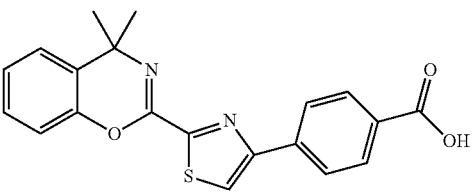 [SMILES: CC1(C)N=C(c2nc(-c3ccc(C(=O)O)cc3)cs2)Oc2ccccc21]

I-69 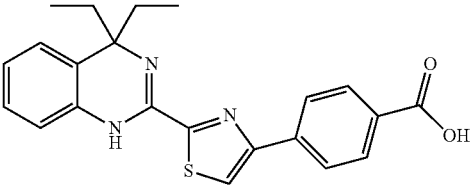 [SMILES: CCC1(CC)N=C(c2nc(-c3ccc(C(=O)O)cc3)cs2)Nc2ccccc21]

I-70 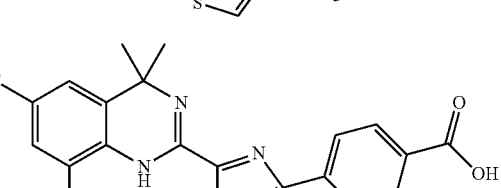

I-71 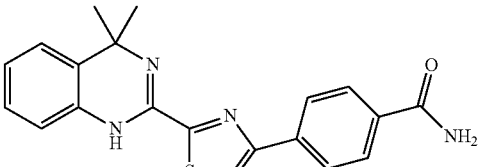

I-72 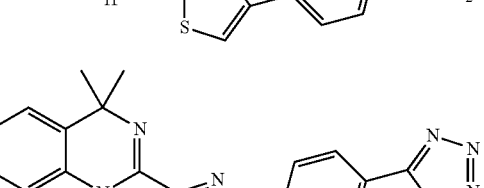

I-73 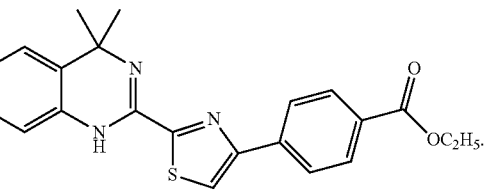

The present disclosure further provides a pharmaceutical composition comprising a substance X and a pharmaceutical excipient;

the substance X is the compound as shown in formula I-A, the pharmaceutically acceptable salt thereof, the solvate thereof, the solvate of the pharmaceutically acceptable salt thereof or the crystal form thereof.

The pharmaceutical composition can consist of the substance X and the pharmaceutical excipients.

The present disclosure further provides a use of the substance X in the preparation of a medicament;

the substance X is the compound as shown in formula I-A, the pharmaceutically acceptable salt thereof, the solvate thereof, the solvate of the pharmaceutically acceptable salt thereof or the crystal form thereof.

The medicament can be used to reduce the level of a marker; the marker is one or more of HBsAg, HBeAg and HBV DNA.

The medicament can be used for the treatment and/or prevention of hepatitis B.

The present disclosure further provides a method for the treatment and/or prevention of Hepatitis B, comprising administering an effective amount of the substance X to a subject; the substance X is the compound as shown in formula I-A, the pharmaceutically acceptable salt thereof, the solvate thereof, the solvate of the pharmaceutically acceptable salt thereof or the crystal form thereof.

The present disclosure further provides a pharmaceutical combination comprising the substance X and other medicaments for the prevention and/or treatment of hepatitis B;

the substance X is the compound as shown in formula I-A, the pharmaceutically acceptable salt thereof, the solvate thereof, the solvate of the pharmaceutically acceptable salt thereof or the crystal form thereof.

The "other medicaments for the prevention and/or treatment of hepatitis B" refers to the medicament for the prevention and/or treatment of hepatitis B other than the substance X.

The "other medicament for the prevention and/or treatment of hepatitis B" may be one or more of HBV-DNA polymerase inhibitors, interferons, HBV adsorption invasive inhibitors, RNA inhibitors, HBsAg generation and secretion inhibitors, nucleocapsid protein inhibitors, cccDNA inhibitors, HBV preventive and therapeutic vaccines, HBV antibodies, RNaseH inhibitors, viral maturation inhibitors and immunomodulators.

The present disclosure also provides a use of the substance X in the preparation of a medicament; the medicament is used in combination with other medicaments for the prevention and/or treatment of hepatitis B;

the substance X is the compound as shown in formula I-A, the pharmaceutically acceptable salt thereof, the solvate thereof, the solvate of the pharmaceutically acceptable salt thereof or the crystal form thereof.

The medicament can be used to reduce the level of a marker; the marker is one or more of HBsAg, HBeAg and HBV DNA.

The medicament can be used for the treatment and/or prevention of hepatitis B.

The "other medicament for the prevention and/or treatment of hepatitis B" refers to the medicament for the prevention and/or treatment of hepatitis B other than the substance X.

The "other medicament for the prevention and/or treatment of hepatitis B" may be one or more of HBV-DNA polymerase inhibitors, interferons, HBV adsorption invasive inhibitors, RNA inhibitors, HBsAg generation and secretion inhibitors, nucleocapsid protein inhibitors, cccDNA inhibitors, HBV preventive and therapeutic vaccines, HBV antibodies, RNaseH inhibitors, viral maturation inhibitors and immunomodulators.

The present disclosure further provides a use of the other medicament for the prevention and/or treatment of hepatitis B in the preparation of a medicament, the medicament is used in combination with the substance X;

the substance X is the compound as shown in formula I-A, the pharmaceutically acceptable salt thereof, the solvate thereof, the solvate of the pharmaceutically acceptable salt thereof or the crystal form thereof.

The "other medicament for the prevention and/or treatment of hepatitis B" refers to the medicament for the prevention and/or treatment of hepatitis B other than the substance X.

The "other medicament for the prevention and/or treatment of hepatitis B" may be one or more of HBV-DNA polymerase inhibitors, interferons, HBV adsorption invasive inhibitors, RNA inhibitors, HBsAg generation and secretion inhibitors, nucleocapsid protein inhibitors, cccDNA inhibitors, HBV preventive and therapeutic vaccines, HBV antibodies, RNaseH inhibitors, viral maturation inhibitors and immunomodulators.

The medicament can be used for the treatment and/or prevention of hepatitis B.

The present disclosure further provides a method for the treatment and/or prevention of Hepatitis B, comprising administering an effective amount of the substance X and other medicaments used for the prevention and/or treatment of hepatitis B to a subject; the substance X is the compound as shown in formula I-A, the pharmaceutically acceptable salt thereof, the solvate thereof, the solvate of the pharmaceutically acceptable salt thereof or the crystal form thereof.

The "other medicament for the prevention and/or treatment of hepatitis B" refers to the medicament for the prevention and/or treatment of hepatitis B other than the substance X.

The "other medicament for the prevention and/or treatment of hepatitis B" may be one or more of HBV-DNA polymerase inhibitors, interferons, HBV adsorption invasive inhibitors, RNA inhibitors, HBsAg generation and secretion inhibitors, nucleocapsid protein inhibitors, cccDNA inhibitors, HBV preventive and therapeutic vaccines, HBV antibodies, RNaseH inhibitors, viral maturation inhibitors and immunomodulators.

Unless otherwise specified, the terms used in the present disclosure have the following meanings:

The term "more" refers to two, three, four or five.

The term "pharmaceutically acceptable" refers to that the salt, solvent and excipient are generally non-toxic, safe and suitable for patients. The "patient" is preferably a mammal, more preferably a human.

The term "pharmaceutically acceptable salt" refers to a salt prepared from a compound of the present disclosure and a relatively non-toxic and pharmaceutically acceptable acid or base. When the compound of the present disclosure contains a relatively acidic functional group, then a base addition salt can be obtained by bringing the neutral form of the compound into contact with a sufficient amount of pharmaceutically acceptable base in a pure solution or a suitable inert solvent. The pharmaceutically acceptable base addition salts include, but are not limited to: lithium salt, sodium salt, potassium salt, calcium salt, aluminum salt, magnesium salt, zinc salt, bismuth salt, ammonium salt, and diethanolamine salt. When the compound of the present disclosure contains a relatively basic functional group, then an acid addition salt can be obtained by bringing the neutral form of the compound into contact with a sufficient amount of pharmaceutically acceptable acid in a pure solution or a suitable inert solvent. The pharmaceutically acceptable acids include inorganic acids, and the inorganic acids include, but are not limited to: hydrochloric acid, hydrobromic acid, hydroiodic acid, nitric acid, carbonic acid, phosphoric acid, phosphorous acid, sulfuric acid, and the like. The pharmaceutically acceptable acids include organic acids, and the organic acids include, but are not limited to: acetic acid, propionic acid, oxalic acid, isobutyric acid, maleic acid, malonic acid, benzoic acid, succinic acid, suberic acid, fumaric acid, lactic acid, mandelic acid, phthalic acid, benzenesulfonic acid, p-toluenesulfonic acid, citric acid, salicylic acid, tartaric acid, methanesulfonic acid, isonicotinic acid, acid citric acid, oleic acid, tannic acid, pantothenic acid, hydrogen tartrate, ascorbic acid, gentisic acid, fumaric acid, gluconic acid, sugar acid, formic acid, ethanesulfonic acid, pamoic acid (i.e., 4,4'-methylenebis(3-hydroxy-2-naphthalenecarboxylic acid)), amino acid (such as glutamic acid, arginine), etc. When the compound of the present disclosure contains a relatively acidic and relatively basic functional group, then it can be converted into a base addition salt or an acid addition salt. For details, see Berge et al., "Pharmaceutical Salts", Journal of Pharmaceutical Science 66: 1-19 (1977), or Handbook of Pharmaceutical Salts: Properties, Selection, and Use (P. Heinrich Stahl and Camille G. Wermuth, ed., Wiley-VCH, 2002).

The term "solvent compound" refers to a substance formed by combining the compound of the present disclosure with a stoichiometric or non-stoichiometric solvent. The solvent molecules in the solvate can exist in an ordered or non-ordered arrangement. The solvents include but are not limited to: water, methanol, ethanol and the like.

The terms "pharmaceutically acceptable salt" and "solvent compound" in the term "pharmaceutically acceptable salt solvent compound" refer, as described above, to the substance formed by combining the compound 1 of the present disclosure with a relatively non-toxic, pharmaceutically acceptable acid or base, 2 and a stoichiometric or non-stoichiometric solvent.

The term "crystal form" refers to that the ions or molecules are arranged strictly periodically in three-dimensional space in a certain way, and have the law of periodic recurrence at a certain distance; due to the different periodic arrangement, there can be a variety of crystal forms, that is, polymorph phenomenon.

The term "compound", "pharmaceutically acceptable salt", "solvate" and "solvate of the pharmaceutically acceptable salt" may exist in the form of a single stereoisomer or a mixture thereof (e.g. racemate) if there are stereoisomers. The term "stereoisomer" refers to cis-trans isomer or optical isomer. These stereoisomers may be separated, purified and enriched by asymmetric synthesis methods or chiral separation methods (including but not limited to thin-layer chromatography, rotation chromatography, column chromatography, gas chromatography, high-pressure liquid chromatography, etc.), and may also be obtained by chiral resolution by forming bonds with other chiral compounds (chemical bonding, etc.) or salting (physical bonding, etc.). The term "single stereoisomer" refers to that the mass content of one stereoisomer of the compound of the disclosure relative to all stereoisomers of the compound is not less than 95%.

The term "compound", "pharmaceutically acceptable salt", "solvate" and "solvate of the pharmaceutically acceptable salt" may exist in the form of a single tautomer or a mixture thereof (e.g. racemate) if there are tautomers, preferably exist mainly in the form of more stable tautomers.

The atoms in the term "compound", "pharmaceutically acceptable salt", "solvate" and "solvate of the pharmaceutically acceptable salt" can be present in their natural or unnatural abundance. Taking hydrogen atom as an example, its natural abundance refers to that about 99.985% is protium and about 0.015% is deuterium; the unnatural abundance form refers to that about 95% of it is deuterium. That is, one or more of the atoms in the term "compound", "pharmaceutically acceptable salt", "solvate" and "solvate of the pharmaceutically acceptable salt" can be present in their natural or unnatural abundance.

When any variable (such as $R^1$) appears many times in the definition of the compound, the definition at each position of the variable has nothing to do with the definitions at other positions, and their meanings are independent of each other. Therefore, if a group is replaced by one, two or three $R^1$ groups, that is, the group may be replaced by up to three $R^1$ groups, and the definition $R^1$ in this position is independent of the definition of other $R^1$ in other positions. In addition, the combination of substituents and/or variables is only allowed if the combination results in a stable compound.

The term "halogen" refers to fluorine, chlorine, bromine or iodine.

The term "alkyl" refers to a linear or branched alkyl containing a specified number of carbon atoms. Examples of alkyls include methyl, ethyl, n-propyl, isopropyl, n-butyl, tert-butyl, isobutyl, sec-butyl, n-pentyl, n-hexyl, n-heptyl, n-octyl and similar alkyls.

The term "alkoxy" refers to the group-O—$R^x$, wherein $R^x$ is an alkyl as defined above.

The term "cycloalkyl" refers to monovalent saturated cycloalkyl, preferably monovalent saturated cycloalkyl containing 3-7 cyclic carbon atoms, more preferably monovalent saturated cycloalkyl containing 3-6 carbon atoms, such as cyclopropyl, cyclobutyl, cyclopentyl or cyclohexyl.

The term "heterocylcoalkyl" refers to a saturated monocyclic group containing heteroatoms, preferably 3- to 7-membered saturated monocyclic group containing 1, 2 or 3 ring heteroatoms independently selected from N, O and S. Examples of heterocyclic alkyls are pyrrolyl, tetrahydrofuranyl, tetrahydropyranyl, tetrahydrothiophenyl, tetrahydropyridyl, tetrahydropyrrolyl, azetidinyl, thiazolidinyl, imidazolidinyl, piperidyl, morpholinyl, thiomorpholinyl, piperazinyl, azacycloheptanyl, diazepanyl, oxazepanyl, etc. Preferably, the heterocyclic group is morpholin-4-yl, piperidin-1-yl, pyrrolidin-1-yl, thiomorpholin-4-yl and 1,1-dioxothiomorpholin-4-yl.

The term "heteroaryl" refers to aromatic group containing heteroatoms, preferably 5- to 6-membered monocyclic ring or 9- to 10-membered bicylcic ring containing one, two or three heteroatoms independently selected from nitrogen, oxygen and sulfur, such as furanyl, pyridyl, pyridazinyl, pyrimidinyl, pyrazinyl, thiophenyl, isoazolyl, oxazolyl, diazoyl, imidazolyl, pyrrolyl, pyrazolyl, triazolyl, tetrazolyl, thiazolyl, isothiazolyl, thiadiazole, benzimidazolyl, indolyl, indazolyl, benzothiazolyl, benzoisothiazolyl, benzazolyl, benzoisothiazolyl, quinolinyl, isoquinolinyl, etc.

The term "pharmaceutical excipient" refers to excipient and additive used in the preparation of a medicament and the formulation of prescription, and are all substances contained in the pharmaceutical preparation except the active ingredient. Refer to Volume IV of Pharmacopoeia of the people's Republic of China (2015 Edition) or Handbook of pharmaceutical exceptions (Raymond C Rowe, 2009 Sixth Edition)

The term "treatment" refers to therapeutic therapy. When referring to a specific disease, the treatment refers to: (1) alleviating one or more biological manifestations of a disease or condition, (2) interfering with (a) one or more points in the biological cascade leading to or causing a condition, or (b) one or more biological manifestations of a condition, (3) improving one or more symptoms, effects or side effects related to a condition, or one or more symptoms, effects or side effects related to a condition or the treatment, or (4)

slowing down the development of one or more biological manifestations of a disease or condition.

The term "prevention" refers to the reduction in the risk of acquiring or developing a disease or disorder.

The term "therapeutically effective amount" refers to the amount of a compound sufficient to effectively treat the disease or disorder described herein when given to a patient in need. The "therapeutic effective amount" may vary according to the compound, the disease and its severity, and the age of the patient to be treated, but can be adjusted by those skilled in the art as needed.

On the basis of not violating common knowledge in the field, the above-mentioned preferred conditions can be combined arbitrarily to obtain preferred embodiments of the present disclosure.

The reagents and raw materials used in the present disclosure are all commercially available.

The positive progressive effect of the present disclosure is that the compounds can significantly reduce the levels of HBsAg, HBeAg and HBV DNA, and can be used for preparing a drug for treating hepatitis B, and has good market prospects.

DETAILED DESCRIPTION OF THE EMBODIMENTS

The following examples further illustrate the present disclosure, but the present disclosure is not limited thereto. In the following examples, experimental methods without specific conditions are selected according to conventional methods and conditions, or according to the product specification.

Embodiment 1. 4-(2-(8-chloro-1,4-dihydroquinazolin-2-yl)thiazol-4-yl)benzoic acid (I-1)

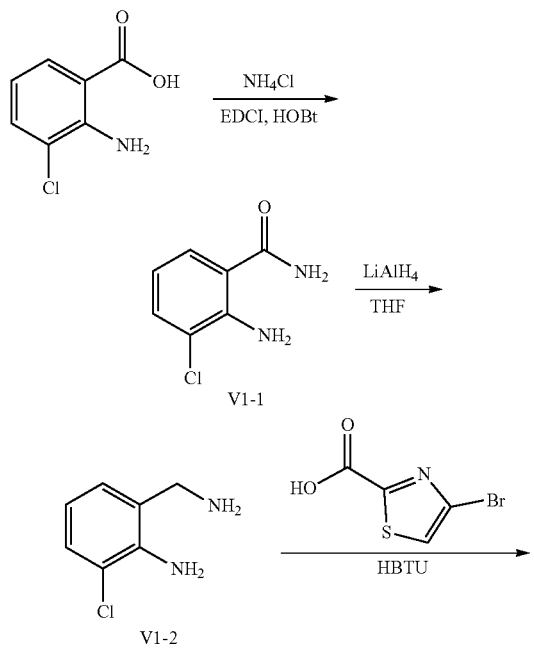

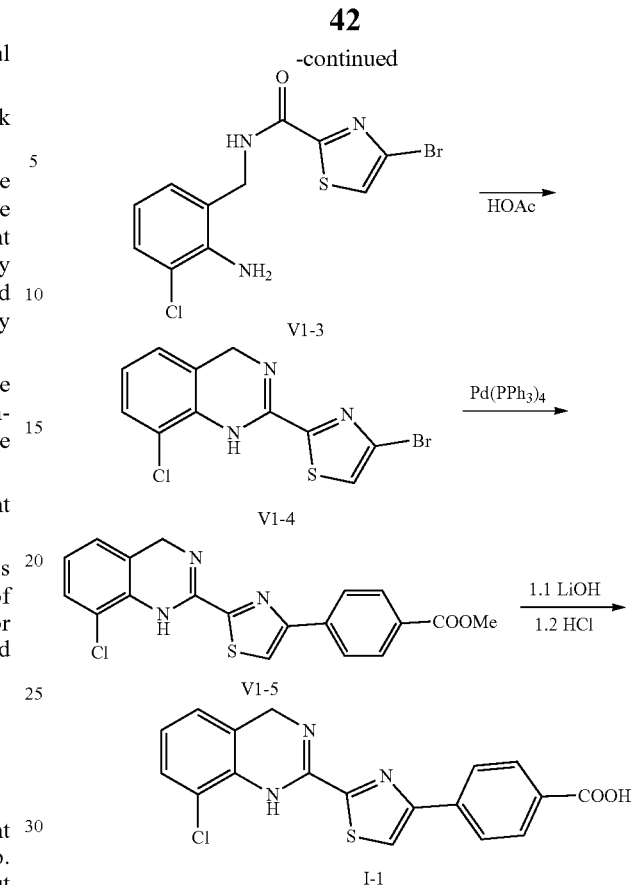

Synthesis of Intermediate V1-1

2-Amino-3-chlorobenzoic acid (10 mmol), 1-hydroxybenzotriazole (HOBt, 1.3 eq.), 1-(3-dimethylaminopropyl)-3-ethylcarbodiimide hydrochloride (EDCI, 1.2 eq.) and ammonium chloride (4 eq.) were suspended in dimethylformamide (10 mL), diisopropylethylamine (4 eq.) was injected under the protection of nitrogen, the reaction was carried out overnight at room temperature and was detected as complete by TLC. Water was added to the mixture, and the mixture was extracted with ethyl acetate, evaporated to dryness, and slurried with n-heptane/ethyl acetate=50/1 to obtain a yellow solid with a yield of 82%. LCMS: M+1=171.

Synthesis of Intermediate V1-2

Intermediate V1-1 (5 mmol) was dissolved in anhydrous tetrahydrofuran (50 mL), lithium aluminum hydride (2.5 eq.) was added at 0° C., when the addition was complete, the reaction was refluxed overnight and was detected as complete by TLC. The lithium aluminum hydride was quenched at 0° C., and dried over anhydrous sodium sulfate. The mixture was filtered and evaporated to dryness, then purified by column chromatography to obtain a yellow liquid, with a yield of 56%. LCMS: M+1=157.

Synthesis of Intermediate V1-3

The intermediates V1-2 (2.7 mmol), 4-bromothiazole-2-carboxylic acid (1 eq.), benzotriazole-1-tetramethylhexafluorophosphate (HBTU, 1.1 eq.) were dissolved in dichloromethane (10 mL), triethylamine (2 eq.) was added dropwise at 0° C., and the reaction was carried out at room temperature overnight, and was detected as complete by TLC. Water was added to the mixture, and the mixture was extracted with ethyl acetate, evaporated to dryness, the crude product was directly used in the next step. LCMS: M+1=346, 348.

Synthesis of Intermediate V1-4

The crude product from the previous step was dissolved in acetic acid (5 mL) and refluxed for 3 hours, and the reaction was detected as complete by TLC. The acetic acid was evaporated to dryness, and the mixture was adjusted to basic with sodium bicarbonate, extracted with ethyl acetate, then dried. The crude product was purified by silica gel chromatography to obtain a yellow solid, with a two-step yield of 42%. LCMS: M+1=328, 330.

Synthesis of Intermediate V1-5

The intermediates V1-4 (1.15 mmol), 4-(methoxycarbonyl)phenylboric acid (1.1 eq.), potassium carbonate (2 eq.), tetrakis(triphenylphosphine)palladium (5% eq.) were placed in a flask under nitrogen protection. Tetrahydrofuran (10 mL) and water (1 mL) were added and refluxed at 80° C. overnight, and the reaction was detected as complete by TLC. Water was added to the mixture, and the mixture was extracted with ethyl acetate, then dried. The crude product was purified by silica gel chromatography to obtain a yellow solid with a yield of 48%. LCMS: M+1=384.

Synthesis of Compound I-1

Intermediate V1-5 (0.55 mml) was dissolved in tetrahydrofuran (5 mL) and methanol (1 mL), lithium hydroxide (2 eq) aqueous solution (1 mL) was added with stirring at room temperature, and the reaction was carried out at room temperature overnight and was detected as complete by TLC. The solvent was evaporated, 5 mL of water was added to the mixture, the pH value was adjusted with hydrochloric acid to 5-6, filtered and oven-dried to obtain a yellow solid with a yield of 44%. LCMS: M+1=370. 1H-NMR (400 MHz, DMSO-d6): δ 13.04 (s, 1H), 8.52 (s, 1H), 8.37 (s, 1H), 8.22 (d, J=8.2 Hz, 2H), 8.04 (d, J=8.2 Hz, 2H), 7.30-7.24 (m, 1H), 7.03-6.97 (m, 2H), 4.71 (s, 2H).

Embodiment 2. 4-(2-(8-chloro-4-methyl-1,4-dihydroquinazolin-2-yl)thiazol-4-yl)benzoic acid (I-2)

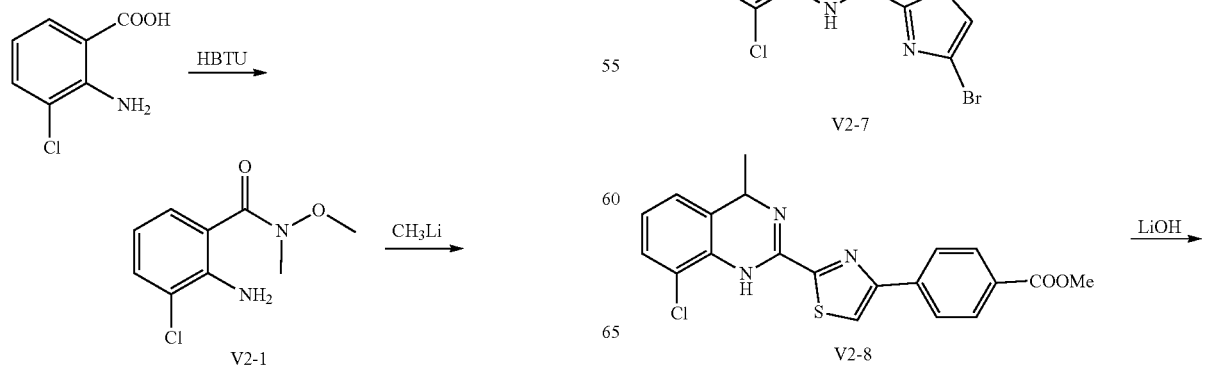

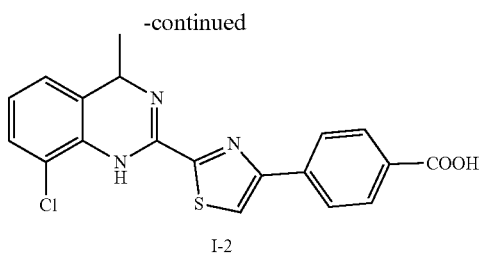

I-2

Synthesis of Intermediate V2-1

2-Amino-3-chlorobenzoic acid (20 mmol) and N-methyl-N-methoxyamine hydrochloride (1.5 eq.) were dissolved in dimethylformamide (10 mL), and N-methylmorphorphine (4.5 eq.) and benzotriazole-1-tetramethylhexafluorophosphate (HBTU, 1.5 eq.) were added thereto. The reaction was stirred overnight, and was detected as complete by TLC. The reaction was poured into water, extracted with ethyl acetate, and the crude product was purified by silica gel chromatography to obtain a yellow oil with a yield of 95%. LCMS: M+1=215.

Synthesis of Intermediate V2-2

Intermediate V2-1 (5 mmol) was dissolved in anhydrous tetrahydrofuran (10 mL), methyl lithium was added dropwise at 0° C. under nitrogen protection, when the addition was complete, the reaction was carried out overnight and was detected as complete by TLC. The reaction was quenched by saturated aqueous ammonium chloride solution, extracted with ethyl acetate, and the crude product was purified by silica gel chromatography to obtain a product with a yield of 57%. LCMS: M+1=170.

Synthesis of Intermediate V2-3

Intermediate V2-2 (9 mmol), tert-butylsulfinamide (1 eq.), and titanium tetraisopropanolate (4 eq.) were dissolved in anhydrous tetrahydrofuran (10 mL) under nitrogen protection. The tube was sealed at 75° C. and the reaction was carried out for 12 h. The reaction was quenched by water, and dissolved by adding ethyl acetate, then filtered by diatomaceous earth. The mixture was extracted with ethyl acetate. The crude product was purified by silica gel chromatography to obtain a yellow solid with a yield of 72%. LCMS: M+1=273.

Synthesis of Intermediate V2-4

Intermediate V2-3 (2 mmol) was dissolved in anhydrous tetrahydrofuran (5 mL), under nitrogen protection, DIBAL-H (2 eq.) was added dropwise at −78° C., the reaction was carried at −78° C. for 3 h. The reaction was quenched by water, and the mixture was extracted with ethyl acetate, evaporated to dryness, the crude product was directly used in the next step. LCMS: M+1=275.

Synthesis of Intermediate V2-5

The crude product from the previous step was dissolved in methanol, hydrogen chloride/dioxane (4 eq.) solution was added dropwise at room temperature, the reaction was carried out at room temperature overnight, and was detected as complete by TLC. The reaction was evaporated to dryness, the pH value was adjusted to 8 by adding ammonia, and the crude product was purified by silica gel chromatography to obtain a product with a two-step yield of 89%. LCMS: M+1=171.

Synthesis of Intermediate V2-6

The intermediates V2-5 (2.47 mmol), 4-bromothiazole-2-carboxylic acid (1 eq.), benzotriazole-1-tetramethylhexafluorophosphate (HBTU, 1.1 eq.) were dissolved in toluene (10 mL), triethylamine (2 eq.) was added dropwise at 0° C., and the reaction was carried out at room temperature overnight, and was detected as complete by TLC. Water was added to the mixture, and the mixture was extracted with ethyl acetate, evaporated to dryness, the crude product was directly used in the next step. LCMS: M+1=360, 362.

Synthesis of Intermediate V2-7

The crude product from the previous step was dissolved in acetic acid (4 mL) and refluxed for 3 hours. The acetic acid was evaporated to dryness, and the pH value of the mixture was adjusted to 8-9 with sodium bicarbonate, then the mixture was evaporated to dryness, the crude product obtained was directly used in the next step. LCMS: M+1=342, 344.

Synthesis of Intermediate V2-8

The crude product from the previous step, 4-(methoxycarbonyl)phenylboric acid (1.1 eq.), potassium carbonate (2 eq.), tetrakis(triphenylphosphine)palladium (5% eq.) were placed in a flask under nitrogen protection. Tetrahydrofuran (10 mL) and water (1 mL) were added and refluxed at 80° C. overnight, and the reaction was detected as complete by TLC. Water was added to the mixture, the mixture was extracted with ethyl acetate, and the crude product obtained was purified by silica gel chromatography to obtain a pale yellow solid with a three-step yield of 19%. LCMS: M+1=398.

Synthesis of Compound I-2

Intermediate V2-8 (0.2 mml) was dissolved in tetrahydrofuran (5 mL) and methanol (1 mL), lithium hydroxide (2 eq) aqueous solution (1 mL) was added with stirring at room temperature, and the reaction was carried out at room temperature overnight, and was detected as complete by TLC. The solvent was evaporated to dryness, 5 mL of water was added to the mixture, the pH value was adjusted with hydrochloric acid to 5-6, the mixture was filtered, oven-dried, and slurried with a small amount of dichloromethane to obtain a pale yellow solid with a yield of 99%. LCMS: M+1=384. $^1$H-NMR (400 MHz, DMSO-$d_6$): δ 13.08 (s, 1H), 8.56 (s, 1H), 8.52 (s, 1H), 8.23 (d, J=6.8 Hz, 2H), 8.05 (d, J=6.8 Hz, 2H), 7.30 (d, J=6.4 Hz, 1H), 7.14-6.99 (m, 2H), 4.90 (q, J=3.9 Hz, 1H), 1.41 (d, J=3.9 Hz, 3H).

Embodiment 3. 4-(2-(8-chloro-4,4-dimethyl-1,4-dihydroquinazolin-2-yl)thiazol-4-yl)benzoic acid (I-4)

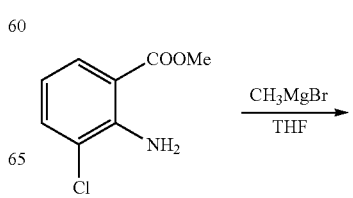

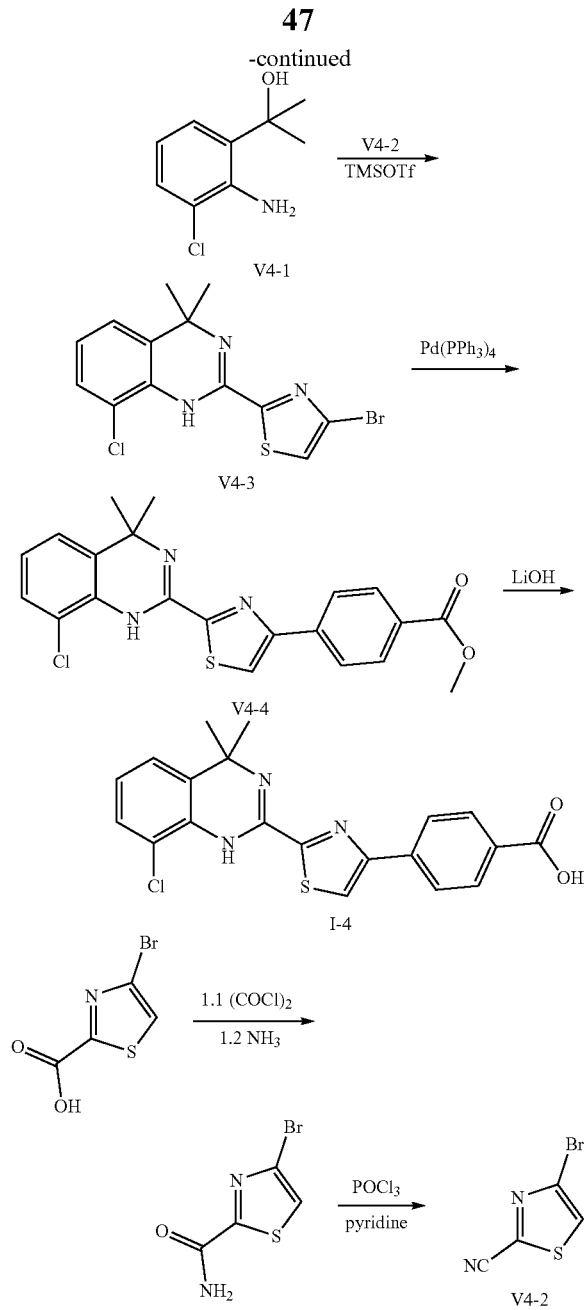

Synthesis of Intermediate V4-1

Methyl 2-amino-3-chlorobenzoate (6.6 mmol) was dissolved in anhydrous tetrahydrofuran (10 mL) under nitrogen protection. Methylmagnesium bromide (3 eq.) was added dropwise at 0° C., when the addition was complete, the reaction was carried out overnight and was detected as complete by TLC. The reaction was quenched by saturated ammonium chloride, extracted with ethyl acetate, and the crude product was purified by silica gel chromatography to obtain a product with a yield of 96%. LCMS: M+1=186.

Synthesis of Intermediate V4-2

4-Bromothiazole-2-carboxylic acid (24.04 mmol) was added to dry dichloromethane (50 mL), cooled in an ice bath under nitrogen protection, and oxalyl chloride (2 eq.) was added dropwise, after the addition, the reaction was carried out at room temperature for 2 h. The reaction mixture was concentrated to dryness, dissolved in dry tetrahydrofuran (50 mL), and dropped into 25%-28% ammonia (30 mL), the temperature was kept below 5° C., after the addition, the reaction was carried out at room temperature for 1 h. The reaction was detected as complete by TLC. The reaction solution was poured into water, extracted with ethyl acetate, washed with 2M hydrochloric acid until weak acidity, and dried to obtain 4-bromothiazole-2-carboxamide (crude product 5 g).

4-Bromothiazole-2-carboxamide (24.15 mmol) was added to pyridine (20 eq.), cooled to 5° C. under nitrogen protection, and phosphorus oxychloride (5 eq.) was added dropwise, after the addition, the reaction was carried out overnight, and was detected as complete by TLC. The reaction was quenched by slowly pouring into crushed ice, extracted with ethyl acetate, then dried, and the crude product was purified by silica gel chromatography to obtain V4-2 (4 g, with a yield of 88%).

Synthesis of Intermediate V4-3

Intermediate V4-1 (1 mmol), intermediate V4-2 (1 eq.) were placed in a sealed tube, trimethylsilyl trifluoromethanesulfonate (3 mL) was added, and the reaction was carried out at 120° C. for 5 h, and the reaction was detected as complete by TLC. The reaction mixture was poured into water, and adjusted to basic by adding sodium bicarbonate, and the crude product was purified by silica gel chromatography to obtain a pale yellow solid with a yield of 75%. LCMS: M+1=356, 358.

Synthesis of Intermediate V4-4

The intermediates V4-3 (0.35 mmol), 4-(methoxycarbonyl)phenylboric acid (1.1 eq.), potassium carbonate (2 eq.), tetrakis(triphenylphosphine)palladium (5% eq.) were placed in a flask under nitrogen protection. Tetrahydrofuran (5 mL) and water (1 mL) were added and refluxed at 80° C. overnight, and the reaction was detected as complete by TLC. Water was added to the mixture, the mixture was extracted with ethyl acetate, and the crude product obtained was purified by silica gel chromatography to obtain a pale yellow solid with a yield of 58%. LCMS: M+1=412.

Synthesis of Compound I-4

Intermediate V4-4 (0.1 mmol) was dissolved in tetrahydrofuran (5 mL) and methanol (1 mL), lithium hydroxide (2 eq.) aqueous solution (1 mL) was added with stirring at room temperature, and the reaction was carried out at room temperature overnight, and was detected as complete by TLC. The solvent was evaporated, 5 mL of water was added to the mixture, the pH value was adjusted with hydrochloric acid to 5-6, filtered and oven-dried to obtain a yellow solid, with a yield of 83%. LCMS: M+1=398. $^1$H-NMR (400 MHz, DMSO-$d_6$): δ 13.04 (s, 1H), 8.53 (s, 1H), 8.36 (s, 1H), 8.27 (d, J=8.1 Hz, 2H), 8.05 (d, J=8.1 Hz, 2H), 7.31 (d, J=7.8 Hz, 1H), 7.26 (d, J=7.8 Hz, 1H), 7.06 (t, J=7.8 Hz, 1H), 1.63 (s, 6H).

Embodiment 4. 4-(2-(8'-chloro-1'H-spiro[cyclopropyl-1,4'-quinazolin]-2'-yl)thiazol-4-yl)benzoic acid (I-5)

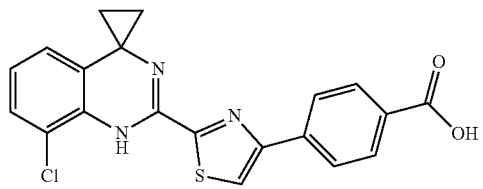

Compound I-5 was synthesized by referring to the synthesis of compound I-2. 2-(1-Aminocyclopropyl)-6-chloroaniline (intermediate V5-6) was used instead of 2-(1-aminoethyl)-6-chloroaniline (intermediate V2-5). Compound I-5, LCMS: M+1=396. $^1$H-NMR (400 MHz, DMSO-$d_6$): δ 12.99 (s, 1H), 8.51 (s, 1H), 8.32 (s, 1H), 8.27 (d, J=7.9 Hz, 2H), 8.13 (d, J=7.9 Hz, 2H), 7.22 (d, J=7.5 Hz, 1H), 7.14 (d, J=7.5 Hz, 1H), 7.01 (t, J=7.5 Hz, 1H), 1.68-1.61 (m, 2H), 1.37-1.30 (m, 2H).

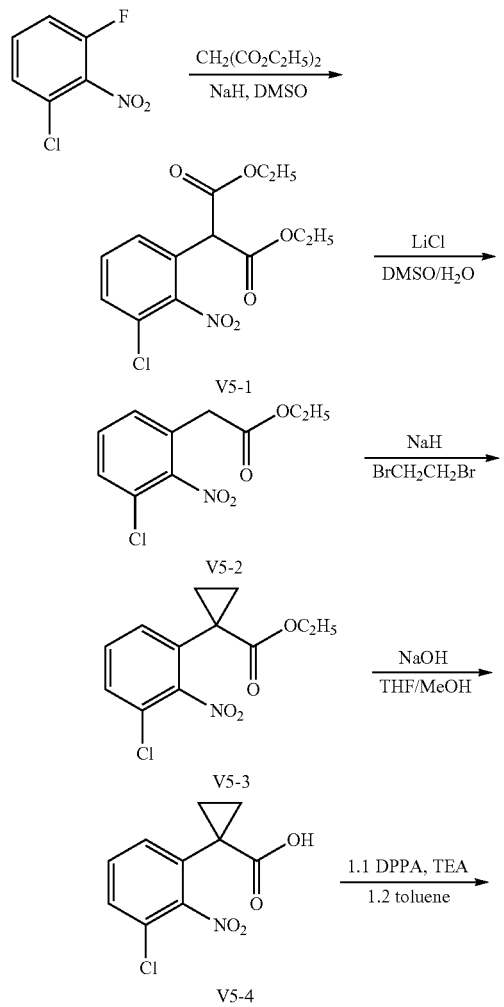

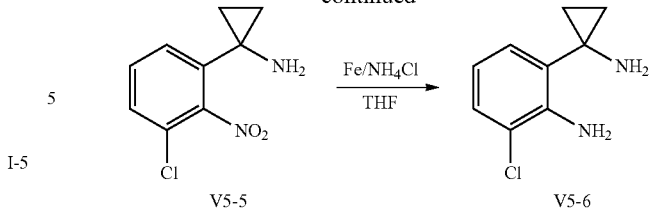

Synthesis of Intermediate V5-1

Sodium hydrogen (60%, 2.2 eq.) was added to dry dimethyl sulfoxide (80 mL), diethyl malonate (2.0 eq.) was added dropwise at room temperature, and then reacted at 100° C. for 30 min. After cooling to room temperature, 2-chloro-6fluoronitrobenzene (45.57 mmol) was added, after the addition, the reaction was performed at 100° C. for 2 hours, and the reaction was detected as complete by TLC. The reaction solution was added to a saturated aqueous ammonium chloride solution, extracted with ethyl acetate, washed with water, and dried. The crude product was purified by silica gel chromatography to obtain intermediate V5-1, with a yield of 53%. LCMS: M+1=316.

Synthesis of Intermediate V5-2

Intermediate V5-1 (22.17 mmol) was added to dry dimethyl sulfoxide (80 mL), lithium chloride (2.2 eq.) and water (1.1 eq.) were added, after the addition, the reaction was carried out at 100° C. for 3 h. The reaction was detected as complete by TLC, the reaction solution was cooled, then ethyl acetate was added, the mixture was washed with water and dried. The crude product was purified by silica gel chromatography to obtain intermediate V5-2, with a yield of 83%. LCMS: M+1=244.

Synthesis of Intermediate V5-3

Intermediate V5-2 (16.42 mmol) and 1,2-dibromoethane (1.1 eq.) were added to dimethylformamide (40 mL), the temperature was reduced to 0° C. under nitrogen protection, and sodium hydrogen (60%, 4.0 eq.) was added in batches. After the addition, the reaction was carried out overnight, and was detected as complete by TLC. The reaction solution was poured into ice water, the pH value was adjusted to 5-6 with 2M hydrochloric acid, the mixture was extracted with ethyl acetate, washed with water and dried. The crude product was purified by silica gel chromatography to obtain intermediate V5-3, with a yield of 29%. LCMS: M+1=270.

Synthesis of Intermediate V5-4

Intermediate V5-3 (4.45 mmol) was added in tetrahydrofuran (10 mL) and methanol (3 mL), sodium hydroxide (2.0 eq.) aqueous solution (2 mL) was added, and the reaction was carried out at 50° C. overnight, and was detected as complete by TLC. The reaction solution was concentrated, 10 mL of water was added, and the pH value was adjusted to 5-6 with 2M hydrochloric acid, the mixture was extracted with ethyl acetate, washed with water and dried, then concentrated to obtain intermediate V5-4 with a yield of 56%. LCMS: M+1=242.

Synthesis of Intermediate V5-5

Intermediate V5-4 (2.28 mmol) and triethylamine (1.5 eq.) were added to dichloromethane, and diphenylphosphoryl azide (1.5 eq.) was added dropwise with stirring, and the reaction was carried out at room temperature for 3 h after addition. The reaction was detected as complete by TLC, the reaction solution was concentrated and dried, toluene (10 mL) was added, and the reaction was carried out at an external temperature of 120° C. for 2 h, cooled to room temperature, 6M hydrochloric acid (5 mL) was added, and the reaction was carried out at 100° C. for 2 h. The reaction solution was added to a saturated aqueous sodium bicarbonate solution, extracted with ethyl acetate, washed with water, and dried. The crude product was purified by silica gel chromatography to obtain intermediate V5-5 with a yield of 82%. LCMS: M+1=213.

Synthesis of Intermediate V5-6

Intermediate V5-5 (1.79 mmol), reduced iron powder (5 eq.) and ammonium chloride (1 eq.) were added to 10 mL of tetrahydrofuran and the reaction was carried out at reflux for 2 h, and was detected as complete by TLC. The reaction mixture was cooled to room temperature and filtered, the filter cake was washed with tetrahydrofuran, the crude product was purified by silica gel chromatography to obtain intermediate V5-6 with a yield of 76%. LCMS: M+1=183.

Embodiment 5. 4-(2-(8'-chloro-1'H-spiro[oxetanyl-3,4'-quinazolin]-2'-yl)thiazol-4-yl)benzoic acid (I-11)

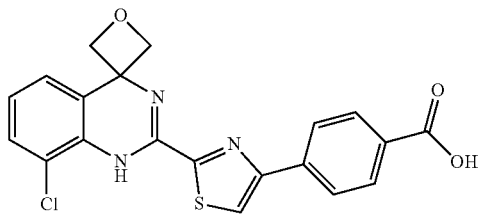

Compound I-11 was synthesized by referring to the synthesis of compound I-2, 3-(2-amino-3-chlorophenyl)oxetanyl-3-amine (Intermediate V11-4) was used instead of 2-(1-aminoethyl)-6-chloroaniline (Intermediate V2-5). Compound I-11, LCMS: M+1=412. $^1$H-NMR (400 MHz, DMSO-d$_6$): δ 13.00 (s, 1H), 8.67 (s, 1H), 8.48 (s, 1H), 8.32 (d, J=8.1 Hz, 2H), 8.13 (d, J=7.9 Hz, 2H), 7.33 (d, J=7.8 Hz, 1H), 7.26 (d, J=7.8 Hz, 1H), 7.12 (t, J=7.8 Hz, 1H), 4.45-4.35 (m, 2H), 4.17-4.07 (m, 2H).

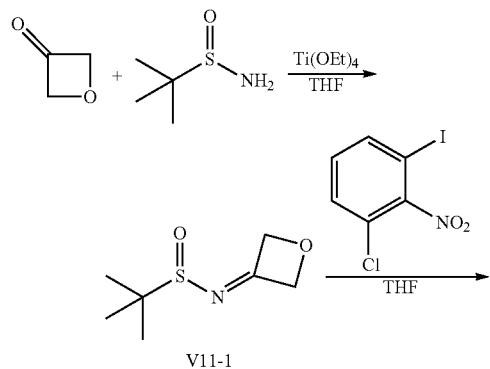

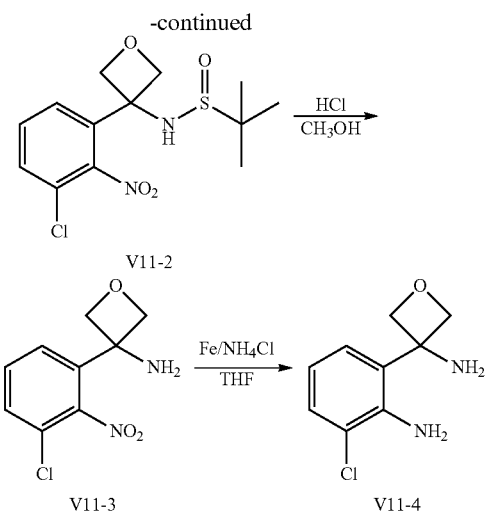

Synthesis of Intermediate V11-1

Oxetanyl-3-one (69.38 mmol) was added to dry tetrahydrofuran (50 mL), and tert-butyl sulfinamide (1.0 eq.) and tetraethoxytitanium (20 mL) were added sequentially and the reaction was carried out at 50° C. for 5 h. The reaction mixture was poured into water, extracted with ethyl acetate, and dried. The crude product was purified by silica gel chromatography to obtain intermediate V11-1 with a yield of 40%.

Synthesis of Intermediate V11-2

Chloro-3-iodo-2-nitrobenzene (7.06 mmol) was added to dry tetrahydrofuran (20 mL), under nitrogen protection, and cooled to −78° C. N-butyl lithium (2.5M, 1.2 eq.) was added dropwise and the reaction was carried out at this temperature for 30 min. The tetrahydrofuran solution (50 mL) of intermediate V11-1 (1.2 eq.) was added dropwise, and after the addition, the reaction was carried out at −78° C. for 30 min and overnight at room temperature. TLC detected the disappearance of raw materials. The reaction mixture was poured into water, extracted with ethyl acetate, and dried. The crude product was purified by silica gel chromatography to obtain intermediate V11-2 with a yield of 34%. LCMS: M+1=333.

Synthesis of Intermediate V11-3

Intermediate V11-2 (2.25 mmol) was added in methanol (10 mL), sodium hydroxide/dioxane aqueous solution (4 M, 10 mL) was added, and the reaction was carried out at room temperature for 1 h, and was detected as complete by TLC. The reaction solution was concentrated to dryness to obtain a crude product, Intermediate V11-3, LCMS: M+1=229.

Synthesis of Intermediate V11-4

Intermediate V11-3 (2.25 mmol) obtained in the previous step was added into tetrahydrofuran (15 mL), reduced iron powder (5 eq.) and ammonium chloride (1 eq.) were added, and the reaction was carried out at 65° C. for 2 h, and was detected as complete by TLC. A saturated aqueous sodium carbonate solution was added to the reaction solution, filtered, and extracted with ethyl acetate, the organic phase was washed with water, dried and concentrated. The crude product was purified by silica gel chromatography to obtain intermediate V11-4, with a two-step yield of: 56%. LCMS: M+1=199.

Embodiment 6. 4-(2-(4,4-dimethyl-1,4-dihydroquinazolin-2-yl)thiazol-4-yl)benzoic acid (I-20)

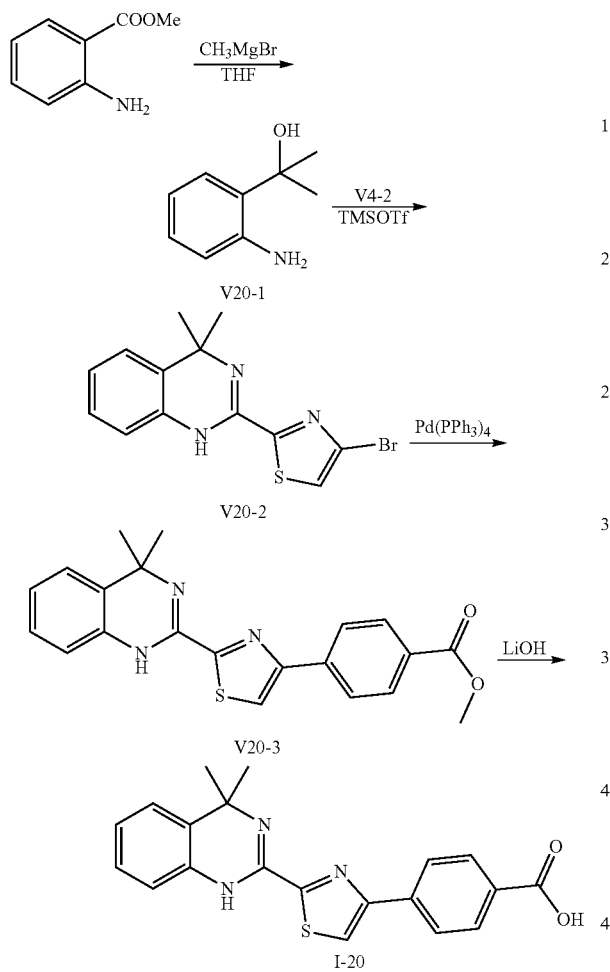

Synthesis of Intermediate V20-1

Methyl 2-aminobenzoate (33.08 mmol) was dissolved in anhydrous tetrahydrofuran (50 mL) under nitrogen protection. Methylmagnesium bromide (3 eq.) was added dropwise at 0° C., when the addition was complete, the reaction was carried out overnight and was detected as complete by TLC. The reaction was quenched by saturated ammonium chloride, extracted with ethyl acetate, and the crude product was purified by silica gel chromatography to obtain a product, with a yield of 85%. LCMS: M+1=152.

Synthesis of Intermediate V20-2

Intermediate V20-1 (6.61 mmol), intermediate V4-2 (1 eq.) were placed in a sealed tube, trimethylsilyl trifluoromethanesulfonate (10 mL) was added, and the reaction was carried out at 120° C. for 5 h, and the reaction was detected as complete by TLC. The reaction mixture was poured into water, and adjusted to basic by adding sodium bicarbonate, and the crude product was purified by silica gel chromatography to obtain a pale yellow solid with a yield of 72%. LCMS: M+1=322, 324.

Synthesis of Intermediate V20-3

The intermediates V20-2 (0.31 mmol), 4-(methoxycarbonyl)phenylboric acid (1.1 eq.), potassium carbonate (2 eq.), tetrakis(triphenylphosphine)palladium (5% eq.) were placed in a flask under nitrogen protection. Tetrahydrofuran (5 mL) and water (1 mL) were added and refluxed at 80° C. overnight, and the reaction was detected as complete by TLC. Water was added to the mixture, the mixture was extracted with ethyl acetate, and the crude product obtained was purified by silica gel chromatography to obtain a pale yellow solid with a yield of 65%. LCMS: M+1=378.

Synthesis of Compound I-20

Intermediate V20-3 (0.26 mmol) was dissolved in tetrahydrofuran (5 mL) and methanol (1 mL), lithium hydroxide (2 eq) aqueous solution (1 mL) was added with stirring at room temperature, and the reaction was carried out at room temperature overnight, and was detected as complete by TLC The solvent was evaporated, 5 mL of water was added to the mixture, the pH value was adjusted with hydrochloric acid to 5-6, filtered and oven-dried to obtain a yellow solid with a yield of 70%. Compound I-20, LCMS: M+1=364. $^1$H-NMR (400 MHz, DMSO-$d_6$): δ 13.05 (s, 1H), 8.49 (s, 1H), 8.27 (d, J=8.1 Hz, 2H), 8.04 (d, J=8.1 Hz, 2H), 7.96 (s, 1H), 7.28 (d, J=7.2 Hz, 1H), 7.17 (t, J=7.2 Hz, 1H), 7.08 (t, J=7.3 Hz, 1H), 7.02 (d, J=7.3 Hz, 1H), 1.61 (s, 6H).

Embodiment 7. 4-(2-(8-fluoro-4,4-dimethyl-1,4-dihydroquinazolin-2-yl)thiazol-4-yl)benzoic acid (I-21)

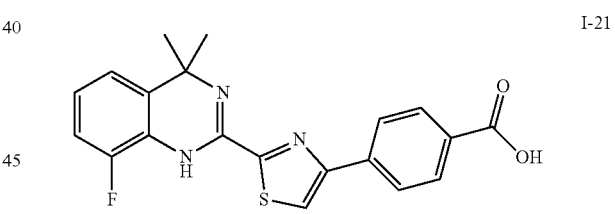

Compound I-21 was synthesized by referring to the synthesis of compound I-4, methyl 2-amino-3-fluorobenzoate was used instead of methyl 2-amino-3-chlorobenzoate. Compound I-21, LCMS: M+1=382. $^1$H-NMR (400 MHz, DMSO-$d_6$) δ 8.52 (s, 1H), 8.28 (d, J=8.5 Hz, 2H), 8.18 (s, 1H), 8.06 (d, J=8.5 Hz, 2H), 7.15-7.05 (m, 3H), 1.64 (s, 6H).

Embodiment 8. 4-(2-(8-bromo-4,4-dimethyl-1,4-dihydroquinazolin-2-yl)thiazol-4-yl)benzoic acid (I-22)

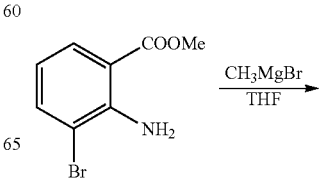

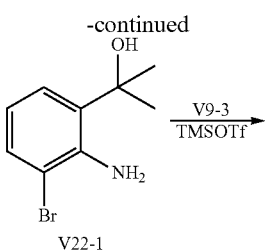

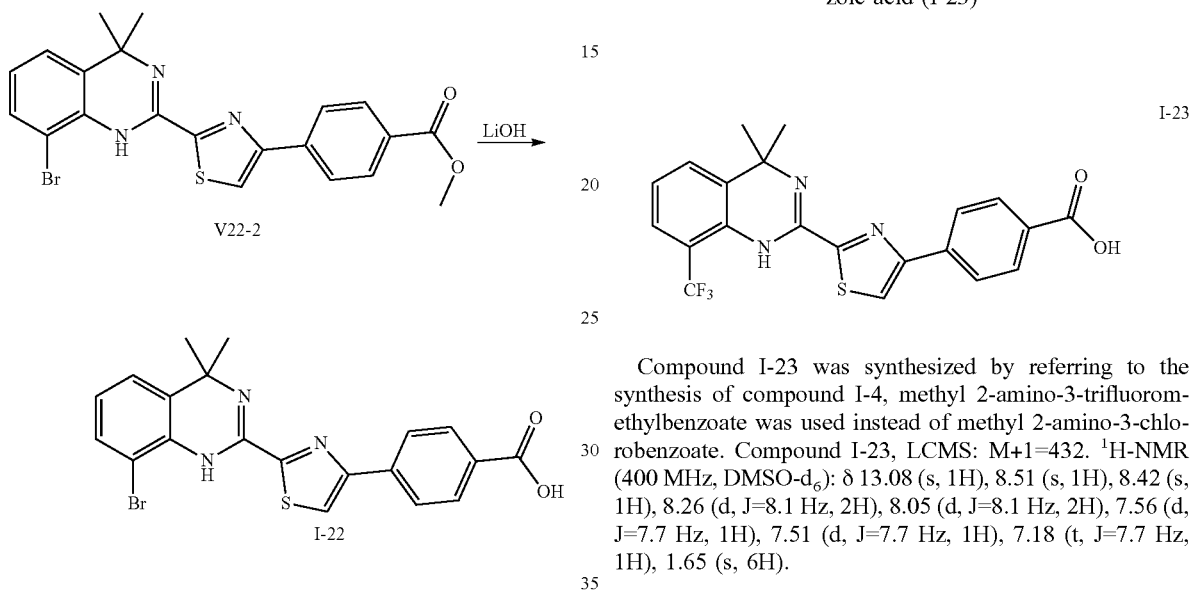

Synthesis of Intermediate V22-1

Methyl 2-amino-3-bromobenzoate (4.35 mmol) was dissolved in anhydrous tetrahydrofuran (10 mL) under nitrogen protection. Methylmagnesium bromide (2.0 eq.) was added dropwise at 0° C., when the addition was complete, the reaction was carried out overnight and TLC detected that most of the raw material was converted. The reaction was quenched by saturated aqueous ammonium chloride solution, extracted with ethyl acetate, and the crude product was purified by silica gel chromatography to obtain intermediate V22-1 with a yield of 76%. LCMS: M+1=230, 232.

Synthesis of Intermediate V22-2

Intermediate V22-1 (0.65 mmol), intermediate V9-3 (1 eq.) were placed in a sealed tube, trimethylsilyl trifluoromethanesulfonate (3 mL) was added, and the reaction was carried out at 120° C. for 5 h, and the reaction was detected as complete by TLC. The reaction mixture was poured into water, and adjusted to basic by adding sodium bicarbonate, and the crude product was purified by silica gel chromatography to obtain intermediate V22-2 with a yield of 55%. LCMS: M+1=456,458.

Synthesis of Compound I-22

Intermediate V22-2 (0.36 mmol) was dissolved in tetrahydrofuran (5 mL) and methanol (1 mL), lithium hydroxide (2 eq) aqueous solution (1 mL) was added with stirring at room temperature, and the reaction was carried out at room temperature overnight, and was detected as complete by TLC. The solvent was evaporated, 5 mL of water was added to the mixture, the pH value was adjusted with hydrochloric acid to 5-6, filtered and oven-dried to obtain compound I-22 with a yield of 76%. LCMS: M+1=442,444. $^1$H-NMR (400 MHz, DMSO-$d_6$): δ 13.05 (s, 1H), 8.52 (s, 1H), 8.31-8.23 (m, 3H), 8.04 (d, J=7.9 Hz, 2H), 7.47 (d, J=7.7 Hz, 1H), 7.29 (d, J=7.7 Hz, 1H), 6.98 (t, J=7.7 Hz, 1H), 1.62 (s, 6H).

Embodiment 9. 4-(2-(4,4-dimethyl-8-trifluoromethyl-1,4-dihydroquinazolin-2-yl)thiazol-4-yl)benzoic acid (I-23)

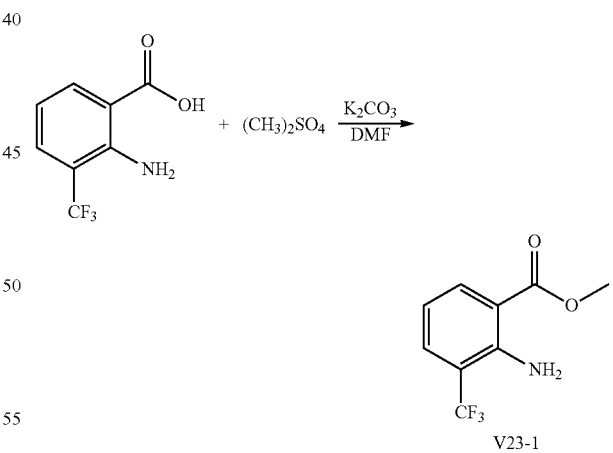

Compound I-23 was synthesized by referring to the synthesis of compound I-4, methyl 2-amino-3-trifluoromethylbenzoate was used instead of methyl 2-amino-3-chlorobenzoate. Compound I-23, LCMS: M+1=432. $^1$H-NMR (400 MHz, DMSO-$d_6$): δ 13.08 (s, 1H), 8.51 (s, 1H), 8.42 (s, 1H), 8.26 (d, J=8.1 Hz, 2H), 8.05 (d, J=8.1 Hz, 2H), 7.56 (d, J=7.7 Hz, 1H), 7.51 (d, J=7.7 Hz, 1H), 7.18 (t, J=7.7 Hz, 1H), 1.65 (s, 6H).

Synthesis of Intermediate V23-1

2-Amino-6-trifluoromethylbenzoic acid (10 mmol), potassium carbonate (1 eq.) and dimethyl sulfate (1 eq.) were added to 15 mL dry dimethylformamide and stirred overnight at room temperature, and the reaction of the raw materials was detected as complete by TLC. The reaction mixture was poured into 50 mL of water, extracted with ethyl acetate, and dried. The crude product was purified by silica gel chromatography to obtain intermediate V23-1 with a yield of 58%. LCMS: M+1=220.

Embodiment 10. 4-(2-(7-chloro-4,4-dimethyl-1,4-dihydroquinazolin-2-yl)thiazol-4-yl)benzoic acid (I-25)

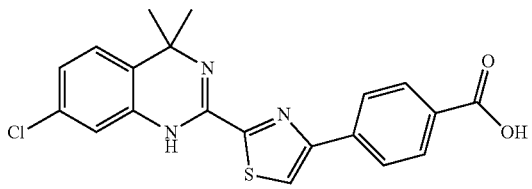

I-25

Compound I-25 was synthesized by referring to the synthesis of compound I-4, methyl 2-amino-4-chlorobenzoate was used instead of methyl 2-amino-3-chlorobenzoate. Compound I-25, LCMS: M+1=398. ¹H-NMR (400 MHz, DMSO-d$_6$): δ 8.52 (s, 1H), 8.26 (d, J=8.1 Hz, 2H), 8.21 (s, 1H), 8.04 (d, J=8.1 Hz, 2H), 7.30 (d, J=8.3 Hz, 1H), 7.10 (d, J=8.3 Hz, 1H), 7.02 (s, 1H), 1.61 (s, 6H).

Embodiment 11. 4-(2-(6-chloro-4,4-dimethyl-1,4-dihydroquinazolin-2-yl)thiazol-4-yl)benzoic acid (I-27)

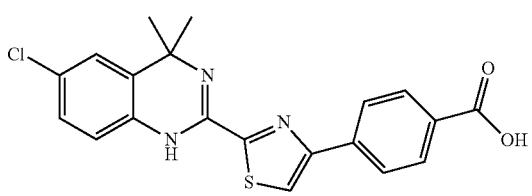

I-27

Compound I-27 was synthesized by referring to the synthesis of compound I-4, methyl 2-amino-5-chlorobenzoate was used instead of methyl 2-amino-3-chlorobenzoate. Compound I-27, LCMS: M+1=398. ¹H-NMR (400 MHz, DMSO-d$_6$): δ 8.50 (s, 1H), 8.26 (d, J=8.2 Hz, 2H), 8.10 (s, 1H), 8.04 (d, J=8.2 Hz, 2H), 7.35 (d, J=1.8 Hz, 1H), 7.20 (dd, J=8.3, 1.8 Hz, 1H), 7.03 (d, J=8.3 Hz, 1H), 1.62 (s, 6H).

Embodiment 12. 6-(2-(4,4-dimethyl-1,4-dihydroquinazolin-2-yl)thiazol-4-yl)benzoic acid (I-34)

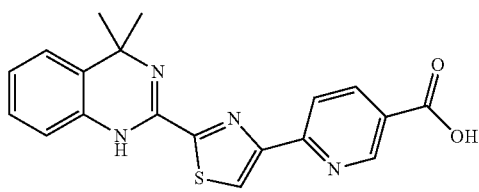

I-34

Compound I-34 was synthesized by referring to the synthesis of compound I-20, in the Suzuki coupling step, 5-methoxycarbonyl-2-pyridineboronic acid was used instead of 4-(methoxycaronyl)phenylboronic acid. Compound I-34, LCMS: M+1=365. ¹H-NMR (400 MHz, DMSO-d$_6$): δ 9.12 (s, 1H), 8.57 (s, 1H), 8.46-8.40 (m, 2H), 8.00 (s, 1H), 7.29 (d, J=7.2 Hz, 1H), 7.19 (t, J=7.2 Hz, 1H), 7.12-7.02 (m, 2H), 1.62 (s, 6H).

Embodiment 13. 5-(2-(4,4-dimethyl-1,4-dihydroquinazolin-2-yl)thiazol-4-yl)pyridin-2-carboxylic acid (I-35)

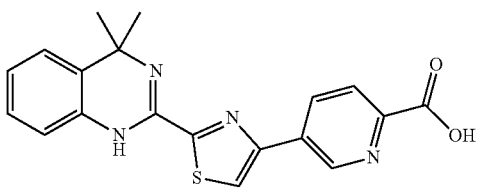

I-35

Compound I-35 was synthesized by referring to the synthesis of compound I-20, in the Suzuki coupling step, 2-methoxycarbonyl-5-pyridineboronic acid pinacol ester was used instead of 4-(methoxycaronyl)phenylboronic acid. Compound I-35, LCMS: M+1=365. ¹H-NMR (400 MHz, DMSO-d$_6$): 9.50 (d, J=1.6 Hz, 1H), 8.85 (s, 1H), 8.70 (dd, J=8.2, 2.0 Hz, 1H), 8.20 (d, J=8.2 Hz, 1H), 7.41 (d, J=7.6 Hz, 1H), 7.30 (br, 2H), 7.25-7.17 (m, 1H), 1.71 (s, 6H).

Embodiment 14. 3-(2-(8-chloro-4,4-dimethyl-1,4-dihydroquinazolin-2-yl)thiazol-4-yl)benzoic acid (I-36)

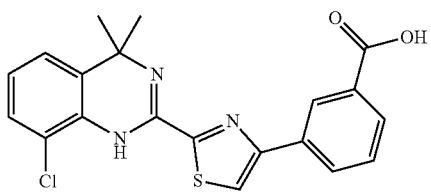

I-36

Compound I-36 was synthesized by referring to the synthesis of compound I-4, in the Suzuki coupling step, 3-methoxycarbonylphenylboronic acid was used instead of 4-(methoxycaronyl)phenylboronic acid. Compound I-36, LCMS: M+1=398. ¹H-NMR (400 MHz, DMSO-d$_6$): δ 8.63 (s, 1H), 8.47 (s, 1H), 8.36 (d, J=7.1 Hz, 1H), 8.30 (s, 1H), 7.96 (d, J=7.1 Hz, 1H), 7.62 (t, J=7.1 Hz, 1H), 7.30 (d, J=7.3 Hz, 1H), 7.25 (d, J=7.3 Hz, 1H), 7.04 (t, J=7.3 Hz, 1H), 1.63 (s, 6H).

Embodiment 15. 4-(2-(4,4-dimethyl-1,4-dihydroquinazolin-2-yl)thiazol-4-yl)-3-flurobenzoic acid (I-38)

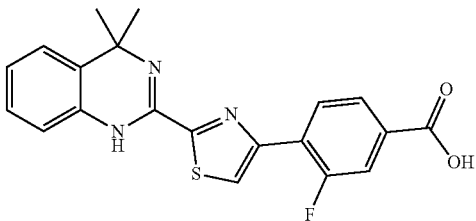

I-38

Compound I-38 was synthesized by referring to the synthesis of compound I-20, in the Suzuki coupling step, 2-fluoro-4-methoxycarbonylphenylboronic acid was used instead of 4-(methoxycaronyl)phenylboronic acid. Compound I-38, LCMS: M+1=382. $^1$H-NMR (400 MHz, DMSO-$d_6$): δ 13.40 (s, 1H), 8.58 (t, J=8.0 Hz, 1H), 8.32 (brs, 1H), 8.00 (br, 1H), 7.92 (dd, J=8.1, 1.3 Hz, 1H), 7.83 (dd, J=11.9, 1.3 Hz, 1H), 7.29 (d, J=7.3 Hz, 1H), 7.19 (t, J=7.0 Hz, 1H), 7.13-7.01 (m, 2H), 1.62 (s, 6H).

Embodiment 16. 4-(2-(4,4-dimethyl-1,4-dihydroquinazolin-2-yl)thiazol-4-yl)-2-flurobenzoic acid (I-40)

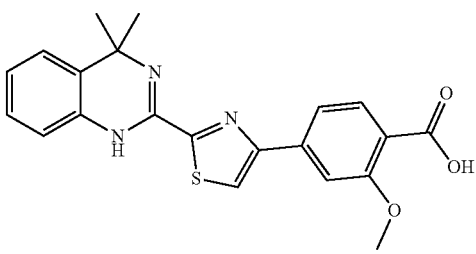

I-40

Compound I-40 was synthesized by referring to the synthesis of compound I-20, in the Suzuki coupling step, 3-methoxyl-4-methoxycarbonylphenylboronic acid was used instead of 4-(methoxycaronyl)phenylboronic acid. Compound I-40, LCMS: M+1=394. $^1$H-NMR (400 MHz, DMSO-$d_6$): δ 12.72 (s, 1H), 8.72 (s, 1H), 7.86 (s, 1H) 7.84 (d, J=8.0 Hz, 2H), 7.78 (d, J=8.0 Hz, 1H), 7.37 (d, J=6.7 Hz, 1H), 7.30-7.23 (m, 2H), 7.21-7.15 (m, 1H), 3.98 (s, 3H), 1.69 (s, 6H).

Embodiment 17. 4'-(8-chloro-4-methyl-1,4-dihydroquinazolin-2-yl)-[1.1'-biphenyl]-4-carboxylic acid (I-43)

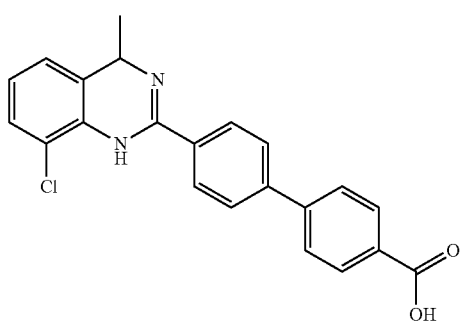

I-43

Compound I-43 was synthesized by referring to the synthesis of compound I-2, in the ring closure step, 4-bromobenzoic acid was used instead of 4-bromothiazole-2-carboxylic acid. Compound I-43, LCMS: M+1=377. $^1$H-NMR (400 MHz, DMSO-$d_6$): δ 13.07 (s, 1H), 8.12 (d, J=7.4 Hz, 2H), 8.06 (d, J=7.4 Hz, 2H), 7.97-7.88 (m, 4H), 7.36 (d, J=6.7 Hz, 1H), 7.18-7.05 (m, 2H), 4.94 (q, J=4.8 Hz, 1H), 1.44 (d, J=4.8 Hz, 3H).

Embodiment 18. 4'-(8-chloro-4,4-dimethyl-1,4-dihydroquinazolin-2-yl)-3'-fluoro-[1.1'-biphenyl]-4-carboxylic acid (I-46)

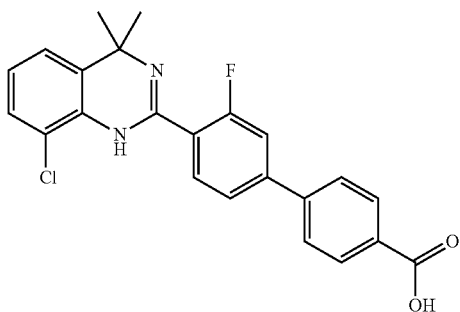

I-46

Compound I-46 was synthesized by referring to the synthesis of compound I-4, in the ring closure step, 4-bromo-2-fluorobenzonitrile was used instead of 4-bromo-2-cyanothiazole. Compound I-46, LCMS: M+1=409. $^1$H-NMR (400 MHz, DMSO-$d_6$): δ 13.16 (s, 1H), 8.12-8.02 (m, 2H), 7.99-7.80 (m, 5H), 7.51-7.38 (m, 2H), 7.32-7.20 (m, 1H), 1.72 (s, 6H).

Embodiment 19. 4-(6-(8-chloro-4,4-dimethyl-1,4-dihydroquinazolin-2-yl)pyridin-3-yl)benzoic acid (I-48)

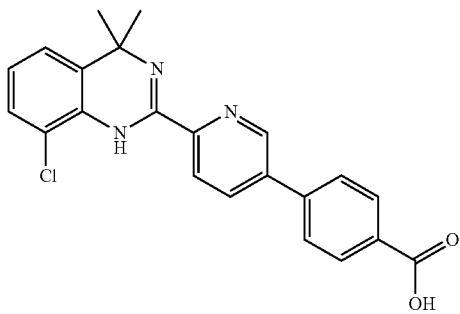

I-48

Compound I-48 was synthesized by referring to the synthesis of compound I-4, in the ring closure step, 5-bromo-2-cyanopyridine was used instead of 4-bromo-2-cyanothiazole. Compound I-48, LCMS: M+1=392. $^1$H-NMR (400 MHz, DMSO-$d_6$): δ 13.13 (s, 1H), 9.09 (s, 1H), 8.53 (d, J=8.2 Hz, 1H), 8.43 (d, J=8.2 Hz, 1H), 8.10 (d, J=8.1 Hz, 2H), 7.98 (d, J=8.1 Hz, 2H), 7.37 (d, J=7.0 Hz, 1H), 7.31 (d, J=7.0 Hz, 1H), 7.10 (t, J=7.8 Hz, 1H), 1.65 (s, 6H).

Embodiment 20. 4-(2-(8-chloro-4,4-dimethyl-1,4-dihydroquinazolin-2-yl)pyrimidin-5-yl)benzoic acid (I-49)

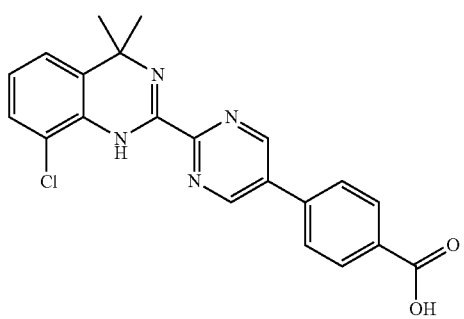

I-49

Compound I-49 was synthesized by referring to the synthesis of compound I-4, in the ring closure step, 5-bromo-2-cyanopyrimidine was used instead of 4-bromo-2-cyanothiazole. Compound I-49, LCMS: M+1=393. $^{1}$H-NMR (400 MHz, DMSO-d$_{6}$): δ 9.34 (s, 2H), 8.26 (s, 1H), 8.08 (d, J=6.8 Hz, 2H), 7.92 (d, J=6.8 Hz, 2H), 7.30 (d, J=5.6 Hz, 1H), 7.25 (d, J=5.6 Hz, 1H), 7.05 (t, J=5.6 Hz, 1H), 1.59 (s, 6H).

Embodiment 21. 4-(5-(8-chloro-4,4-dimethyl-1,4-dihydroquinazolin-2-yl)furan-3-yl)benzoic acid (I-50)

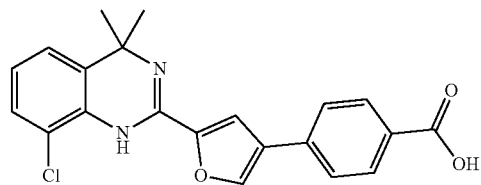

I-50

Compound I-50 was synthesized by referring to the synthesis of compound I-4, in the ring closure step, 4-bromo-2-cyanofuran was used instead of 4-bromo-2-cyanothiazole. Compound I-50, LCMS: M+1=381. $^{1}$H-NMR (400 MHz, DMSO-d$_{6}$): δ 13.04 (s, 1H), 8.85 (s, 1H), 8.27 (s, 1H), 8.03 (d, J=8.1 Hz, 2H), 7.85 (d, J=8.1 Hz, 2H), 7.47 (d, J=7.8 Hz, 1H), 7.40 (d, J=7.8 Hz, 1H), 7.24 (t, J=7.8 Hz, 1H), 1.69 (s, 6H).

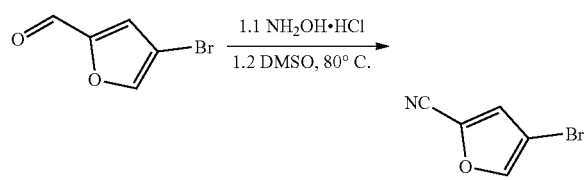

4-Bromo-2-furaldehyde (2.86 mmol) and hydroxylamine hydrochloride (2.2 eq.) were added to dimethyl sulfoxide (3 mL) and stirred for 30 min at room temperature, and TLC detected the disappearance of raw materials. The temperature was raised to 80° C., the reaction was carried out for 2 h, the conversion was detected as complete by TLC. The reaction mixture was poured into water, extracted with methyl tert-butyl ether, and washed with water then dried. The crude product was purified by silica gel chromatography to obtain 4-bromo-2-cyanofuran with a yield of 72%.

Embodiment 22. 4-(5-(8-chloro-4,4-dimethyl-1,4-dihydroquinazolin-2-yl)-1H-pyrrol-3-yl)benzoic acid (I-51)

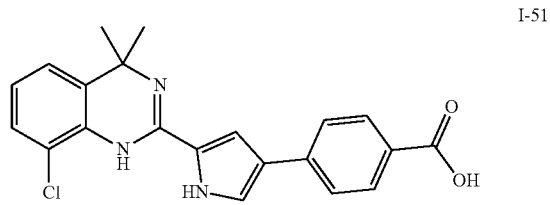 [SMILES: CC1(C)N=C(c2cc(-c3ccc(C(=O)O)cc3)c[nH]2)Nc2c(Cl)cccc21]

I-51

Compound I-51 was synthesized by referring to the synthesis of compound I-50, 4-bromo-2-pyrrolaldehyde was used instead of 4-bromo-2-furanaldehyde. Compound I-51, LCMS: M+1=380. $^{1}$H-NMR (400 MHz, DMSO-d$_{6}$): δ 7.92 (d, J=8.1 Hz, 2H), 7.70 (d, J=8.1 Hz, 2H), 7.55 (s, 1H), 7.40 (s, 1H), 7.26 (d, J=7.6 Hz, 1H), 7.18 (d, J=7.6 Hz, 1H), 6.94 (t, J=7.6 Hz, 1H), 1.52 (s, 6H).

Embodiment 23. 4-(2-(8-chloro-4,4-dimethyl-1,4-dihydroquinazolin-2-yl)oxazol-4-yl)benzoic acid (I-53)

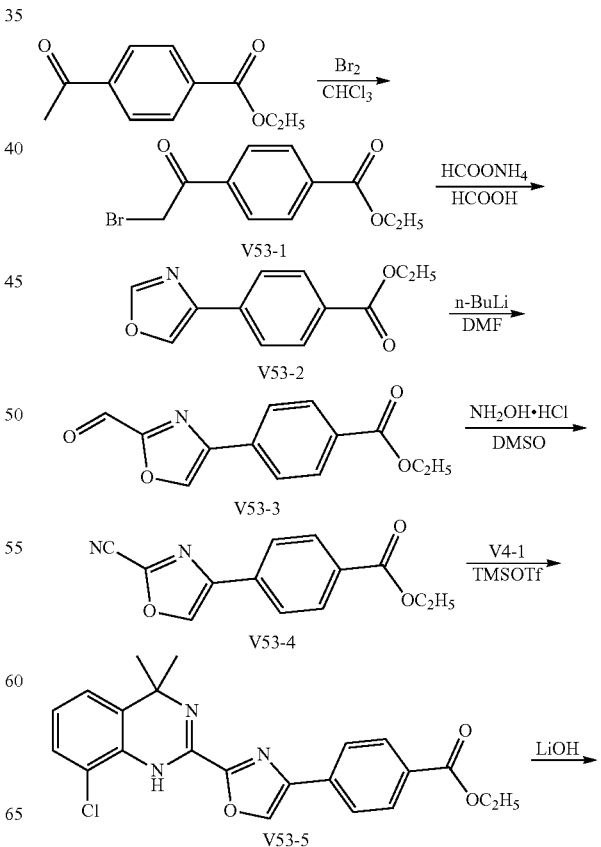

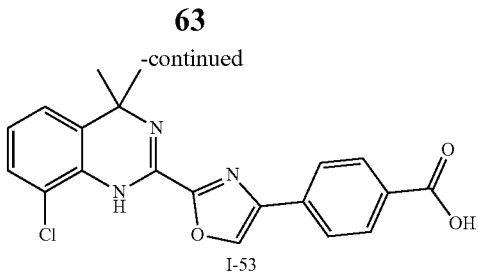

I-53

Synthesis of Intermediate V53-1

Ethyl 4-acetylbenzoate (26.01 mmol) was added to dichloromethane (50 mL), and liquid bromine (1 eq.) was added dropwise at room temperature, after the addition, the reaction was carried out at room temperature for 3 h. TLC detected that most of the raw material was converted, the reaction was washed with water and dried. The crude product was purified by silica gel chromatography to obtain intermediate V53-1 with a yield of 57%. LCMS: M+1=271, 273.

Synthesis of Intermediate V53-2

Intermediate V53-1 (11.07 mmol) and ammonium formate (3 eq.) were added to formic acid (10 mL), and the reaction was carried out at reflux for 3 h, and was detected as complete by TLC. The reaction solution was concentrated to remove most of the formic acid, water was added, the pH value was adjusted to 8-9 by saturated aqueous sodium carbonate solution, then the mixture was extracted with ethyl acetate, washed with water and dried. The crude product was purified by silica gel chromatography to obtain intermediate V53-2 with a yield of 46%. LCMS: M+1=218.

Synthesis of Intermediate V53-3

Intermediate V53-2 (4.60 mmol) was added to dry tetrahydrofuran (10 mL), cooled to −78° C. under nitrogen protection, and n-butyllithium (2.5 M, 1 eq.) was added dropwise and stirred for 30 min after addition. At −78° C., dimethylformamide (2 eq.) was added dropwise and stirred for 30 min, then stirred for 2 h at room temperature. TLC detected that most of the raw material was converted. The reaction solution was quenched by adding to a saturated aqueous ammonium chloride solution, extracted with ethyl acetate, washed with water, and dried. The crude product was purified by silica gel chromatography to obtain V53-3 with a yield of 53%. LCMS: M+1=246.

Synthesis of Intermediate V53-4

The intermediate V53-3 (2.04 mmol) and hydroxylamine hydrochloride (1.2 eq.) were added to dimethyl sulfoxide, the reaction was carried out for 30 min at room temperature, then heated to 80° C. for 2 h, and was detected as complete by TLC. The reaction mixture was poured into water, extracted with ethyl acetate, washed with water and dried. The crude product was purified by silica gel chromatography to obtain V53-4 with a yield of 81%. LCMS: M+1=243.

Synthesis of Intermediate V53-5

Intermediate V53-4 (0.54 mmol), intermediate V4-1 (2-(2-amino-3-chlorophenyl)propyl-2-ol, 1 eq.) were placed in a sealed tube, trimethylsilyl trifluoromethanesulfonate (3 mL) was added, and the reaction was carried out at 120° C. for 5 h, and the reaction was detected as complete by TLC. The reaction mixture was poured into water, and adjusted to basic by adding sodium bicarbonate, and the crude product was purified by silica gel chromatography to obtain intermediate V53-5 with a yield of 36%. LCMS: M+1=410.

Synthesis of Compound I-53

Intermediate V53-5 (0.19 mmol) was dissolved in tetrahydrofuran (5 mL) and methanol (1 mL), lithium hydroxide (2 eq) aqueous solution (1 mL) was added with stirring at room temperature, and the reaction was carried out at room temperature overnight, and was detected as complete by TLC. The solvent was evaporated, 5 mL of water was added to the mixture, the pH value was adjusted with 1 M hydrochloric acid to 5-6, filtered and oven-dried to obtain compound I-53 with a yield of 79%. LCMS: M+1=382. $^1$H-NMR (400 MHz, DMSO-$d_6$): δ 13.04 (s, 1H), 8.62 (s, 1H), 8.45 (s, 1H), 8.29 (d, J=8.2 Hz, 2H), 8.08 (d, J=8.2 Hz, 2H), 7.35 (d, J=7.6 Hz, 1H), 7.29 (d, J=7.6 Hz, 1H), 7.10 (t, J=7.6 Hz, 1H), 1.65 (s, 6H).

Embodiment 24. 4-(2-(4,4-dimethyl-1,4-dihydroquinazolin-2-yl)-1H-imidazol-4-yl)benzoic acid (I-54)

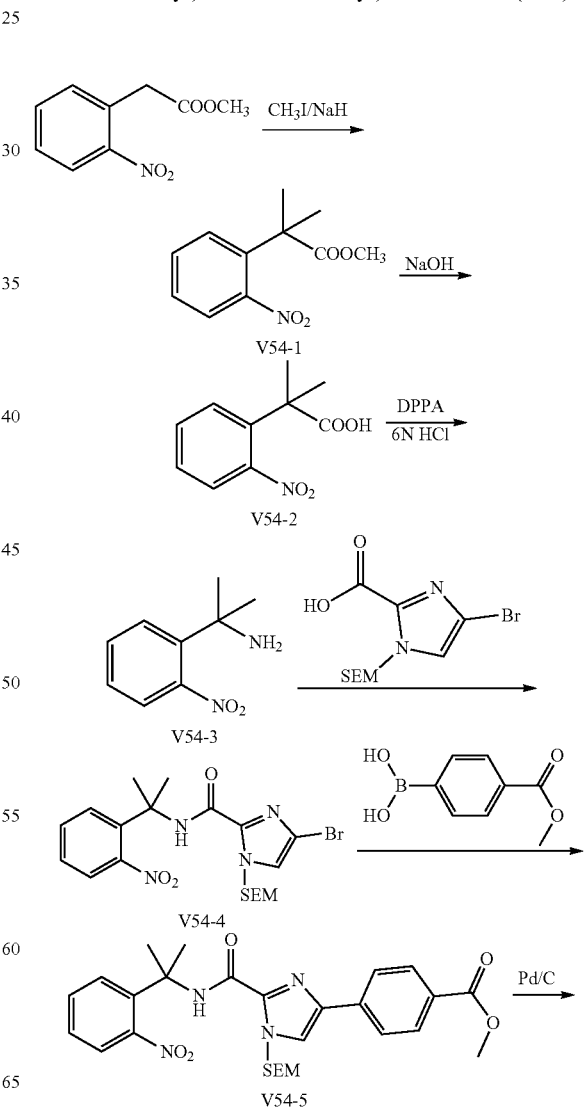

-continued

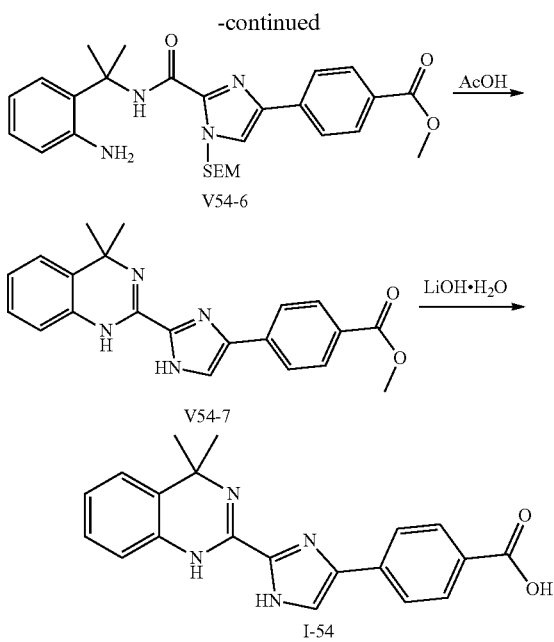

Synthesis of Intermediate V54-1

031-A (25 g, 128 mmol, 1.0 eq), iodomethane (54 g, 380.3 mmol, 3.0 eq), 200 mL of N, N-dimethylformamide were added into a 500 mL flask, the mixture was stirred, cooled down to −30° C., then NaH (15 g, 380.3 mmol, 3.0 eq) was slowly added in batches, the mixture was then stirred at room temperature for 3 hours after addition, and the reaction conversion detected by TLC was about 40%. The reaction solution was quenched by slowly pouring into ice water, extracted by MTBE, and the crude product was dried and concentrated, then slurried with PE/EA (5:1) to obtain intermediate V54-1 of 8.5 g with a yield of 30%. LCMS: M+1=224.

Synthesis of Intermediate V54-2

Intermediate V54-1 (8 g, 35.84 mmol, 1.0 eq), 40 mL of methanol, 3N sodium hydroxide solution (24 mL, 2.0 eq) were added into 250 mL flask, the mixture was stirred, heated to 85° C. and the reaction was carried out overnight, the reaction was detected as complete by TLC, then the mixture was concentrated under reduced pressure to remove methanol, 50 mL of water was added thereto and extracted once with 100 mL methyl tert-butyl ether, the aqueous phase was cooled to 5° C., 6 N hydrochloric acid was added dropwise to adjust the pH value to 3-5, then the mixture was stirred for 30 min, filtered and dried to obtain 7 g of product with a yield of 93%. LCMS: M+1=210.

Synthesis of Intermediate V54-3

V54-2 (7 g, 33.5 mmol, 1.0 eq) and 100 mL of toluene were added into a 500 mL flask, the mixture was stirred and cooled to 0° C., triethylamine (4.06 g, 40.2 mmol, 1.2 eq) was added dropwise, after addition, DPPA (10.13 g, 36.84 mmol, 1.1 eq) was added dropwise, the temperature was raised to 20° C. for 3 hours, the reaction was detected as complete by TLC, then heated to reflux and the reaction was carried out for 2 h, then was detected as complete by TLC, cooled to room temperature, and 100 mL of 6N hydrochloric acid was added thereto, then heated to reflux and stirred for 3 h, the reaction was detected as complete by TLC, the aqueous phase was separated and washed once with 50 mL of ethyl acetate, extracted once with 50 mL of organic phase, the aqueous phase was combined, and the pH value was adjusted to 9-10, the mixture was extracted twice with 100 mL of ethyl acetate, dried, and evaporated to dryness to obtain 4.5 g of product with a yield of 75%. LCMS: M+1=181.

Synthesis of Intermediate V54-4

4-Bromo-1-((2-(trimethylsilyl)ethoxy)methyl)-1H-imidazol-2-carboxylic acid (3 g, 9.34 mmol, 1.1 eq), HATU (6.43 g, 16.92 mmol, 2.0 eq), triethylamine (2.57 g, 25.4 mmol, 3.0 eq), 20 mL of dichloromethane were added into a 100 mL flask, the mixture was stirred for 30 min, V54-3 (1.5 g, 8.33 mmol, 1.0 eq) was added thereto, then heated to 30° C. and the reaction was carried out overnight, and was detected as complete by TLC, 20 mL of water was added to the mixture and extracted with 20 mL of dichloromethane twice, dried, and the crude product was purified by silica gel column chromatography to obtain 2 g of product with a yield of 50%. LCMS: M+1=483, 485.

Synthesis of Intermediate V54-5

V54-4 (1.5 g, 3.11 mmol, 1.0 e q), 4-(methoxycarbonyl)phenylboronic acid (0.67 g, 3.73 mmol, 1.2 eq), anhydrous potassium carbonate (0.86 g, 6.21 mmol, 2.0 eq), 30 mL of tetrahydrofuran and 6 mL of water were added to a 100 mL flask, the mixture was stirred, under nitrogen protection, Pd(dppf)Cl$_2$ (227 mg, 0.31 mmol, 10% eq) was added thereto, and the mixture was heated to 75° C., the reaction was carried out overnight, and was detected as complete by TLC, 30 mL of water and 30 mL of ethyl acetate were added, stirred, the organic phase was separated and dried, and the crude product was purified by column chromatography to obtain 1.6 g of product with a yield of 96%. LCMS: M+1=539.

Synthesis of Intermediate V54-6

Intermediate V54-5 (120 mg, 1.0 eq), 10 mL of methanol, 10% Pd/C 30 mg were added in a 100 mL flask, the mixture was stirred and reduced by hydrogen gas, then stirred overnight at room temperature, the reaction was detected as complete by TLC, tetrahydrofuran was added, filtered, the filter cake washed with methanol, evaporated to obtain 120 mg of crude product, which was directly used in the next reaction step. LCMS: M+1=509.

Synthesis of Intermediate V54-7

Intermediate V54-6 (120 mg) was added to a 25 mL flask, glacial acetic acid 4 mL was added thereto, the mixture was heated to 105° C. and the reaction was carried out for 3 hours, and was detected as complete by TLC, then evaporated to dryness, 10 mL of ethyl acetate was added, and washed once with saturated sodium bicarbonate, and once with saturated saline, dried, and evaporated to dryness to obtain 100 mg of the crude product, which was directly used in the next reaction step. LCMS: M+1=361.

Synthesis of compound I-54

Intermediate V54-7 (100 mg, 0.28 mmol, 1.0 eq), 4 mL tetrahydrofuran, 1 mL of methanol were added into 25 mL flask, lithium hydroxide monohydrate (35 mg, 0.83 mmol, 3.0 eq) and 0.6 mL of water were added thereto, the mixture was heated to 30° C. and stirred overnight, and the reaction was detected as complete by TLC, the mixture was evaporated to dryness, 5 mL of water was added, the mixture was extracted with 2 mL of ethyl acetate once, 2N hydrochloric acid was added dropwise to the aqueous phase to adjust the pH value to 5-6, a solid was precipitated, the mixture was stirred for 10 min, filtered and dried to obtain 50 mg of product with a three-step yield of 65%. LCMS: M+1=347. $^1$H-NMR (400 MHz, DMSO-d6): δ 8.07-8.03 (m, 1H), 8.02-7.95 (m, 1H), 7.32 (d, J=7.6 Hz, 1H), 7.26-7.18 (m, 1H), 7.13-7.07 (m, 1H), 1.63 (s, 6H).

Embodiment 25. 4-(2-(4,4-dimethyl-8-trifluoromethoxyl-1,4-dihydroquinazolin-2-yl)thiazol-4-yl)benzoic acid (I-65)

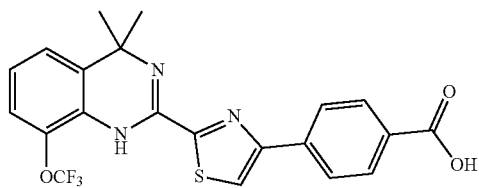

I-65

Compound I-65 was synthesized by referring to the synthesis of compound I-23, methyl 2-amino-3-trifluoromethoxylbenzoic acid was used instead of methyl 2-amino-3-trifluorobenzoic acid. Compound I-65, LCMS: M+1=448. $^1$H-NMR (400 MHz, DMSO-d6): δ 8.50 (s, 1H), 8.31 (s, 1H), 8.26 (d, J=7.9 Hz, 2H), 8.05 (d, J=7.9 Hz, 2H), 7.33 (d, J=7.3 Hz, 1H), 7.20 (d, J=7.3 Hz, 1H), 7.14 (t, J=7.3 Hz, 1H), 1.64 (s, 6H).

Embodiment 26. 4-(2-(4,4-dimethyl-1,4-dihydroquinazolin-2-yl)-1H-imidazol-4-yl)-N-(methylsulfonyl)benzamid (I-66)

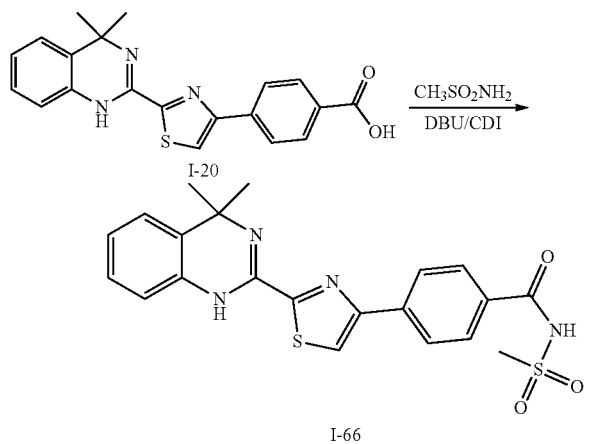

Compound I-20 (25 g, 68.8 mmol, 1.0 eq) and 250 mL of tetrahydrofuran were added to 1 L reaction flask, the mixture was stirred, CDI (33.5 g, 206.6 mmol, 3.0 eq) was added thereto, the temperature was raised to 30° C. and the mixture was stirred for 1 h, methanesulfonamide (9.8 g, 103 mmol, 1.5 eq), DBU (31.5 g, 206.6 mmol, 3.0 eq) were added, and the reaction was carried out overnight at 30° C. The reaction was detected as complete by TLC, water was added to the mixture and the mixture was extracted with 150 mL of ethyl acetate, then stirred to separate the layers, 2N hydrochloric acid was added to the water phase to adjust the pH value to 5-6, and a solid was precipitated, the mixture was stirred for 2 h, filtered and dried to obtain 40 g of crude product.

The crude product was slurried twice with methanol, filtered and dried to obtain 22 g of product with a yield of 73.3%, LCMS: M+1=441. $^1$H-NMR (400 MHz, DMSO-d6): δ 12.35 (s, 1H), 10.88 (s, 1H), 8.94 (s, 1H), 8.35 (d, J=8.4 Hz, 2H), 8.13 (d, J=8.4 Hz, 2H), 7.55-7.49 (m, 2H), 7.40 (t, J=7.1 Hz, 1H), 7.34 (t, J=7.4 Hz, 1H), 3.18 (s, 3H), 1.82 (s, 6H).

Embodiment 27. 4-(2-(4,4-dimethyl-4H-benzo[d][1,3]oxazin-2-yl)thiazol-4-yl)benzoic acid (I-67)

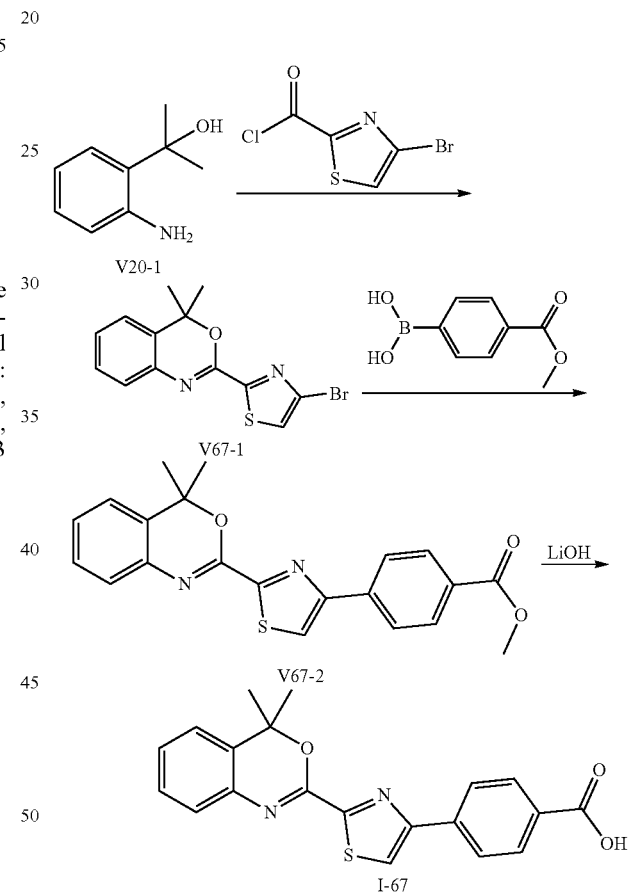

Synthesis of Intermediate V67-1

315 g of thionyl chloride was added in a 500 mL flask, 4-bromothiazole-2-carboxylic acid (45 g, 0.216 mol, 1.5 eq) was added with stirring, the mixture was heated to 75° C., DMF (0.6 mL) was added thereto, and the reaction was carried out for 3 hours. The reaction solution was evaporated to dryness, replaced twice with 200 mL of dichloromethane, then 200 mL of dichloromethane was added, and cooled to 0-5° C., boron trifluoride ether (41 g, 0.288 mol, 2 eq) was added dropwise, a mixed solution of V20-1 (21.8 g, 0.144 mol, 1.0 eq) and 70 mL of dichloromethane was then added dropwise, after the addition, the mixture was stirred at 0-5° C. for 30 minutes, and heated to 50° C. and the reaction was carried out overnight. The reaction was detected as complete by TLC, 200 mL of 10% sodium hydroxide solution was slowly added dropwise to adjust the pH value to 8-9, the organic phase was separated and the aqueous phase was extracted once with 50 mL of dichloromethane, the organic phase was combined and dried, evaporated to dryness to obtain 55 g of crude product.

75 mL of ethyl acetate was added to the crude product, heated to 50° C. for dissolution, 200 mL of petroleum ether was added dropwise, a solid was precipitated, the mixture was stirred at room temperature for 1 hour, then stirred at 0-5° C. for 30 minutes, filtered and dried to obtain 25.8 g of off-white solid with a yield of 55.4% and LCMS: m+1=324.

Synthesis of Intermediate V67-2

V67-1 (25.8 g, 79.9 mmol, 1.0 eq), 4-(methoxycarbonyl) phenylboronic acid (14.4 g, 79.9 mmol, 1.0 eq), potassium carbonate (22.1 g, 160 mmol, 2.0 eq), 260 mL of tetrahydrofuran and 52 mL of water were added to a 500 mL flask, under nitrogen protection, Pd(dppf)Cl₂ (2.95 g, 4 mmol, 5% eq) was added thereto, and the mixture was heated to 75° C. in an oil bath, the reaction was carried out overnight. The reaction was detected as complete by TLC, 100 mL of water was added, the mixture was extracted with 100 mL ethyl acetate twice, the organic phase was combined and dried, purified by column chromatography to obtain the product with a yield of 95.3%, LCMS: M+1=379.

Synthesis of Compound I-67

V67-2 (18.4 g, 48.6 mmol, 1.0 eq), 92 mL of tetrahydrofuran, 36.8 mL of methanol were added in a 250 mL flask, the mixture was stirred, then lithium hydroxide monohydrate (4.1 g, 97.2 mmol, 2.0 eq) was added thereto, 36.8 mL of water was added, the temperature was raised to 30-35° C. and the reaction was stirred for 4 hours. The reaction solution was evaporated to dryness, 90 mL of water was added, 4N hydrochloric acid was added dropwise to adjust the pH value to 4-5, after the addition, the mixture was stirred at room temperature for 30 minutes, filtered and evaporated to dryness to obtain 35 g of wet product.

210 mL of ethanol (6V) was added to the wet product, stirred, heated to 55° C. and stirred for 1 hour, then cooled to room temperature and stirred for another 3 hours, filtered and evaporated to dryness to obtain 17 g of product with a yield of 96%, LCMS: M+1=365. ¹H-NMR (400 MHz, DMSO-d6): δ 8.59 (s, 1H), 8.16 (d, J=8.4 Hz, 2H), 8.07 (d, J=8.4 Hz, 2H), 7.43-7.32 (m, 3H), 7.28 (dd, J=7.4, 1.3 Hz, 1H), 1.74 (s, 6H).

Embodiment 28. 4-(2-(4,4-dimethyl-4H-benzo[e][1,3]oxazin-2-yl)thiazol-4-yl)benzoic acid (I-68)

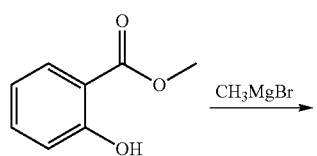

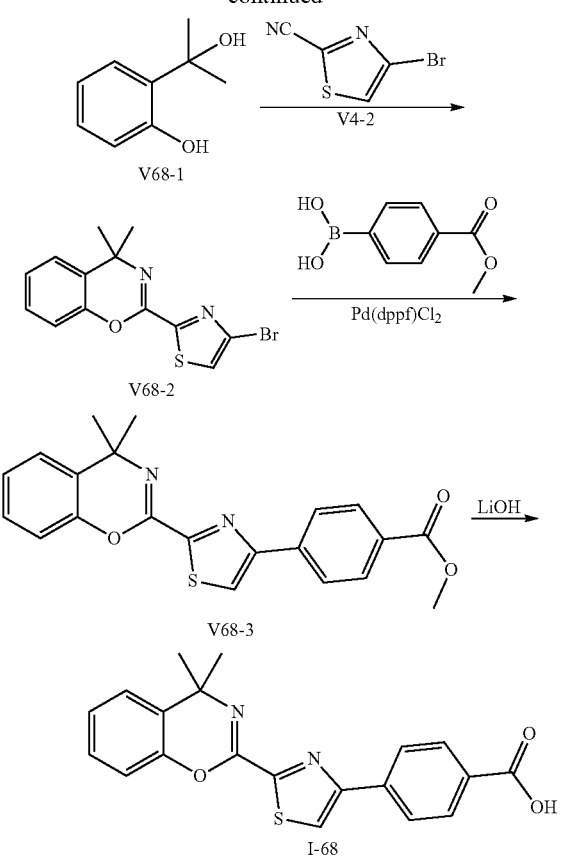

Compound I-68 was synthesized by referring to the synthesis of compound I-20, methyl 2-hydroxybenzoate was used instead of methyl 2-aminobenzoate. LCMS: M+1=365. ¹H-NMR (400 MHz, DMSO-d₆): δ 8.56 (s, 1H), 8.17 (d, J=8.5 Hz, 2H), 8.08 (d, J=8.5 Hz, 2H), 7.48 (dd, J=7.6, 1.5 Hz, 1H), 7.35 (td, J=7.8, 1.6 Hz, 1H), 7.26 (td, J=7.5, 1.2 Hz, 1H), 7.21 (dd, J=8.0, 1.0 Hz, 1H), 1.60 (s, 6H).

Embodiment 29. 4-(2-(4,4-diethyl-1,4-dihydroquinazolin-2-yl)thiazol-4-yl)benzoic acid (I-69)

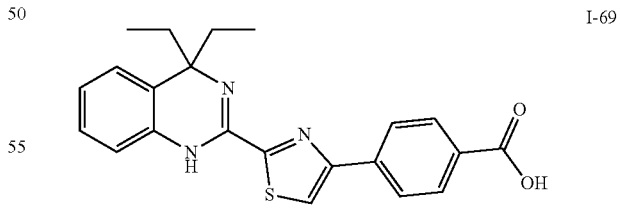

Compound I-69 was synthesized by referring to the synthesis of compound I-20, wherein, in the Grignard reaction step, ethylmagnesium bromide was used instead of methylmagnesium bromide. LCMS: M+1=378. ¹H-NMR (400 MHz, DMSO-d6): δ 13.07 (s, 1H), 8.53 (s, 1H), 8.28 (d, J=8.4 Hz, 2H), 8.06 (d, J=8.4 Hz, 2H), 7.17 (d, J=7.4 Hz, 2H), 7.08 (t, J=7.4 Hz, 2H), 1.88 (d, J=5.9 Hz, 4H), 0.76 (t, J=7.1 Hz, 6H).

Embodiment 30. 4-(2-(6,8-difluoro-4,4-dimethyl-1,4-dihydroquinazolin-2-yl)thiazol-4-yl)benzoic acid (I-70)

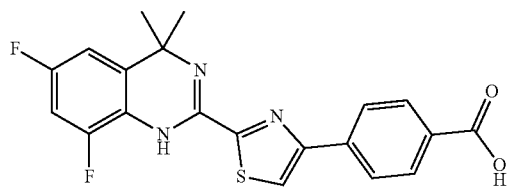

Compound I-70 was synthesized by referring to the synthesis of compound I-4, methyl 2-amino-3,5-difluorobenzoate was used instead of methyl 2-amino-3-chlorobenzoate. LCMS: M+1=400. $^1$H-NMR (400 MHz, DMSO-d6): δ 13.11 (s, 1H), 8.54 (s, 1H), 8.29 (d, J=8.5 Hz, 2H), 8.19 (s, 1H), 8.06 (d, J=8.5 Hz, 2H), 7.16-7.09 (m, 2H), 1.65 (s, 6H).

Embodiment 31. 4-(2-(4,4-dimethyl-1,4-dihydroquinazolin-2-yl)thiazol-4-yl)benzamide (I-71)

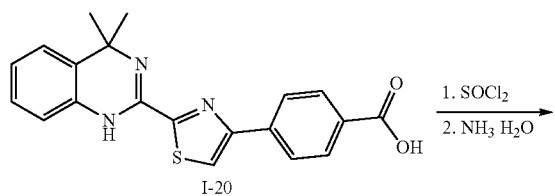

20 mL of dichloromethane was added into a 100 mL single-neck flask, compound I-20 (200 mg, 0.55 mmol) was added with stirring, then thionyl chloride (327 mg, 2.75 mmol, 5 eq) was added dropwise, the mixture was refluxed for 3 h, concentrated and dried, dissolved in tetrahydrofuran, and was added dropwise into 20 mL concentrated ammonia in an ice bath, after the addition, the mixture was stirred at room temperature for 2 h, extracted by ethyl acetate, dried and concentrated to obtain 150 mg of the product with a yield of 75%. LCMS: M+1=363. $^1$H-NMR (400 MHz, DMSO-d6): δ 8.46 (s, 1H), 8.24 (d, J=8.4 Hz, 2H), 8.09 (s, 1H), 8.01 (d, J=8.4 Hz, 2H), 7.96 (s, 1H), 7.46 (s, 1H), 7.31-7.26 (m, 1H), 7.18 (td, J=7.6, 1.3 Hz, 1H), 7.08 (td, J=7.6, 1.3 Hz, 1H), 7.06-7.02 (m, 1H), 1.62 (s, 6H).

Embodiment 32. 4-(4-(1H-tetrazol-5-yl)-2-(4,4-dimethyl-1,4-dihydroquinazolin-2-yl)thiazole (I-72)

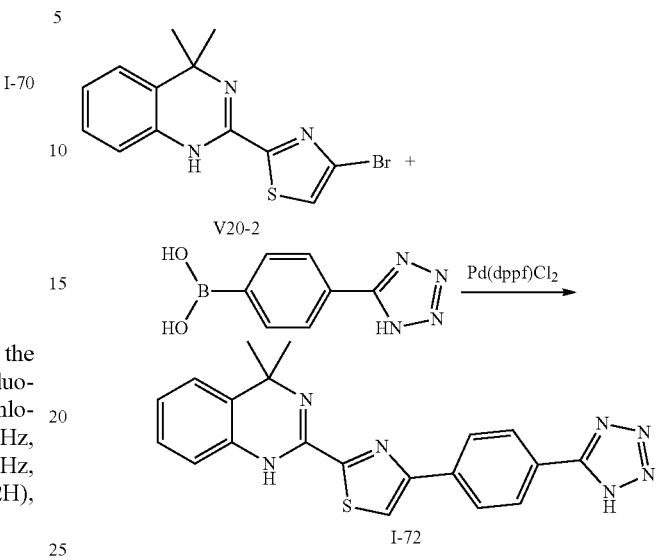

V20-2 (200 mg, 0.62 mmol, 1.0 eq), 4-(1H-tetrazol-5-yl phenylboronic acid (141.5 mg, 0.745 mmol, 1.2 eq), tripotassium phosphate (395 mg, 1.86 mmol, 3.0 eq), 10 mL of n-butanol and 2 mL of water were added to a 50 mL bottle, the mixture was stirred, under nitrogen protection, Pd(PPH$_3$)$_4$ (35.8 mg, 0.03 mmol, 5% eq) was added thereto, and the mixture was heated to 110° C. for 5 h, the reaction was detected as complete by TLC, then cooled to room temperature, 100 mL of water was added thereto, and was extracted with 20 mL ethyl acetate twice, dried and the crude product was purified by column chromatography to obtain 30 mg of off-white product with a yield of 12.5%, LCMS: M+1=388. $^1$H-NMR (400 MHz, DMSO-d6): δ 8.46 (s, 1H), 8.35 (d, J=8.4 Hz, 2H), 8.16 (d, J=8.4 Hz, 2H), 7.29 (dd, J=7.6, 1.4 Hz, 1H), 7.19 (td, J=7.6, 1.4 Hz, 1H), 7.11-7.05 (m, 2H), 1.62 (s, 6H).

Embodiment 33. 4-(2-(4,4-dimethyl-1,4-dihydroquinazolin-2-yl)thiazol-4-yl)benzamide (I-73)

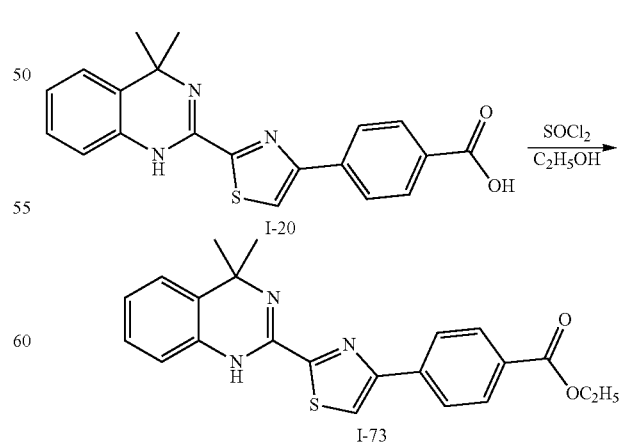

20 mL of ethanol was added to a 100 mL single-neck flask, compound I-20 (200 mg, 0.55 mmol) was added with stirring, then thionyl chloride (327 mg, 2.75 mmol, 5 eq) was added dropwise, the mixture was refluxed for 3 hours, concentrated to remove the solvent, and 30 mL of ethyl acetate was added thereto, the mixture was then washed with saturated sodium bicarbonate, dried and concentrated, the crude product was purified by silica gel column chromatography to obtain 110 mg of the product with a yield of 51%. LCMS: M+1=392. 1H-NMR (400 MHz, DMSO-d6): δ 8.93 (s, 1H), 8.35 (d, J=8.6 Hz, 2H), 8.12 (d, J=8.6 Hz, 2H), 7.57 (d, J=7.6 Hz, 1H), 7.52 (dd, J=7.6, 1.1 Hz, 1H), 7.40 (td, J=7.6, 1.1 Hz, 1H), 7.34 (td, J=7.6, 1.1 Hz, 1H), 4.37 (q, J=7.1 Hz, 2H), 1.82 (s, 6H), 1.37 (t, J=7.1 Hz, 3H).

Embodiment 34. 4-(2-(8-chloro-4-oxo-1,4-dihydroquinolin-2-yl)thiazol-4-yl)benzoic acid (I-13)

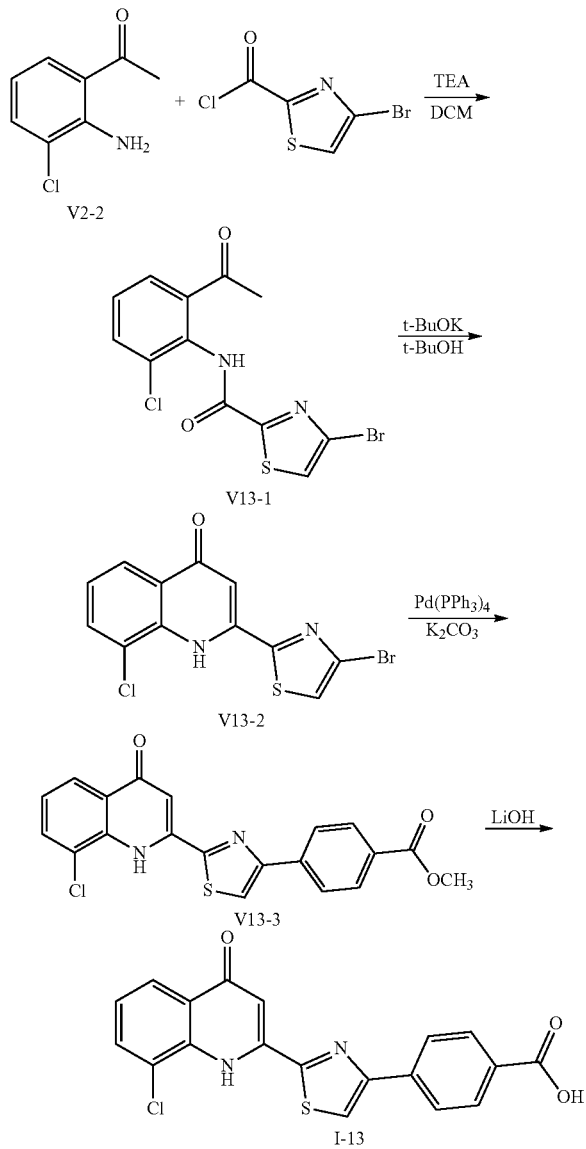

Synthesis of Intermediate V13-1

4-Bromo-2-thiazolecarboxylic acid (4.81 mmol) was added to dichloromethane, one drop of dimethylformamide was added to catalyze, and oxalyl chloride (2.0 eq.) was added dropwise, after the addition, the reaction was carried out at room temperature for 2 h, and was detected as complete by TLC. The reaction solution was concentrated to dryness and dissolved in tetrahydrofuran (10 mL) for later use.

Intermediate V2-2 (1.0 eq.) was added to dry tetrahydrofuran, triethylamine (6.0 eq.) was added, and the mixture was stirred and dissolved, and the tetrahydrofuran solution with acyl chloride from the previous step was added dropwise at room temperature, after the addition, the reaction was carried out at 70° C. for 4 h, and the reaction was detected as complete by TLC. the reaction was washed with water, the crude product was purified by silica gel chromatography to obtain intermediate V13-1 with a yield of 53%. LCMS: M+1=359, 361.

Synthesis of Intermediate V13-2

Intermediate V13-1 (2.22 mmol) was added to dry tert-butanol (20 mL), potassium tert-butoxide (5.0 eq.) was added in batches, after the addition, the reaction was carried out at 60° C. for 5 h, and was detected as complete by TLC. The tert-butanol was concentrated, 10 mL of water was added, and the pH value was adjusted to 4-5 with 2M hydrochloric acid, the mixture was filtered, and the filter cake was washed with water and dried to obtain intermediate V13-2 with a yield of 39%. LCMS: M+1=341, 343.

Synthesis of Intermediate V13-3

The intermediates V13-2 (0.23 mmol), 4-(methoxycarbonyl)phenylboric acid (1.1 eq.), potassium carbonate (2.0 eq.), tetrakis(triphenylphosphine)palladium (5% eq.) were placed in a flask under nitrogen protection. Tetrahydrofuran (5 mL) and water (1 mL) were added and refluxed at 80° C. overnight, and the reaction was detected as complete by TLC. Water was added to the mixture, the mixture was extracted with ethyl acetate, and the crude product obtained was purified by silica gel chromatography to obtain intermediate V13-3 with a yield of 61%. LCMS: M+1=397.

Synthesis of Compound I-13

Intermediate V13-3 (0.17 mmol) was dissolved in tetrahydrofuran (5 mL) and methanol (1 mL), lithium hydroxide (2 eq) aqueous solution (1 mL) was added with stirring at room temperature, and the reaction was carried out at room temperature overnight, and was detected as complete by TLC. The solvent was evaporated, 5 mL of water was added to the mixture, the pH value was adjusted with hydrochloric acid to 5-6, filtered and oven-dried to obtain a yellow solid with a yield of 67%. LCMS: M+1=383. $^1$H-NMR (400 MHz, DMSO-d$_6$): δ 13.06 (s, 1H), 8.70 (s, 1H), 8.22-8.15 (m, 3H), 8.09-8.04 (m, 4H), 7.57-7.54 (m, 1H), 7.38 (s, 1H).

Embodiment 35. 4'-(8-chloro-4-oxo-4H-benzopyran-2-yl)-[1.1'-biphenyl]-4-carboxylic acid (I-14)

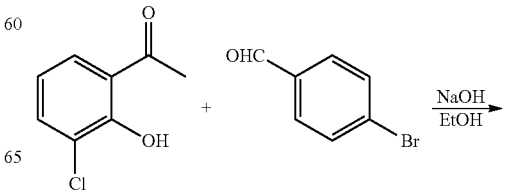

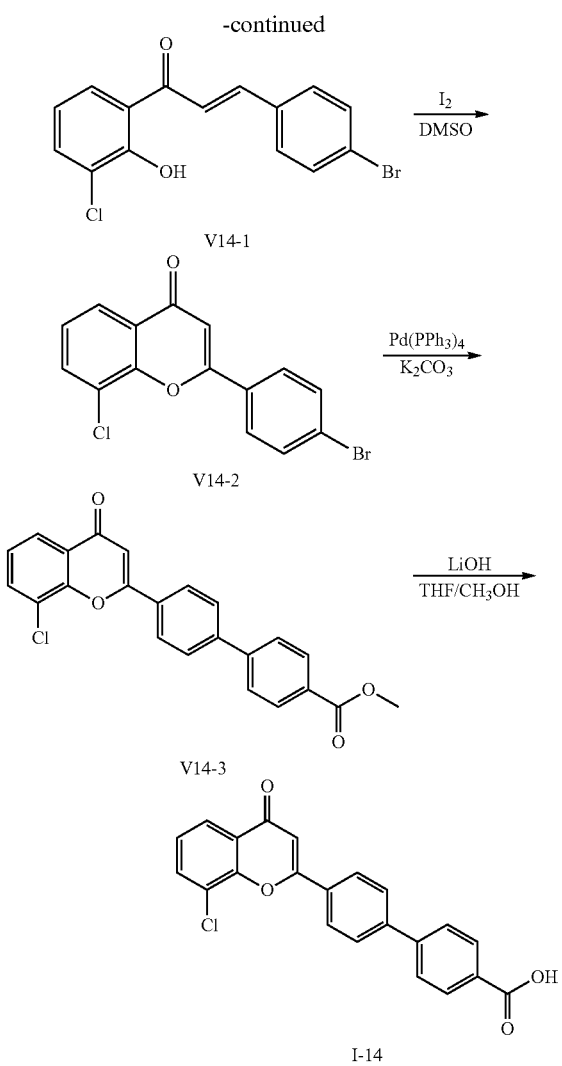

Synthesis of Intermediate 14-1

3-Chloro-2-hydroxyacetophenone (11.72 mmol) and 4-bromobenzaldehyde (1.0 eq.) was dissolved in ethanol (20 mL), and 40% aqueous sodium hydroxide solution (2.5 eq.) was added dropwise with stirring at room temperature. After the addition, the reaction mixture was stirred and the reaction was carried out overnight, and the raw material was completely converted as detected by TLC. 20 mL of water was added to the reaction solution, the pH value was adjusted to 4-6 with 6M hydrochloric acid, the mixture was extracted with ethyl acetate, and dried. The crude product was purified by silica gel chromatography to obtain intermediate 14-1 with a yield of 71%. LCMS: M+1=337, 339.

Synthesis of Intermediate 14-2

Intermediate 14-1 (7.41 mmol) and iodine (0.1 eq.) were added to dimethyl sulfoxide (20 mL), the mixture was stirred at an external temperature of 100° C. for 1 h, and the raw material was completely converted as detected by TLC. Water (50 mL) was added to the reaction mixture, the mixture was extracted with ethyl acetate, washed with saturated aqueous sodium thiosulfate solution, and dried. The crude product was purified by silica gel chromatography to obtain intermediate 14-2 with a yield of 64%. LCMS: M+1=335, 337.

Synthesis of Intermediate 14-3

Intermediate 14-2 (0.30 mmol), 4-(methoxycarbonyl)phenylboric acid (1.1 eq.) and potassium carbonate (2 eq.) were added to tetrahydrofuran (5 mL) and water (0.5 mL), and bubbled with nitrogen for 2 min. Tetrakis(triphenylphosphine)palladium (0.1 eq) was added, and bubbled with nitrogen for 3 min. The reaction was carried out at 70° C. for 5 h, the conversion was detected as complete by TLC. Water was added to the mixture, and the mixture was extracted with ethyl acetate, then dried. The crude product was purified by silica gel chromatography to obtain intermediate 14-3 with a yield of: 48%. LCMS: M+1=391.

Synthesis of Compound I-14

Intermediate V14-3 (0.14 mmol) was dissolved in tetrahydrofuran (5 mL) and methanol (1 mL), lithium hydroxide (2 eq) aqueous solution (1 mL) was added with stirring, and the reaction was carried out at room temperature overnight, and was detected as complete by TLC. The solvent was evaporated, 5 mL of water was added to the mixture, the pH value was adjusted with hydrochloric acid to 5-6, filtered and oven-dried to obtain compound I-14, with a yield of 55%. LCMS: M+1=377. $^1$H-NMR (400 MHz, DMSO-$d_6$): δ 13.07 (s, 1H), 8.24 (d, J=7.9 Hz, 2H), 8.08-7.96 (m, 6H), 7.92 (d, J=7.9 Hz, 2H), 7.50 (t, J=7.7 Hz, 1H), 7.24 (s, 1H).

Embodiment 36. 4-(2-(8-chloro-4-oxo-4H-benzopyran-2-yl)thiazol-4-yl)benzoic acid (I-19)

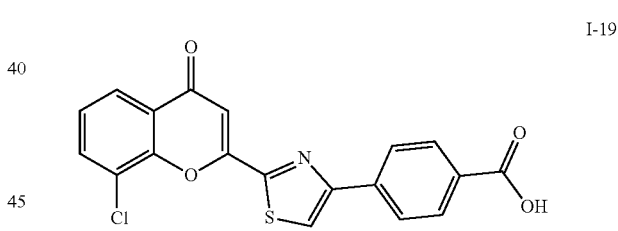

I-19

Compound I-19 was synthesized by referring to the synthesis of compound I-14, 4-bromothiazole-2-carbaldehyde was used instead of 4-bromobenzaldehyde. Compound I-19, LCMS: M+1=384. $^1$H-NMR (400 MHz, DMSO-$d_6$): δ 13.04 (s, 1H), 8.79 (s, 1H), 8.23 (d, J=7.9 Hz, 2H), 8.08-8.03 (m, 4H), 7.56 (t, J=7.9 Hz, 1H), 7.23 (s, 1H).

Effect Embodiment 1: Cryopreserved Primary Human Hepatocyte Assay (Cryopreserved PHH Assay)

1. Experimental Objectives:

The inhibitory effect of the compounds on HBV was evaluated by real-time quantitative qPCR assay (real time-qPCR) to detect the HBV DNA content in human primary hepatocytes (PHH) culture supernatant, and ELISA to detect the hepatitis B surface antigen and e antigen content, the $EC_{50}$ value of the compounds was used as an indicator; meanwhile, the cell viability was detected by CellTiter-Glo to evaluate the toxicity of the compounds to cells.

2. Experimental Materials:
2.1 Cells: Frozen human primary hepatocytes (PHH)
2.2 Reagents:
Dimethyl sulfoxide (DMSO), CellTiter-Glo, high-throughput DNA purification kit, quantitative quick-start universal probe reagent, hepatitis B surface antigen quantitative detection kit, hepatitis B e antigen quantitative detection kit.
2.3 Consumables and instruments:
48-well cell culture plate, $CO_2$ incubator, quantitative PCR 96-well plate, fluorescence quantitative PCR instrument, microplate reader.
3. Experimental steps and methods:
3.1. On day 0, PHH ($1.32 \times 10^5$ cells/well) was seeded into a 48-well plate and incubated overnight at 37° C., 5% $CO_2$.
3.2. On the first day, PHH was infected with type D HBV (concentrated from HepDE19 cell culture supernatant).
3.3 On the second day, the test compound was diluted to 7 concentrations with 5-fold serial dilution. Reference compound Peg-IFN-α 2a, 7 concentrations with 3-fold serial dilution. Compounds with different concentrations were added to the culture wells, and the wells were double-duplicated wells. The final concentration of DMSO in the culture medium was 2%.
3.4 On the 4th, 6th, and 8th day, the culture medium was replaced by a fresh culture medium containing the compound.
3.5 After collecting the culture supernatant from the culture well on the 10th day, the cell viability was tested with CellTiter-Glo. A portion of the culture supernatant was collected for ELISA determination to detect the content of hepatitis B virus surface antigen and e antigen; a portion of the sample was collected for extract DNA using a high-throughput DNA purification kit, referring to the product instructions for the specific steps.
3.6 Quantitative PCR to detect the content of HBV DNA
The qPCR reaction mixture, sample and standard were added to the 384 well reaction plate. PCR reactions: 95° C., 10 min; 95° C., 15 sec, 60° C., 1 min, 40 cycles.
3.7 ELISA determination of hepatitis B virus surface antigen and e antigen
The specific steps can be referred to the product manual, the steps are briefly described as follows: 50 μL of sample and standard was added to the reaction plate respectively, 50 μL of enzyme conjugate was added to each well, the mixture was shaken and mixed well, then kept in a warm bath at 37° C. for 60 minutes, the plate was washed with washing solution for 5 times, 50 μL of the luminescent substrate was added to each well, the mixture was mixed well, and the reaction was carried out in the dark at room temperature for 10 minutes, and finally the chemiluminescence intensity was detected with the instrument.
3.8 Data analysis:
Calculation of the percentage of cell viability:

% viability=the luminescence value of the sample/ the luminescence value of the DMSO control× 100.

Calculation of the inhibition percentage of HBV DNA, HBV surface antigen and e antigen.

% Inh.=(1−value of the sample/value of DMSO control)×100.

Calculation of $CC_{50}$ and $EC_{50}$: the $CC_{50}$ and 50% inhibitory concentration ($EC_{50}$) values for HBV of the compounds were calculated using GraphPad Prism software.

TABLE 1

Results of the compounds in the PHH test

| Compound | HBsAg $EC_{50}$ (μM) | HBeAg $EC_{50}$ (μM) | HBV DNA $EC_{50}$ (μM) | $CC_{50}$ (μM) |
|---|---|---|---|---|
| I-1 | 38.07 | 18.09 | 22.20 | >50 |
| I-2 | 0.0135 | 0.0054 | 0.0065 | >50 |
| I-4 | 0.01023 | 0.0032 | 0.004125 | >50 |
| I-5 | 0.105 | 0.009 | 0.011 | >50 |
| I-11 | 0.163 | 0.017 | 0.021 | >50 |
| I-13 | >50 | >5 | >5 | >50 |
| I-14 | >50 | >20 | >20 | >50 |
| I-19 | 39.63 | ~15.01 | 28.380 | >50 |
| I-20 | 0.032 | 0.004 | 0.005 | >50 |
| I-21 | 0.0165 | 0.0048 | 0.0069 | >50 |
| I-22 | >50 | 0.0038 | 0.01 | >50 |
| I-23 | >50 | 0.002 | 0.0083 | >50 |
| I-25 | 0.44 | 0.0632 | 0.0988 | >50 |
| I-27 | >50 | 0.0211 | 0.0167 | >50 |
| I-34 | 0.5943 | 0.0664 | 0.1708 | >50 |
| I-35 | 1.034 | 0.3386 | 1.133 | >50 |
| I-36 | >50 | >50 | 9.958 | >50 |
| I-38 | 0.092 | 0.012 | 0.016 | >50 |
| I-40 | 0.302 | 0.034 | 0.031 | >50 |
| I-43 | >50 | 40.79 | >50 | >50 |
| I-46 | >50 | 6.325 | 48.85 | >50 |
| I-48 | >50 | 0.426 | 4.017 | >50 |
| I-49 | >50 | 41.26 | 10.88 | >50 |
| I-50 | 0.102 | 0.0537 | 0.07754 | >50 |
| I-51 | >50 | 0.01 | 0.0097 | >50 |
| I-53 | 0.115 | 0.0056 | 0.0084 | >50 |
| I-54 | 0.326 | 0.041 | 0.025 | >50 |
| I-65 | 0.0395 | 0.0033 | 0.0030 | >50 |
| I-66 | 0.369 | 0.0317 | 0.0304 | >50 |
| I-67 | 0.1467 | 0.0042 | 0.0179 | >50 |
| I-68 | 0.5821 | 0.0170 | 0.0811 | >50 |
| I-69 | 0.0563 | 0.0113 | 0.0171 | >50 |
| I-70 | 0.04073 | 0.0052 | 0.007125 | >50 |
| I-71 | 0.0924 | 0.0147 | 0.0316 | >50 |
| I-72 | 17.53 | 8.052 | 8.0930 | >50 |
| I-73 | 0.1154 | 0.0120 | 0.0134 | >50 |
| Comparative Compound A: | 9.927 | 6.885 | 0.5755 | >50 |

Comparative compound A was the compound of Embodiment 2 in WO2017202798A1:

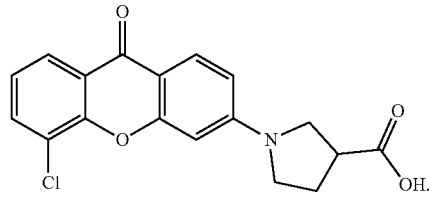 [SMILES: O=C(O)C1CCN(c2ccc3c(=O)c4cccc(Cl)c4oc3c2)C1]

The invention claimed is:
1. A compound as shown in formula I-A, a pharmaceutically acceptable salt thereof, a solvate thereof or a solvate of the pharmaceutically acceptable salt thereof;

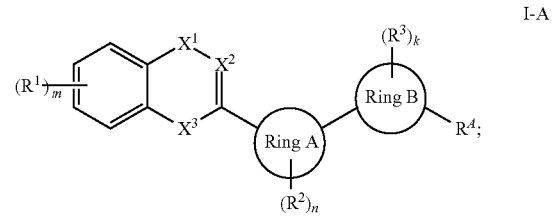

wherein, m is 0, 1 or 2;

$R^1$ is halogen, $C_1$-$C_3$ alkyl, $C_1$-$C_3$ alkyl substituted by one or more halogens, $C_1$-$C_3$ alkoxy, or $C_1$-$C_3$ alkoxy substituted by one or more halogens;

$X^1$ is -C($R^4R^5$)—, or

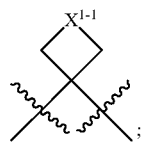

$R^4$ is $C_1$-$C_3$ alkyl, $C_1$-$C_3$ alkyl substituted by one or more halogens, or, $C_3$-$C_5$ cycloalkyl;

$R^5$ is hydrogen, $C_1$-$C_3$ alkyl, $C_1$-$C_3$ alkyl substituted by one or more halogens, or, $C_3$-$C_5$ cycloalkyl;

$X^{1-1}$ is a single bond, O, $CH_2$ or $CH_2CH_2$;

$X^2$ is N, $X^3$ is NH;

ring A is a "5-membered heteroaromatic ring containing 1, 2 or 3 heteroatoms independently selected from N, O and S";

n is 0 or 1;

$R^2$ is halogen, $C_1$-$C_3$ alkyl, $C_1$-$C_3$ alkyl substituted by one or more halogens, $C_1$-$C_3$ alkoxy, or $C_1$-$C_3$ alkoxy substituted by one or more halogens;

ring B is benzene ring or "5- to 6-membered heteroaromatic ring containing 1 or 2 heteroatoms independently selected from N, O and S";

k is 0 or 1;

$R^3$ is halogen, $C_1$-$C_3$ alkyl, $C_1$-$C_3$ alkyl substituted by one or more halogens, $C_1$-$C_3$ alkoxy, or $C_1$-$C_3$ alkoxy substituted by one or more halogens;

$R^A$ is

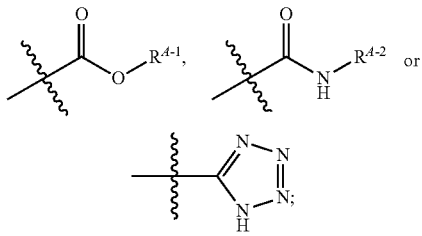

$R^{A-1}$ is hydrogen, or $C_1$-$C_3$ alkyl; $R^{A-2}$ is hydrogen or

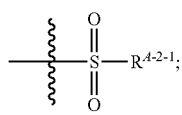

$R^{A-2-1}$ is $C_1$-$C_3$ alkyl.

2. The compound as shown in formula I-A as defined in claim 1, the pharmaceutically acceptable salt thereof, the solvate thereof or the solvate of the pharmaceutically acceptable salt thereof, wherein

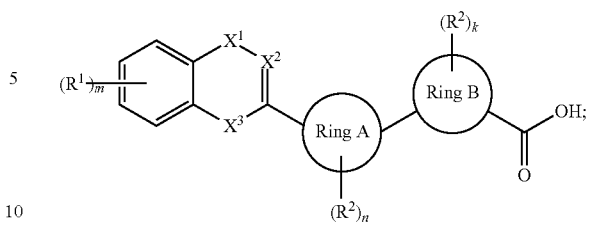

wherein, m is 0, 1 or 2;

$R^1$ is halogen, $C_1$-$C_3$ alkyl, $C_1$-$C_3$ alkyl substituted by one or more halogens, $C_1$-$C_3$ alkoxy, or $C_1$-$C_3$ alkoxy substituted by one or more halogens;

$X^1$ is —C($R^4R^5$)—, or

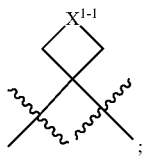

$R^4$ is $C_1$-$C_3$ alkyl, $C_1$-$C_3$ alkyl substituted by one or more halogens, or, $C_3$-$C_5$ cycloalkyl;

$R^5$ is hydrogen, $C_1$-$C_3$ alkyl, $C_1$-$C_3$ alkyl substituted by one or more halogens, or, $C_3$-$C_5$ cycloalkyl;

$X^{1-1}$ is a single bond, O, $CH_2$ or $CH_2CH_2$;

$X^2$ is N;

$X^3$ is NH;

ring A is a "5-membered heteroaromatic ring containing 1, 2 or 3 heteroatoms independently selected from N, O and S";

n is 0 or 1;

$R^2$ is halogen, $C_1$-$C_3$ alkyl, $C_1$-$C_3$ alkyl substituted by one or more halogens, $C_1$-$C_3$ alkoxy, or $C_1$-$C_3$ alkoxy substituted by one or more halogens;

ring B is benzene ring or "5- to 6-membered heteroaromatic ring containing 1 or 2 heteroatoms independently selected from N, O and S";

k is 0 or 1;

$R^3$ is halogen, $C_1$-$C_3$ alkyl, $C_1$-$C_3$ alkyl substituted by one or more halogens, $C_1$-$C_3$ alkoxy, or $C_1$-$C_3$ alkoxy substituted by one or more halogens.

3. The compound as shown in formula I-A as defined in claim 1, the pharmaceutically acceptable salt thereof, the solvate thereof or the solvate of the pharmaceutically acceptable salt thereof, wherein, when $R^1$ is halogen, then the halogen is fluorine, chlorine, bromine or iodine;

or, when $R^1$ is $C_1$-$C_3$ alkyl, then the $C_1$-$C_3$ alkyl is methyl;

or, when $R^1$ is $C_1$-$C_3$ alkyl substituted by one or more halogens, then the halogen is fluorine, chlorine, bromine or iodine;

or, when $R^1$ is $C_1$-$C_3$ alkyl substituted by one or more halogens, then the $C_1$-$C_3$ alkyl is methyl;

or, when $R^1$ is $C_1$-$C_3$ alkoxy, then the $C_1$-$C_3$ alkoxy is methoxyl;

or, when $R^1$ is $C_1$-$C_3$ alkoxyl substituted by one or more halogens, then the halogen is fluorine, chlorine, bromine or iodine;

or, when $R^1$ is $C_1$-$C_3$ alkoxyl substituted by one or more halogens, then the $C_1$-$C_3$ alkoxyl is methoxyl;

or, when m is 1 or 2, then $R^1$ is independently located in the ortho, meta or para position of $X^3$, or, when R⁴ is C₁-C₃ alkyl, then the C₁-C₃ alkyl is methyl or ethyl;
or, when R⁴ is C₁-C₃ alkyl substituted by one or more halogens, then the halogen is fluorine, chlorine, bromine or iodine;
or, when R⁴ is C₁-C₃ alkyl substituted by one or more halogens, then the C₁-C₃ alkyl is methyl;
or, when R⁴ is C₃-C₅ cycloalkyl, then the C₃-C₅ cycloalkyl is cyclopropyl;
or, when R⁵ is C₁-C₃ alkyl, then the C₁-C₃ alkyl is methyl or ethyl;
or, when R⁵ is C₁-C₃ alkyl substituted by one or more halogens, then the halogen is fluorine, chlorine, bromine or iodine;
or, when R⁵ is C₁-C₃ alkyl substituted by one or more halogens, then the C₁-C₃ alkyl is methyl;
or, when R⁵ is C₃-C₅ cycloalkyl, then the C₃-C₅ cycloalkyl is cyclopropyl;
or, when ring A is "5-membered heteroaromatic ring containing 1, 2 or 3 heteroatoms independently selected from N, O and S", then the "5-membered heteroaromatic ring containing 1, 2 or 3 heteroatoms independently selected from N, O and S" is furan ring, pyrrole ring, oxazole ring, thiazole ring, imidazole ring or triazole ring;
or,

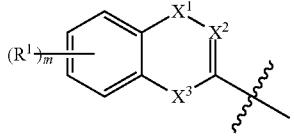

locates in the meta position of ring B;
or, when R² is halogen, then the halogen is fluorine, chlorine, bromine or iodine;
or, when R² is C₁-C₃ alkyl, then the C₁-C₃ alkyl is methyl;
or, when R² is C₁-C₃ alkyl substituted by one or more halogens, then the halogen is fluorine, chlorine, bromine or iodine;
or, when R² is C₁-C₃ alkyl substituted by one or more halogens, the C₁-C₃ alkyl is methyl;
or, when R² is C₁-C₃ alkoxyl, the C₁-C₃ alkyl is methoxyl;
or, when R² is C₁-C₃ alkoxyl substituted by one or more halogens, then the halogen is fluorine, chlorine, bromine or iodine;
or, when R² is C₁-C₃ alkoxyl substituted by one or more halogens, the C₁-C₃ alkoxyl is methoxyl;
or, when n is 1, then R² is independently located in the ortho, meta or para position of ring B;
or, when ring B is "5-membered heteroaromatic ring containing 1 or 2 heteroatoms independently selected from N, O and S", then the "5-membered heteroaromatic ring containing 1 or 2 heteroatoms independently selected from N, O and S" is furan ring, pyrrole ring, oxazole ring, thiazole ring or imidazole ring;
or, when ring B is a "6-membered heteroaromatic ring containing 1 or 2 heteroatoms independently selected from N, O and S", then the "6-membered heteroaromatic ring containing 1 or 2 heteroatoms independently selected from N, O and S" is pyridine ring or pyrimidine ring;
or, when R³ is halogen, then the halogen is fluorine, chlorine, bromine or iodine;
or, when R³ is C₁-C₃ alkyl, the C₁-C₃ alkyl is methyl;

or, when R³ is C₁-C₃ alkyl substituted by one or more halogens, then the halogen is fluorine, chlorine, bromine or iodine;
or, when R³ is C₁-C₃ alkyl substituted by one or more halogens, then the C₁-C₃ alkyl is methyl;
or, when R³ is C₁-C₃ alkoxyl, then the C₁-C₃ alkyl is methoxyl;
or, when R³ is C₁-C₃ alkoxyl substituted by one or more halogens, then the halogen is fluorine, chlorine, bromine or iodine;
or, when R³ is C₁-C₃ alkoxyl substituted by one or more halogens, then the C₁-C₃ alkoxyl is methoxyl;
or, when k is 1, then R³ is independently located in the ortho, meta or para position of ring A;
or, when R^{4-1} is C₁-C₃ alkyl, then the C₁-C₃ alkyl is methyl or ethyl;
or, when R^{4-2-1} is C₁-C₃ alkyl, then the C₁-C₃ alkyl is methyl;
or, R⁴ locates in the ortho, meta or para position of ring A;
or, the atoms in the compound as shown in formula I-A, the pharmaceutically acceptable salt thereof, the solvate thereof, the solvate of the pharmaceutically acceptable salt thereof are present in their natural or unnatural abundance.

4. The compound as shown in formula I-A as defined in claim 3, the pharmaceutically acceptable salt thereof, the solvate thereof or the solvate of the pharmaceutically acceptable salt thereof, wherein, when R¹ is halogen, then the halogen is fluorine, chlorine or bromine;
or, when R¹ is C₁-C₃ alkyl substituted by one or more halogens, then the C₁-C₃ alkyl substituted by one or more halogens is trifluoromethyl;
or, when R¹ is C₁-C₃ alkoxyl substituted by one or more halogens, then the C₁-C₃ alkoxyl substituted by one or more halogens is trifluoromethoxyl;
or, when m is 1, then R¹ is located in the ortho or meta position of X³;
or, when R⁴ is C₁-C₃ alkyl, then the C₁-C₃ alkyl is methyl;
or, when R⁴ is C₁-C₃ alkyl substituted by one or more halogens, then the C₁-C₃ alkyl substituted by one or more halogens is trifluoromethyl;
or, when R⁵ is C₁-C₃ alkyl, then the C₁-C₃ alkyl is methyl;
or, when R⁵ is C₁-C₃ alkyl substituted by one or more halogens, then the C₁-C₃ alkyl substituted by one or more halogens is trifluoromethyl;
or, when ring A is "5-membered heteroaromatic ring containing 1, 2 or 3 heteroatoms independently selected from N, O and S", then the "5-membered heteroaromatic ring containing 1, 2 or 3 heteroatoms independently selected from N, O and S" is furan ring, pyrrole ring, oxazole ring, thiazole ring or imidazole ring;
or, when R² is halogen, then the halogen is fluorine;
or, when R² is C₁-C₃ alkyl substituted by one or more halogens, then the C₁-C₃ alkyl substituted by one or more halogens is trifluoromethyl;
or, when R² is C₁-C₃ alkoxyl substituted by one or more halogens, then the C₁-C₃ alkoxyl substituted by one or more halogens is trifluoromethoxyl;
or, when n is 1, then R² is independently located in the meta position of ring B;
or, when ring B is a "6-membered heteroaromatic ring containing 1 or 2 heteroatoms independently selected from N, O and S", then the "6-membered heteroaromatic ring containing 1 or 2 heteroatoms independently selected from N, O and S" is pyridine ring;
or, when R³ is halogen, then the halogen is fluorine;

or, when $R^3$ is $C_1$-$C_3$ alkyl substituted by one or more halogens, then the $C_1$-$C_3$ alkyl substituted by one or more halogens is trifluoromethyl;

or, when $R^3$ is $C_1$-$C_3$ alkoxyl substituted by one or more halogens, then the $C_1$-$C_3$ alkoxyl substituted by one or more halogens is trifluoromethoxyl;

or, when k is 1, then $R^3$ is independently located in the ortho or meta position of ring A;

or, when $R^{4-1}$ is $C_1$-$C_3$ alkyl, then the $C_1$-$C_3$ alkyl is ethyl;

or, $R^4$ is located in the para position of ring A.

5. The compound as shown in formula I-A as defined in claim 4, the pharmaceutically acceptable salt thereof, the solvate thereof or the solvate of the pharmaceutically acceptable salt thereof, wherein, when $R^1$ is halogen, then the halogen is fluorine or chlorine;

or, when m is 1, then $R^1$ is located in the ortho position of $X^3$;

or, when ring A is "5-membered heteroaromatic ring containing 1, 2 or 3 heteroatoms independently selected from N, O and S", then the "5-membered heteroaromatic ring containing 1, 2 or 3 heteroatoms independently selected from N, O and S" is furan ring, oxazole ring, thiazole ring or imidazole ring.

6. The compound as shown in formula I-A as defined in claim 1, the pharmaceutically acceptable salt thereof, the solvate thereof or the solvate of the pharmaceutically acceptable salt thereof, wherein m is 0 or 1;

or, $R^1$ is halogen, $C_1$-$C_3$ alkyl substituted by one or more halogens, or $C_1$-$C_3$ alkoxy substituted by one or more halogens;

or, when $X^1$ is-$C(R^4R^5)$—, $R^4$ and $R^5$ are independently $C_1$-$C_3$ alkyl, $C_1$-$C_3$ alkyl substituted by one or more halogens, or $C_3$-$C_5$ cycloalkyl;

or, when $X^1$ is

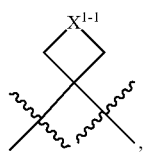

$X^{1-1}$ is a single bond, O or $CH_2$;

or, $X^1$ is-$C(R^4R^5)$—;

or, n is 0;

or, when n is 1, then $R^2$ is halogen, $C_1$-$C_3$ alkyl or $C_1$-$C_3$ alkoxyl;

or, ring B is benzene ring or "6-membered heteroaromatic ring containing 1 or 2 heteroatoms independently selected from N, O and S";

or, k is 0;

or, when k is 1, then $R^3$ is halogen, $C_1$-$C_3$ alkyl or $C_1$-$C_3$ alkoxyl;

or, when $R^4$ is

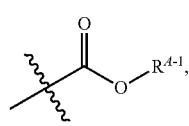

then $R^{4-1}$ is $C_1$-$C_3$ alkyl;

or, $R^4$ is

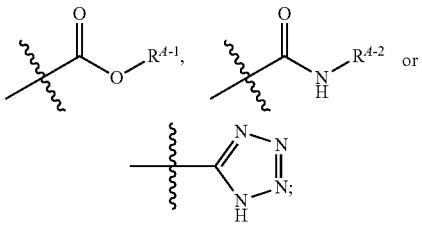

$R^{4-1}$ is $C_1$-$C_3$ alkyl; $R^4$ is hydrogen or

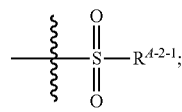

$R^{4-2-1}$ is $C_1$-$C_3$ alkyl.

7. The compound as shown in formula I-A as defined in claim 6, the pharmaceutically acceptable salt thereof, the solvate thereof or the solvate of the pharmaceutically acceptable salt thereof, wherein, $R^1$ is halogen or $C_1$-$C_3$ alkoxy substituted by one or more halogens;

or, when $X^1$ is-$C(R^4R^5)$—, then $R^4$ and $R^5$ are independently $C_1$-$C_3$ alkyl;

or, when $X^1$ is

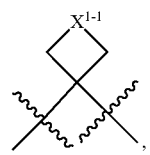

then $X^{1-1}$ is single bond or O;

or,

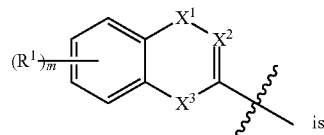

is

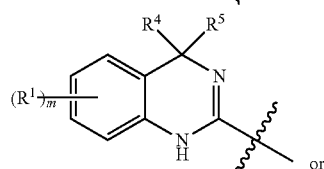

or

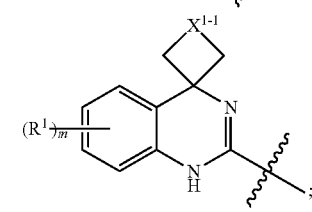

or, when n is 1, then $R^2$ is halogen;
or, ring B is benzene ring;
or, when k is 1, then $R^3$ is halogen or $C_1$-$C_3$ alkoxyl.

8. The compound as shown in formula I-A as defined in claim 1, the pharmaceutically acceptable salt thereof, the solvate thereof or the solvate of the pharmaceutically acceptable salt thereof, wherein the compound is selected from any one of the following schemes:

Scheme 1:
ring A is a "5-membered heteroaromatic ring containing 1, 2 or 3 heteroatoms independently selected from N, O and S";
ring B is benzene ring or "6-membered heteroaromatic ring containing 1 or 2 heteroatoms independently selected from N, O and S";
$R^4$ is

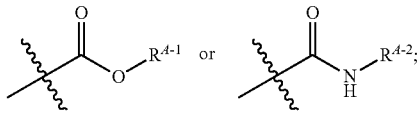

$R^4$ is located in the para position of ring A;
Scheme 2:
ring A is furan ring, oxazole ring, thiazole ring or imidazole ring;
$R^1$ is fluorine, chlorine or trifluoromethoxyl;
m is 0, 1 or 2;
when m is 1, then $R^1$ is independently located in the ortho or para position of $X^3$;
when m is 2, then $R^1$ is independently located in the ortho or meta position of $X^3$;
ring B is benzene ring or "6-membered heteroaromatic ring containing 1 or 2 heteroatoms independently selected from N, O and S";
$R^4$ is

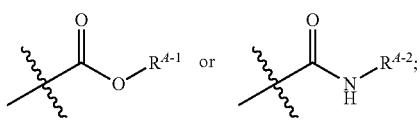

$R^4$ is located in the para position of ring A;
Scheme 3:
m is 0, 1 or 2;
$R^1$ is halogen, $C_1$-$C_3$ alkyl, $C_1$-$C_3$ alkyl substituted by one or more halogens, $C_1$-$C_3$ alkoxy, or $C_1$-$C_3$ alkoxy substituted by one or more halogens;
$X^1$ is -$C(R^4R^5)$—, or

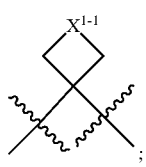

$R^4$ is $C_1$-$C_3$ alkyl, $C_1$-$C_3$ alkyl substituted by one or more halogens, or, $C_3$-$C_5$ cycloalkyl; $R^5$ is hydrogen, $C_1$-$C_3$ alkyl, $C_1$-$C_3$ alkyl substituted by one or more halogens, or, $C_3$-$C_5$ cycloalkyl; $X^{1-1}$ is a single bond, O, $CH_2$ or $CH_2CH_2$;

$X^2$ is N;
$X^3$ is NH;
ring A is a "5-membered heteroaromatic ring containing 1, 2 or 3 heteroatoms independently selected from N, O and S";
n is 0 or 1;
$R^2$ is halogen, $C_1$-$C_3$ alkyl, $C_1$-$C_3$ alkyl substituted by one or more halogens, $C_1$-$C_3$ alkoxy, or $C_1$-$C_3$ alkoxy substituted by one or more halogens;
ring B is benzene ring or "5- to 6-membered heteroaromatic ring containing 1 or 2 heteroatoms independently selected from N, O and S";
k is 0 or 1;
$R^3$ is halogen, $C_1$-$C_3$ alkyl, $C_1$-$C_3$ alkyl substituted by one or more halogens, $C_1$-$C_3$ alkoxy, or $C_1$-$C_3$ alkoxy substituted by one or more halogens;
Scheme 4:
m is 0, 1 or 2;
$R^1$ is halogen, $C_1$-$C_3$ alkyl, or $C_1$-$C_3$ alkyl substituted by one or more;
$X^1$ is -$C(R^4R^5)$—, or

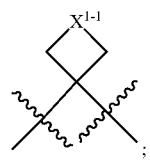

$R^4$ and $R^5$ are independently $C_1$-$C_3$ alkyl, $C_1$-$C_3$ alkyl substituted by one or more halogens, or $C_3$-$C_5$ cycloalkyl; $X^{1-1}$ is a single bond, O or $CH_2$;
$X^2$ is N;
$X^3$ is NH;
ring A is a "5-membered heteroaromatic ring containing 1, 2 or 3 heteroatoms independently selected from N, O and S";
n is 0 or 1;
$R^2$ is halogen, $C_1$-$C_3$ alkyl or $C_1$-$C_3$ alkoxyl;
ring B is benzene ring or "5- to 6-membered heteroaromatic ring containing 1 or 2 heteroatoms independently selected from N, O and S";
k is 0 or 1;
$R^3$ is halogen, $C_1$-$C_3$ alkyl or $C_1$-$C_3$ alkoxyl;
Scheme 5:
m is 0, 1 or 2;
$R^1$ is halogen or $C_1$-$C_3$ alkyl substituted by one or more halogens;
$X^1$ is -$C(R^4R^5)$—;
$R^4$ and $R^5$ are independently $C_{1-3}$ alkyl;
$X^2$ is N;
$X^3$ is NH;
ring A is a "5-membered heteroaromatic ring containing 1, 2 or 3 heteroatoms independently selected from N, O and S";
n is 0 or 1;
$R^2$ is halogen, $C_1$-$C_3$ alkyl or $C_1$-$C_3$ alkoxyl;
ring B is benzene ring;
k is 0 or 1;
$R^3$ is halogen, $C_1$-$C_3$ alkyl or $C_1$-$C_3$ alkoxyl;
Scheme 6:
m is 0 or 1;
$R^1$ is halogen;
$X^1$ is -$C(R^4R^5)$—;
$R^4$ is $C_1$-$C_3$ alkyl; $R^5$ is hydrogen or $C_1$-$C_3$ alkyl;

X² is N;

X³ is NH;

ring A is a "5-membered heteroaromatic ring containing 1, 2 or 3 heteroatoms independently selected from N, O and S";

n is 0;

ring B is benzene ring;

k is 0.

9. The compound as shown in formula I-A as defined in claim 1, the pharmaceutically acceptable salt thereof, the solvate thereof or the solvate of the pharmaceutically acceptable salt thereof, wherein, the compound as shown in formula I-A is selected from any of the following compounds:

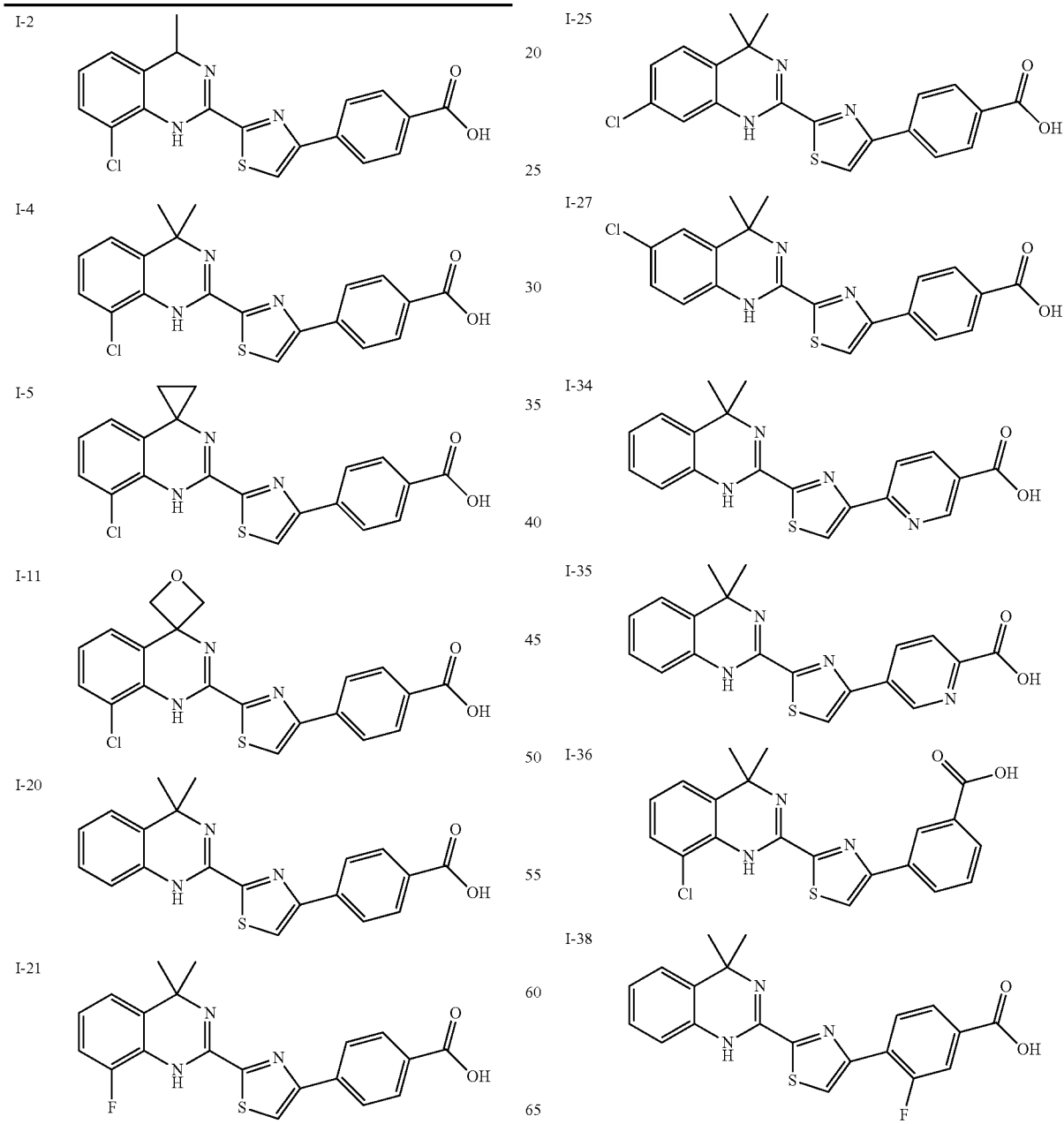

I-40 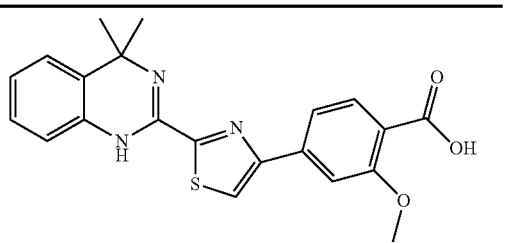

I-50 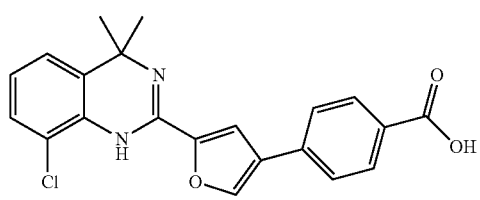 [SMILES: CC1(C)N=C(c2cc(-c3ccc(C(=O)O)cc3)co2)Nc2c(Cl)cccc21]

I-51 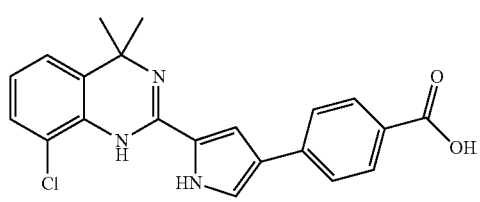 [SMILES: CC1(C)N=C(c2cc(-c3ccc(C(=O)O)cc3)c[nH]2)Nc2c(Cl)cccc21]

I-53 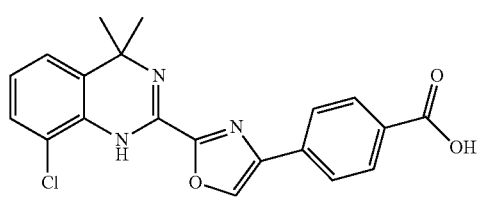

I-54 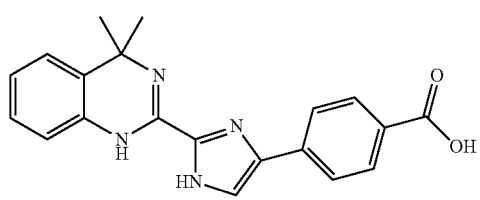 [SMILES: CC1(C)N=C(c2nc(-c3ccc(C(=O)O)cc3)c[nH]2)Nc2ccccc21]

I-65 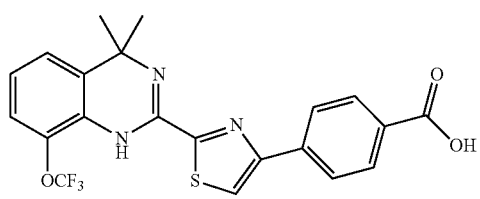 [SMILES: CC1(C)N=C(c2nc(-c3ccc(C(=O)O)cc3)cs2)Nc2c(OC(F)(F)F)cccc21]

I-66 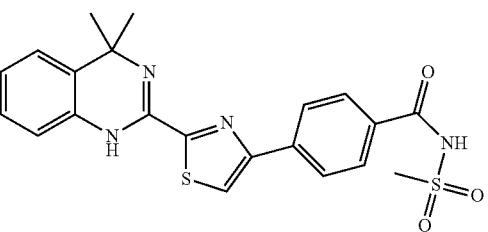 [SMILES: CC1(C)N=C(c2nc(-c3ccc(C(=O)NS(C)(=O)=O)cc3)cs2)Nc2ccccc21]

I-69 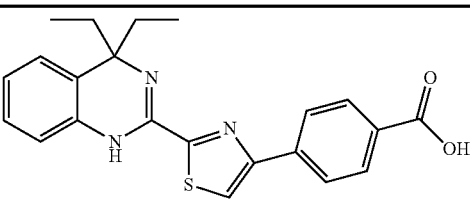

I-70 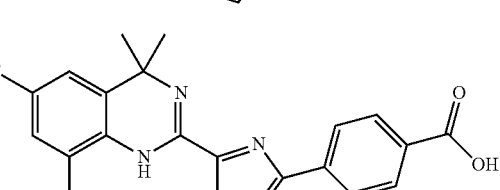

I-71 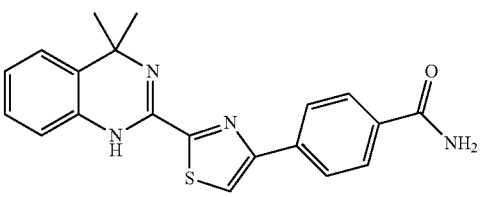 [SMILES: CC1(C)N=C(c2nc(-c3ccc(C(N)=O)cc3)cs2)Nc2ccccc21]

I-72 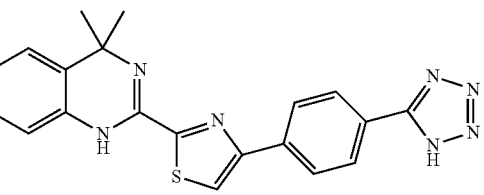

I-73 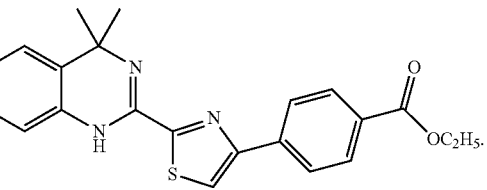

10. A pharmaceutical composition comprising a substance X and a pharmaceutical excipient;
the substance X is the compound as shown in formula I-A as defined in claim 1, the pharmaceutically acceptable salt thereof, the solvate thereof or the solvate of the pharmaceutically acceptable salt thereof.

11. A method for the treatment of Hepatitis B, comprising administering an effective amount of the substance X to a subject; the substance X is the compound as shown in formula I-A as defined in claim 1, the pharmaceutically acceptable salt thereof, the solvate thereof or the solvate of the pharmaceutically acceptable salt thereof.

12. A method for the treatment of Hepatitis B, comprising administering an effective amount of the substance X and other medicaments for the treatment of hepatitis B to a subject; the substance X is the compound as shown in formula I-A as defined in claim 1, the pharmaceutically acceptable salt thereof, the solvate thereof or the solvate of the pharmaceutically acceptable salt thereof.

* * * * *